(12) United States Patent
Zhu et al.

(10) Patent No.: US 11,073,482 B2
(45) Date of Patent: *Jul. 27, 2021

(54) MULTI-FUNCTIONAL PRECIOUS STONE TESTING APPARATUS AND METHOD THEREOF

(71) Applicant: Shenzhen Dikai Industrial Co., Ltd., Shenzhen (CN)

(72) Inventors: Xiuling Zhu, Shenzhen (CN); Gary Bruce Peckham, Shenzhen (CN)

(73) Assignee: Shenzhen Dikai Industrial Co., Ltd., Shenzhen (CN)

( * ) Notice: Subject to any disclaimer, the term of this patent is extended or adjusted under 35 U.S.C. 154(b) by 223 days.

This patent is subject to a terminal disclaimer.

(21) Appl. No.: 16/231,296

(22) Filed: Dec. 21, 2018

(65) Prior Publication Data

US 2019/0137406 A1 May 9, 2019

Related U.S. Application Data

(63) Continuation of application No. 14/961,843, filed on Dec. 7, 2015, now Pat. No. 10,203,288, which is a (Continued)

(51) Int. Cl.
| | |
|---|---|
| *G01N 25/18* | (2006.01) |
| *G01N 21/87* | (2006.01) |
| *G01N 21/63* | (2006.01) |
| *G01N 27/04* | (2006.01) |
| *G01N 21/88* | (2006.01) |

(Continued)

(52) U.S. Cl.
CPC ............. *G01N 21/87* (2013.01); *G01N 21/25* (2013.01); *G01N 21/33* (2013.01); *G01N 21/35* (2013.01); *G01N 21/63* (2013.01); *G01N 21/8803* (2013.01); *G01N 25/18* (2013.01); *G01N 27/02* (2013.01); *G01N 27/041* (2013.01); *G01N 33/381* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,265,884 B1 * | 7/2001 | Menashi | ............... | G01N 27/041 324/693 |
| 7,362,109 B2 * | 4/2008 | Loginov | ............... | G01N 27/041 324/691 |

(Continued)

*Primary Examiner* — Lisa M Caputo
*Assistant Examiner* — Nasir U. Ahmed
(74) *Attorney, Agent, or Firm* — Raymond Y. Chan; David and Raymond Patent Firm

(57) ABSTRACT

A multi-functional precious stone testing apparatus includes a microcontroller, a measuring unit for measuring properties of the testing object, and a functional unit. The measuring unit is arranged to measure one of a combination of ultraviolet and infrared distributions of the testing object and a combination of thermal and electrical conductivities of the testing object. The microcontroller analyzes a result from the measuring unit to generate a test result of the testing object, wherein the microcontroller includes a communication unit for connecting with an electronic device to transmit the test result thereto. The functional unit includes a voice indicator that generates a voice indication signal of the test result.

19 Claims, 44 Drawing Sheets

Related U.S. Application Data continuation-in-part of application No. 14/564,041, filed on Dec. 8, 2014, now Pat. No. 9,453,808, which is a continuation-in-part of application No. 12/932,109, filed on Feb. 16, 2011, now Pat. No. 8,947,111.

(51) Int. Cl.
| | | |
|---|---|---|
| *G01N 33/38* | (2006.01) | |
| *G01N 21/25* | (2006.01) | |
| *G01N 21/33* | (2006.01) | |
| *G01N 21/35* | (2014.01) | |
| *G01N 27/02* | (2006.01) | |

(56) References Cited

U.S. PATENT DOCUMENTS

| | | | | |
|---|---|---|---|---|
| 7,598,685 | B1* | 10/2009 | Shteynberg | H05B 45/37 315/308 |
| 7,843,330 | B2* | 11/2010 | Chamberlain | G16H 40/63 340/539.12 |
| 2009/0182520 | A1* | 7/2009 | Luxembourg | G01N 33/381 702/81 |
| 2012/0049836 | A1* | 3/2012 | Kessler | G01N 33/24 324/71.1 |

* cited by examiner

Gemstone Color Chart

| Name | Red | Pink | Orange | Brown | Yellow | Green | Blue | Violet | Purple | White | Black | Colorless |
|---|---|---|---|---|---|---|---|---|---|---|---|---|
| Glass | Red | Pink | Orange | Brown | Yellow | Green | Blue | Violet | Purple | White | Black | Colorless |
| Lolite | | | | | | | Blue | Violet | Purple | | | |
| Almandine | Red | | | | | | | Violet | Purple | | | |
| Pyrope | Red | | | | | | | | Purple | | | |
| Spessartite | Red | | Orange | | Yellow | | | | | | | |
| Nephrite | | | Orange | Brown | | Green | Blue | | | White | Black | |
| Tanzanite | | | | | | | Blue | Violet | Purple | | | |
| Chrysoprase | | | | | | Green | | | | | | |
| Goshenite | | | | | | | | | | | | Colorless |
| Helidor | | | | | Yellow | | | | | | | |
| Aquamarine | | | | | | Green | Blue | | | | | |
| Morganite | | Pink | | | | | | Violet | | | | |
| Emerald | | | | | | Green | | | | | | |
| Tourmaline | | | Orange | Brown | Yellow | | | Violet | Purple | White | Black | Colorless |
| Paraiba | | | | | | Green | Blue | | | | | |
| Rubellite | Red | Pink | | | | | | | | | | |
| Peridot | | | | | Yellow | Green | | | | | | |
| Hessonite | | | Orange | Brown | Yellow | | | | | | | |
| Tsavorite | | | | | | Green | | | | | | |
| Demantoid | | | | | Yellow | Green | | | | | | |
| Jadeite | Red | | Orange | Brown | Yellow | Green | Blue | Violet | | White | Black | |
| Quartz | | | | Brown | | | | | | | | Colorless |
| Aventurine | | | | | | Green | | | | | | |
| Citrine | | | Orange | | Yellow | | | | | | | |
| Amethyst | | | | | | | | Violet | Purple | | | |
| Spinel | Red | Pink | Orange | Brown | | Green | Blue | Violet | Purple | | Black | Colorless |
| Chrysoberyl | | Pink | Orange | Brown | Yellow | Green | Blue | Violet | Purple | White | Black | Colorless |
| Topaz | Red | Pink | Orange | Brown | Yellow | Green | Blue | | | | | Colorless |
| Sapphire | | Pink | Orange | Brown | Yellow | Green | Blue | Violet | Purple | | | Colorless |
| Ruby | Red | Pink | | | | | | | | | | |
| Diamond | | | | | | | | | | | | Colorless |
| Moissanite | | | | | | | | | | | | Colorless |

FIG. 39

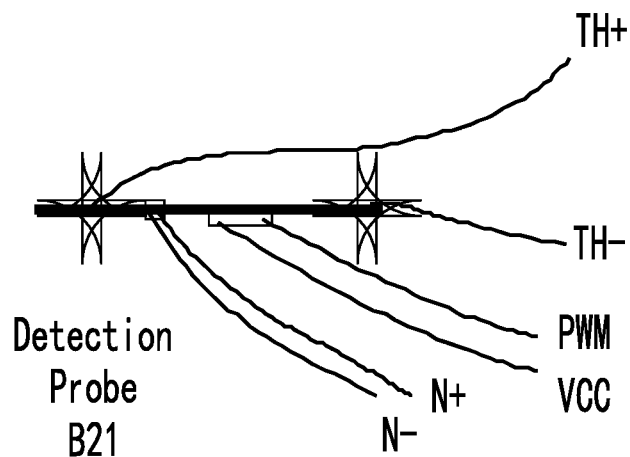
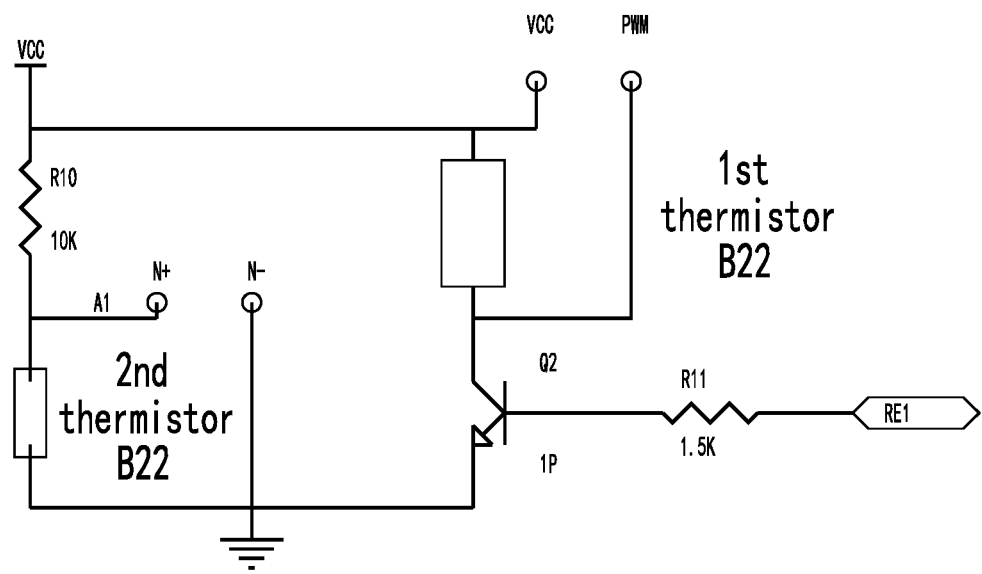
FIG. 44

MULTI-FUNCTIONAL PRECIOUS STONE TESTING APPARATUS AND METHOD THEREOF

CROSS REFERENCE OF RELATED APPLICATION

This is a Continuation application that claims of priority under 35 U.S.C. § 119 to a U.S. non-provisional application, application Ser. No. 14/961,843, filed Dec. 7, 2015, which is a Continuation-In-Part application that claims the benefit of priority under 35 U.S.C. § 119 to a non-provisional application, application Ser. No. 14/564,041, filed Dec. 8, 2014, which is a Continuation-In-Part application that claims the benefit of priority under 35 U.S.C. § 119 to a non-provisional application, application Ser. No. 12/932,109, filed Feb. 16, 2011.

The non-provisional application, application Ser. No. 14/961,843, also claimed priority to Chinese application number CN201510568297.6, filed Sep. 9, 2015 and Chinese application number CN20151 0570210.9, filed Sep. 9, 2015.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a precious stone tester, and more particular to a multi-functional precious stone testing apparatus and method thereof, which comprises a LED light unit for providing an illumination at the conductive probe for determining thermal and/or electrical conductivity when the conductive probe contacts with the testing object without substantially transmitting heat from the LED light unit to the conductive probe. The multi-functional precious stone testing apparatus and method thereof is adapted to determine the authenticity of the precious stone.

Description of Related Arts

Diamonds are aristocracy jewelries that are signify steadfast, enduring love because of their crystal brightness and crisp elegance. These fine jewelries are flaunted and coveted. With the rapid development of technology in the diamond manufacturing industry, artificial diamonds can be produced synthetically in different methods from carbon material in a low cost. In addition, a variety of colors of artificial diamonds can be simply made in the emerging markets. However, due to the quality of artificial diamonds is far less than that of the natural diamonds, the price of artificial diamonds is lower than that of the natural diamonds. Accordingly, under the fair trade law requirements, artificial diamond dealers must truthfully claim the quality of artificial diamonds that the certificate thereof must state the artificial diamonds generally with the term of as "synthetic", "artificial" or "laboratory manufacturing", etc., to protect the consumers.

As it is mentioned above, the artificial diamonds can be produced synthetically in HPHT (High Pressure, High Temperature) method or CVD (Chemical Vapor Deposition) method. It is called HPHT diamonds when the artificial diamonds are produced synthetically in HPHT method, and CVD diamonds when the artificial diamonds are produced synthetically in CVD method. Accordingly, natural diamonds are considered as real diamonds and HPHT/CVD diamonds are considered as lab-grown diamonds or fake diamonds. In addition, the hardness of the artificial diamonds is stronger than that of the natural diamonds, such that it is an excellent product for being used in medical field or other industrial production. However, the artificial diamonds should not be compatible with the natural diamonds in the jewelry industry, wherein the artificial diamond dealers should not sell the artificial diamonds with the price of the natural diamonds. It is unfair for the consumers to pay the higher price for the artificial diamonds and it is disturbing in the diamond industry that the artificial diamonds threaten profitability and sustainability in the long run.

As the artificial diamond manufacturing technology is getting mature, artificial diamonds and natural diamonds are difficult to segregate. In particular, people are unable to distinguish the artificial diamonds and natural diamonds by their color and hardness. In other words, the identification of artificial diamonds by observation has become more difficult. Currently, the identification of artificial diamonds relies on specialized accreditation institutions and/or specialized instruments. However, the accreditation cost is relatively high and the instruments are expansive. In fact, there are few certificated accreditation institutions in the jewelry industry to provide well-equipped laboratories for identifying the artificial diamonds and natural diamonds. Therefore, there has no protection for the consumers if the artificial diamond dealers fraudulently sell the artificial diamonds to the consumers.

Under the impact of artificial diamonds, diamond manufacturers intentionally produce synthetic traces embedded in the natural diamonds, which makes people more difficult to distinguish the artificial diamonds and natural diamonds. As a result, it is a need for the diamond dealers and/or consumers to seek a new technology to accurately, quickly, and easily distinguish the artificial diamonds and natural diamonds.

Furthermore, there are many different kinds and colors of precious stones in the market for consumers. In fact, many consumers would like to buy the synthetic diamond because of the low price and diamond-like quality. On the other hand, since there are lots of different kinds of synthetic diamonds in the market, most consumers may not able to identify the materials of the synthetic diamonds or the species of the synthetic diamonds. Even though the synthetic diamonds are cheaper than the natural diamonds, the prices of different species of synthetic diamonds are various. Therefore, it is a need to provide a testing apparatus and method to rapidly and accurately distinguish different kinds of precious stones.

A gemstone tester is considered as one of the convenient tools for gemstone (such as diamond, moissanite and other precious stones) identification. A conventional gemstone tester comprises a testing probe for determining a thermal conductivity of the gemstone such as diamond as well as an electrical conductivity of moissanite in order to classify the gemstone by its physical properties. However, the gemstone tester has several drawbacks. The user must be proficient in the relevant skill and techniques to operate the gemstone tester and with a relatively practical understanding of the theoretical principles of gemstone because the gemstone tester must be adjusted or regulated its parameters during testing operation. The testing errors will be obtained due to the insufficient sensitivity of the gemstone tester or the improper operation of the gemstone tester. In addition, the gemstone tester can only test a particular gemstone. Therefore, it is a hassle for the user to carry different gemstone tester in order to test various kinds of gemstones. Furthermore, the gemstone tester can only identify whether the gemstone is real, however, the gemstone tester cannot measure the fluorescence of gemstones through the visible light. In other words, the user must carry another tester in order to measure the fluorescence of gemstones.

An improved gemstone tester further comprises an illumination unit for illuminating the testing probe when the testing probe contacts with the gemstone. The illumination unit comprises a light-up frame, wherein the light-up frame forms a tip holding frame to retain the testing probe in position. In other words, the testing probe is extended through and supported at the light-up frame. Therefore, the light-up frame provides enough illumination at the tip of the testing probe in order to accurately contact the tip of the testing probe at the gemstone.

However, the illumination unit not only generates light to the light-up frame but also generates heat toward the testing probe because the illumination unit is positioned close to the testing probe. Since the testing probe is arranged for determining the conductivity of the gemstone, heat from the illumination unit will affect the accuracy of conductivity of the gemstone.

SUMMARY OF THE PRESENT INVENTION

The invention is advantageous in that it provides a multifunctional precious stone testing apparatus and method thereof, which comprises a LED light unit for providing an illumination at the conductive probe when the conductive probe contacts with the testing object without substantially transmitting heat from the LED light unit to the conductive probe.

Another advantage of the invention is to provide a multifunctional precious stone testing apparatus and method thereof, which can accurately classify the testing object as one of Moissanite, diamond, metal, and other stone.

Another advantage of the invention is to provide a multifunctional precious stone testing apparatus and method thereof, which comprises a UV light source for generating a UV light beam toward the testing object to measure the fluorescence of the testing object. In particular, the conductive probe and the UV light source are operated independently.

Another advantage of the invention is to provide a multifunctional precious stone testing apparatus and method thereof, wherein the light transmissible frame is coupled between the hand-held casing and the probe casing to diffuse the light from the LEDs for illumination of the testing end portion of the conductive probe.

Another advantage of the invention is to provide a multifunctional precious stone testing apparatus and method thereof, wherein the operation of the present invention is simple and easy by contacting the thumb and index finger of the user at the touch control and by contacting the testing end portion of the conductive probe at the testing object.

Another advantage of the invention is to provide a multifunctional precious stone testing apparatus and method thereof, wherein the LED indentifying indicators are formed on the top wall of the portable housing for easy reading.

Another advantage of the invention is to provide a multifunctional precious stone testing apparatus and method thereof, which is able to determine the authenticity of the precious stone, especially for the indentifying the natural diamonds and lab-grown diamonds such as HPHT diamonds or CVD diamonds.

Another advantage of the invention is to provide a multifunctional precious stone testing apparatus and method thereof, which is able to distinguish between natural diamonds and synthetic diamonds by the differential characteristics between the natural diamonds and synthetic diamonds, by the differential absorption of different wavelengths of ultraviolet, and by different light refractions of infrared light, so as to enhance an accuracy of the test result.

Another advantage of the invention is to provide a multifunctional precious stone testing apparatus, which is compact, portable, and easy to use.

Another advantage of the invention is to provide a multifunctional precious stone testing method, which is easy of operation through simple steps to generate the accurate test result.

Another advantage of the invention is to provide a multifunctional precious stone testing apparatus and method thereof, which can be connected to an external electronic device to transmit the test data thereto, such that the user is able to store the test data digitally and view the test data through the electronic device.

Another advantage of the invention is to provide a multifunctional precious stone testing apparatus and method thereof, which provide a quick and accurate testing method to shorten the testing time for distinguishing between natural diamonds and synthetic diamonds.

Another advantage of the invention is to provide a multifunctional precious stone testing apparatus and method thereof, wherein the apparatus has advantages of low power consumption, rechargeable, and re-usable, such that the apparatus is an environmentally friendly product for gem testing.

Another advantage of the invention is to provide a multifunctional precious stone testing apparatus and method thereof, which provides multifunction for generating different test results in different ways so as to facilitate the user to view the test results in a timely manner.

Another advantage of the invention is to provide a multifunctional precious stone testing apparatus and method thereof, wherein the testing object is tested in a closed environment test to prevent UV leakage which is harmful for human being.

Another advantage of the invention is to provide a multifunctional precious stone testing apparatus and method thereof, wherein, through the characteristics of natural diamonds, Moissanite, and colored gemstones, the testing apparatus is able to distinguish natural diamonds, moissanite and other colored gemstones via the thermal conductivity, the electrical conductivity, and color. Therefore, the testing apparatus is able to test variety of precious stones to meet the market need.

Another advantage of the invention is to provide a multifunctional precious stone testing apparatus and method thereof, wherein information of physical characteristics and chemical properties of various types of precious stones are pre-stored in the microcontroller, such that the present invention compares the pre-stored data with the measured data from the testing object in order to rapidly identify the testing object.

Another advantage of the invention is to provide a multi-functional precious stone testing apparatus and method thereof, wherein the test result will be sent to the electronic device via a wireless communication network, such as WiFi, Bluetooth, or other wireless means. Therefore, the test result can be stored digitally, viewed, accessed, and edited via the electronic device.

Additional advantages and features of the invention will become apparent from the description which follows, and may be realized by means of the instrumentalities and combinations particular point out in the appended claims.

According to the present invention, the foregoing and other objects and advantages are attained by a multi-functional precious stone testing apparatus, which comprises a portable housing, a testing unit, and an indication unit.

The portable housing comprises a hand-held casing for receiving a power source therein, and a probe casing extended from a front end of the hand-held casing.

The testing unit comprises an evaluation circuit received in the hand-held casing and electrically linked with the power source, and a conductive probe operatively linked to the evaluation circuit, wherein the conductive probe has a testing end portion extended out of a tip end of the probe casing for contacting a testing object to determine a thermal and electrical conductivity of the testing object.

The indication unit comprises a LED light unit received in the hand-held casing and operatively linked to the evaluation circuit for generating a light indicating effect to identify the testing object in responsive to the conductivity of the testing object and for illuminating the testing end portion of the conductive probe during testing, wherein the LED light unit is positioned away from the tip end of the probe casing for preventing heat generated from the LED light unit being transmitted toward the conductive probe to affect an accurate measurement for the thermal and/or electrical conductivity of the testing object.

In accordance with another aspect of the invention, the present invention comprises a method of classifying a testing object by a multi-functional precious stone testing apparatus which comprises a hand-held casing and a probe casing extended therefrom, wherein the method comprises the following steps.

(1) Determine a thermal and/or electrical conductivity of the testing object by contacting a testing end portion of a conductive probe of a conduction unit of the testing unit to the testing object, wherein the testing end portion of the conductive probe is extended out of a tip end of the probe casing.

(2) Illuminate the testing end portion of the conductive probe by a LED light unit which is positioned away from the tip end of the probe casing for preventing heat generated from the LED light unit being transmitted toward the conductive probe to affect an accurate measurement for the thermal and/or electrical conductivity of the testing object.

(3) Activate one of a plurality of indicating lights in responsive to the corresponding conductivity of the testing object to classify the testing object as one of Moissanite, diamond, metal, and other stone.

In accordance with another aspect of the invention, the present invention comprises a multi-functional precious stone testing apparatus, which comprises:

an infrared test system which comprises an infrared transmitter for emitting infrared to the surface of the testing object, and an infrared receiver receiving a reflection of the infrared from the surface of the testing object;

a UV transmission system which comprises a short-wave ultraviolet UVA transmitter and a long-wave ultraviolet UVA transmitter for emitting short-wave ultraviolet (UVC) and long-wave ultraviolet (UVA) to penetrate the testing object;

a UV receiving system which comprises a short-wave ultraviolet sensor and a long-wave ultraviolet sensor for receiving the short-wave ultraviolet and long-wave ultraviolet after the penetration through the testing object; and a microcontroller operatively linked to the infrared receiver of the infrared test system and the UV receiving system for receiving infrared data and UV data and for analysis processing the infrared data and UV data so as to generate a test result of the testing object.

Accordingly, the testing apparatus further comprises a power supply system which comprises a power supplier for supplying adequate power to the infrared test system, the UV transmission system, the UV receiving system, and the microcontroller for operation.

The short-wave ultraviolet UVC transmitter comprises a boost inverter circuit and at least one short-wave ultraviolet light device. The long-wave ultraviolet UVA transmitter comprises a constant current circuit and at least one long-wave ultraviolet light device, wherein the boost inverter circuit and the constant current circuit are connected to the power supply system. The short-wave ultraviolet light device and the long-wave ultraviolet light device are activated to emit UVC and UVA respectively.

The microcontroller comprises a processing unit, a transmission unit and a communication unit. The processing unit is operatively linked to the UV receiving system for processing and analyzing the UV data so as to generate the test result. The transmission unit is operatively linked to the processing unit to transmit the test result to a functional unit and to transmit the test result to an external electronic device through the communication unit, such that the test result can be stored digitally, viewed, accessed, and edited via the electronic device.

The functional unit comprises a light indicator and a voice indicator which are connected to the power supplier and the transmission unit, wherein the test results are sent by the transmission unit to identify the testing object via a light indication signal from the light indicator and/or via a voice indication signal from the voice indicator. Therefore, the test result can be presented in different ways.

The test result is determined by the following criteria. The testing object is determined as Moissanite when the short-wave ultraviolet and the long-wave ultraviolet received by the short-wave ultraviolet sensor and the long-wave ultraviolet sensor are weak. The light indicator will generate a green light and the voice indicator will generate a voice of "Moissanite". The testing object is determined as natural diamond when the short-wave ultraviolet received by the short-wave ultraviolet sensor is weak and the long-wave ultraviolet received by the long-wave ultraviolet sensor is strong. The light indicator will generate a blue light and the voice indicator will generate a voice of "natural diamond". The testing object is determined as synthetic diamond when the short-wave ultraviolet received by the short-wave ultraviolet sensor is strong. The light indicator will generate a yellow light and the voice indicator will generate a voice of "synthetic diamond". It is worth mentioning that the test of synthetic diamond should be further identified for accuracy. According to the above three test results, the present invention is adapted to simultaneously display the relevant results.

According to the present invention the testing apparatus has the test area, the testing object is placed in the test area which is a closed environment.

The microcontroller further comprises a detection unit to detect the proper operations of the infrared test system, the UV transmission system, the UV receiving system, the microcontroller, and the functional unit, and the placement of the testing object in the test area.

In accordance with another aspect of the invention, the present invention comprises a method of classifying a testing object, i.e. the distinguish between natural diamonds and synthetic diamonds, by a multi-functional precious stone testing apparatus, wherein the method comprises the following steps.

(A) Emit infrared to the surface of the testing object, and emit UVC and UVA to penetrate the testing object.

(B) Receive the reflection of infrared from the surface of the testing object and the UVC and UVA after the penetration of the testing object, and send infrared data and UV data to the microcontroller.

(C) Analyze UV intensity from the UV data and infrared spectrum from the infrared data to identify the testing object.

In the step (A), UVC and UVA are emitted by the short-wave ultraviolet UVA transmitter and the long-wave ultraviolet UVA transmitter respectively. The infrared is emitted by the infrared transmitter.

The short-wave ultraviolet UVC transmitter comprises a boost inverter circuit and at least one short-wave ultraviolet light device. The long-wave ultraviolet UVA transmitter comprises a constant current circuit and at least one long-wave ultraviolet light device, wherein the boost inverter circuit and the constant current circuit are connected to the power supply system. The short-wave ultraviolet light device and the long-wave ultraviolet light device are activated to emit UVC and UVA respectively. The infrared transmitter comprises a voltage regulating circuit and an infrared light device which is activated by the voltage regulating circuit for emitting the infrared radiation to the surface of the testing object.

In the step (C), the microcontroller is arranged for receiving infrared data and UV data and for analysis processing the infrared data and UV data so as to generate a test result of the testing object. The microcontroller will further send the test result to the functional unit for further rendering.

Accordingly, the microcontroller will analyze the intensity of the UVC and UVA from the short-wave ultraviolet sensor and the long-wave ultraviolet sensor to identify the testing object whether it is natural diamond, Moissanite, or synthetic diamond.

The microcontroller will send the test result to at least one of a light indicator, a voice indicator, and a display. Therefore, the test result can be presented in different ways.

In the step (C), the testing object is determined as Moissanite when the short-wave ultraviolet and the long-wave ultraviolet received by the short-wave ultraviolet sensor and the long-wave ultraviolet sensor are weak. The light indicator will generate a green light and the voice indicator will generate a voice of "Moissanite". The testing object is determined as natural diamond when the short-wave ultraviolet received by the short-wave ultraviolet sensor is weak and the long-wave ultraviolet received by the long-wave ultraviolet sensor is strong. The light indicator will generate a blue light and the voice indicator will generate a voice of "natural diamond". The testing object is determined as synthetic diamond when the short-wave ultraviolet received by the short-wave ultraviolet sensor is strong. The light indicator will generate a yellow light and the voice indicator will generate a voice of "synthetic diamond".

Accordingly, the microcontroller will send the test result to the electronic device via a wireless communication network, such as WiFi, Bluetooth, or other wireless means. Therefore, the test result can be stored digitally, viewed, accessed, and edited via the electronic device.

In accordance with another aspect of the invention, the present invention comprises a multi-functional precious stone testing apparatus, which comprises:

a microcontroller which comprises an amplifying circuit, a processing unit, a transmission unit, and a booster circuit, wherein the processing unit is operatively linked to the amplifying circuit, the transmission unit, and the booster circuit;

a probe head assembly which comprises at least a detection probe operatively connected to the processing unit and at least a thermistor operatively connected to the detection probe, wherein the detection probe is arranged for measuring a thermal conductivity of the testing object when the detection probe contacts therewith. Therefore, a thermal conductive signal is collected and amplified by the amplifying circuit, and is then transmitted to the processing unit for analyzing and processing of the strength of the thermal conductivity of the testing object; and an electrical conductive assembly which comprises at least an electrical member operatively linked to the booster circuit, and an electrical conductor, wherein when the booster circuit is activated to controllably regulate a voltage of the electrical member, such that the electrical conductor contacts with the testing object to measure the electrical conductivity of the testing object. An electrical conductive signal is collected and is transmitted to the processing unit for analyzing and processing of the strength of the electrical conductivity of the testing object. In other words, the processing unit will comprehensively analyze and process the strengths of the thermal conductivity and the electrical conductivity of the testing object in order to identify the testing object. A test result will be generated and transmitted via the transmission unit.

The testing apparatus further comprises a functional unit which comprises a light indicator, a voice indicator, and a display, which are connected to the transmission unit, wherein the test results are sent by the transmission unit to identify the testing object via a light indication signal from the light indicator, via a voice indication signal from the voice indicator, and/or visually displayed via the display. Therefore, the test result can be presented in different ways.

The microcontroller further comprises a communication unit operatively linked to the transmission unit, wherein the communication unit is adapted to send the test result to an electronic device via a wireless communication network, such as WiFi, Bluetooth, or other wireless means. Therefore, the test result can be stored digitally, viewed, accessed, and edited via the electronic device. It is worth mentioning that the test result can be sent to a "cloud storage" via the communication unit.

The microcontroller further comprises a detection unit for automatically detecting whether the testing apparatus operates properly or not.

The functional unit further comprise a power supplier which comprises a rechargeable battery.

Accordingly, the functional unit further comprise a functional key operatively linked to the display to select options of the display and information of the test result to be displayed on the display.

Preferably, the display is a touch screen display.

The testing apparatus of the present invention further comprises a portable housing which comprises a probe casing for housing the detection probe and a display housing for housing the display.

In accordance with another aspect of the invention, the present invention comprises a method of classifying a testing object by a multi-functional precious stone testing apparatus, wherein the method comprises the following steps.

(A) Contact the detection probe with the testing object.

(B) Controllably activate at least a thermistor, preferably two, to control a heat energy change of the detection probe for measuring the thermal conductivity of the testing object, and send a corresponding thermal conductive signal to the microcontroller for analyzing and processing of the strength of the thermal conductivity of the testing object.

(C) Activate the booster circuit controllably regulate a voltage of the electrical member, preferably high voltage, to electrically conduct with the testing object for measuring the electrical conductivity of the testing object, and send a corresponding electrical conductive signal to the microcontroller for analyzing and processing of the strength of the electrical conductivity of the testing object.

(D) Comprehensively analyze and process the strengths of the thermal conductivity and the electrical conductivity of the testing object via the microcontroller in order to identify the testing object.

It is worth mentioning that the step (B) and step (C) can be performed at the same time to simultaneously measure the thermal conductivity and the electrical conductivity of the testing object. Alternatively, the step (B) can be performed before the step (C) to measure the thermal conductivity and the electrical conductivity of the testing object in a sequence.

The microcontroller comprises a processing unit and a transmission unit, wherein the processing unit is arranged for analyzing and processing the strengths of the thermal conductivity and the electrical conductivity of the testing object to generate a test result which is then transmitted via the transmission unit.

The test results are sent by the transmission unit to identify the testing object via a light indication signal from the light indicator, via a voice indication signal from the voice indicator, and/or visually displayed via the display.

In the step (D), the test result is determined by the following criteria. The testing object is determined as Moissanite when the strengths of the thermal conductivity and the electrical conductivity are strong. The testing object is determined as natural diamond when the strength of the thermal conductivity is strong and the strength of the electrical conductivity is weak. The testing object is determined as metal element when the strength of the thermal conductivity is weak and the strength of the electrical conductivity is strong. The testing object is determined as "other gemstones" when the strengths of the thermal conductivity and the electrical conductivity are weak. It is worth mentioning that the test of "other gemstones" should be further identified for accuracy.

Accordingly, the processing unit comprises a properties database containing thermal conductivity data, electrical conductivity data, and color data of different precious stones in a theoretical manner for comparing with the measured thermal conductivity and electrical conductivity of the testing object.

The method further comprises a step of sending the test result from the microcontroller to an electronic device, such that the test result can be stored digitally, viewed, accessed, and edited via the electronic device.

When the testing object is determined as "other gemstones", the method further comprises the following steps.

(a) Identify the color of the testing object.

(b) Preliminary categorize the testing object based upon the color thereof.

(c) Further measure the thermal conductivity and the electrical conductivity of the testing object.

(d) Comprehensively analyze and process the strengths of the thermal conductivity and the electrical conductivity, and the color of the testing object via the microcontroller in order to identify the testing object.

Accordingly, in the step (b), the microcontroller will compare the measured color of the testing object with the color data in the properties database for classifying the testing object.

It is worth mentioning that the color of the testing object can be identified by human observation, gemstone material identifying instruments, or other gemstone detecting instruments.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 39 is a table illustrating the gemstone color chart according to the above third preferred embodiment of the present invention.

FIG. 44 illustrates the detection probe and its circuit diagram of the multi-functional precious stone testing apparatus according to the above third preferred embodiment of the present invention.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
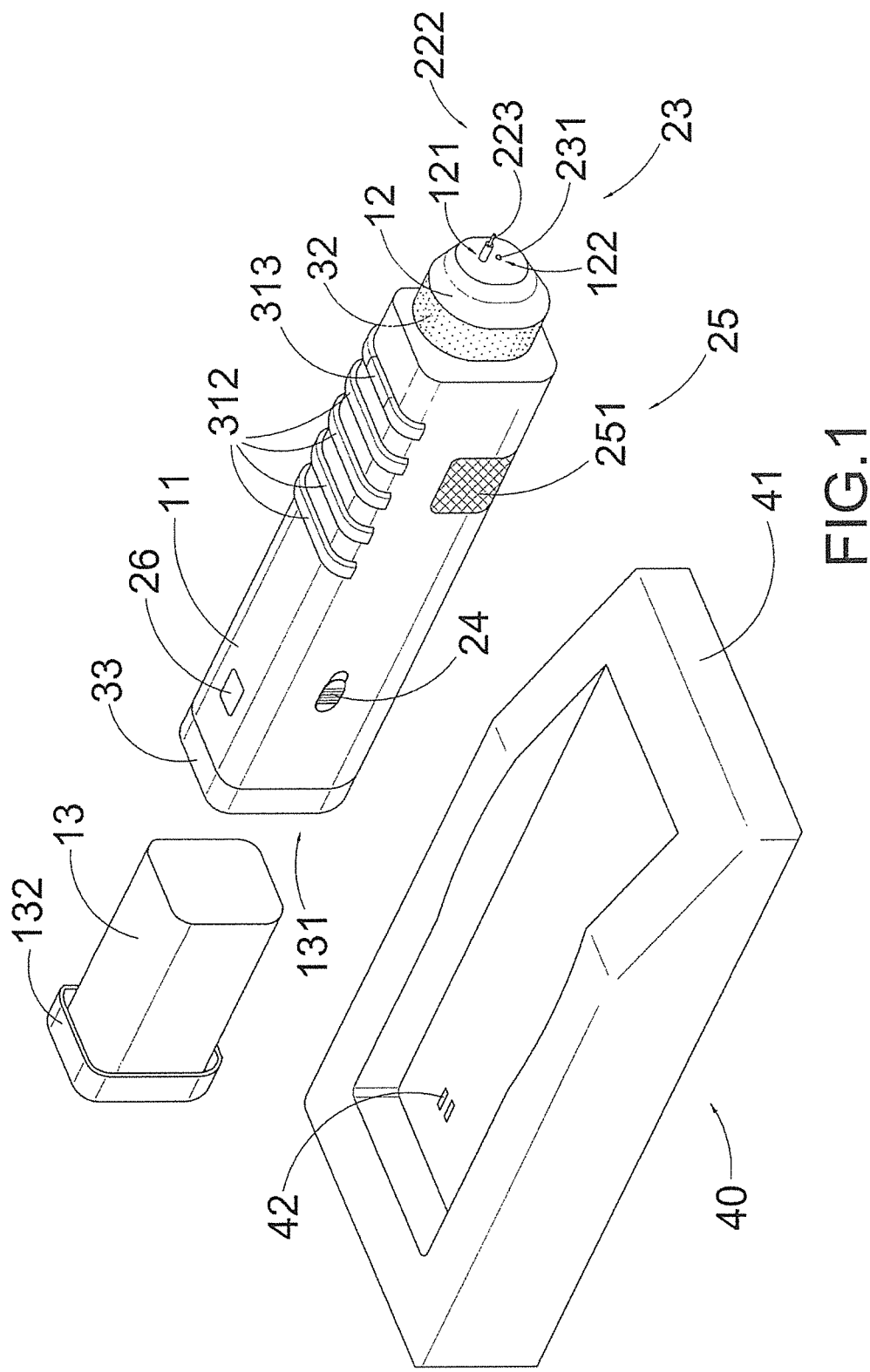
FIG. 1 is a perspective view of a multi-functional precious stone testing apparatus according to a preferred embodiment of the present invention.
Figure 2:
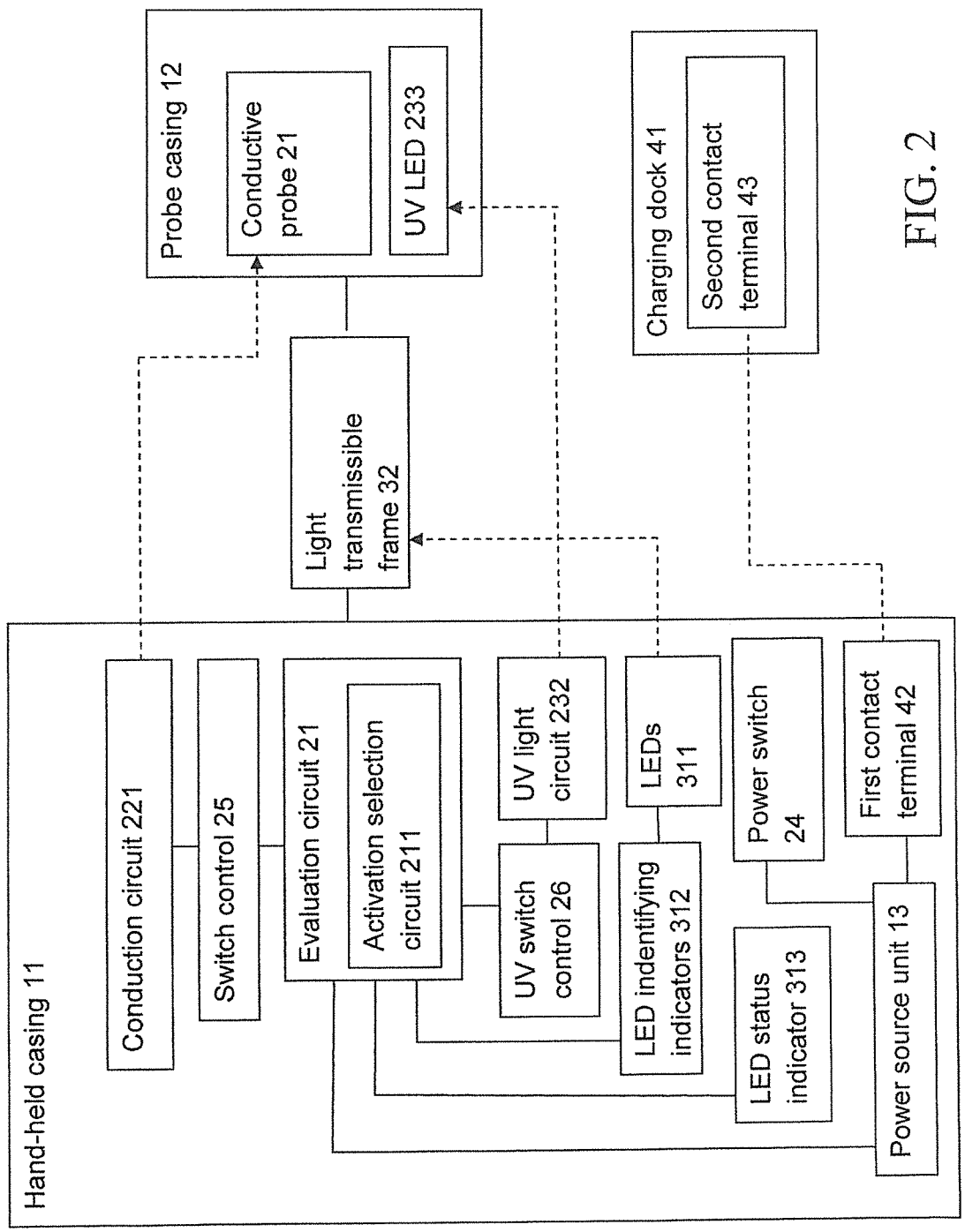
FIG. 2 is a block diagram of the multi-functional precious stone testing apparatus according to the above preferred embodiment of the present invention.

Referring to FIGS. 1 and 2 of the drawings, a multi-functional precious stone testing apparatus according to a preferred embodiment of the present invention is illustrates, wherein the multi-functional precious stone testing apparatus, which is adapted for identifying a testing object as one of diamond, Moissanite, metal, and other stone, comprises a portable housing 10, a testing unit 20, and an indication unit 30.

The portable housing 10 comprises a hand-held casing 11 for receiving a power source unit 13 therein, and a probe casing 12 extended from a front end of the hand-held casing 11. Accordingly, the hand-held casing 11 preferably has a top wall, a bottom wall, and two sidewalls to define an interior cavity within the top wall, bottom wall, and sidewalls, wherein the power source unit 13 is received in the interior cavity of the hand-held casing 11.

The testing unit 20 comprises an evaluation circuit 21 received in the interior cavity of the hand-held casing 11 and electrically linked with the power source unit 13, and a conduction unit 22 operatively linked to the evaluation circuit 21.

The evaluation circuit 21 is a microprocessor electrically coupled at a circuit board with a preloaded evaluation program, wherein the evaluation circuit 21 is arranged to receive a testing signal from the conduction unit 22.

Accordingly, the conduction unit 22 comprises a conduction circuit 221 electrically linked to the evaluation circuit 21 and a conductive probe 222 which is substantially supported by the probe casing 12 and operatively linked to the conduction circuit 221 for determining thermal and/or electrical conductivity when the conductive probe 222 contacts with a testing object.

The conductive probe 222 has a testing end portion 223 extended out of a tip end of the probe casing 12 for contacting the testing object to determine a thermal and/or electrical conductivity of the testing object. Generally, the conductive probe 222 determines a thermal conductivity of a gemstone such as diamond and an electrical conductivity of a moissanite. In other word, the testing signal is sent from the conductive probe 222 to the evaluation circuit 21 such that evaluation circuit 21 will analysis the testing signal in responsive to the conductivity of the testing object in order to classify the testing object.

The testing unit 20 further comprises a UV light source 23 received in the portable housing 10 for generating a UV light beam toward the testing object to measure the fluorescence of the testing object, wherein the UV light source 23 has a light head 231 extended out of the tip end of the probe casing 12 at a position adjacent to the testing end portion 223 of the conductive probe 222.

According to the preferred embodiment, the UV light source 23 comprises a UV light circuit 232 received in the hand held casing 11 to electrically linked with the evaluation circuit 21 and a UV LED 233 adapted for UV light generation, wherein the light head 231 is defined at a head portion of the UV LED 233 protruding out of the tip end of the probe casing 12.

As shown in FIG. 1, the probe casing 12, having a conical shape, has a tip end surface defining a first through slot 121 and a second through slot 122 spacedly formed at the tip end surface, wherein the testing end portion 223 of the conductive probe 222 is extended out of the tip end of the probe casing 12 through the first through slot 121 while the light head 231 of the UV light source 23 is extended out of the tip end of the probe casing 12 through the second through slot 122. Therefore, the testing end portion 223 of the conductive probe 222 is positioned adjacent to the light head 231 of the UV light source 23.

In addition, the protruding length of the testing end portion 223 of the conductive probe 222 is substantially longer than the protruding length of light head 231 of the UV light source 23, such that the testing end portion 223 of conductive probe 222 not only forms a contact point for measuring the thermal and/or electrical conductivity of the testing object but also forms a support point for retaining the light head 231 of the UV light source 23 at a position spacedly apart from the testing object when the testing end portion 223 of the conductive probe 222 contacts with the testing object.

The evaluation circuit 21 comprises an activation selection circuit 211 operatively linked to the conduction unit 22 and the UV light source 23 to selectively operate the conductive probe 222 and the UV light source 23 independently.

Accordingly, the testing unit 20 further comprises a power switch 24 provided at the hand-held casing 11 to electrically link between the power source unit 13 and the evaluation circuit 21 in order to selectively control the evaluation circuit 21 in an on-and-off manner.

The testing unit 20 further comprises a switch control 25 operatively linked to the activation selection circuit 211 to selectively control the conduction unit 22, wherein when the switch control 25 is actuated, the conduction unit 22 is activated through the activation selection circuit 211 to determine the thermal and/or electrical conductivity of the testing object when the conductive probe 222 contacts with the testing object.

Accordingly, the switch control 25 comprises two touch controls 251 provided at the sidewalls of the hand-held casing 11 respectively, wherein the touch controls 251 are activated by a touch of the user. In other words, when the user (right-handed user) holds the hand-held casing 11, the thumb and the index finger of the user will contact at the touch controls 251 respectively in order to activate the conduction unit 22 is activated through the activation selection circuit 211. When one of the touch controls 251 is untouched, the activation selection circuit 211 will automatically deactivate the conduction unit 22 to stop the operation of the conduction unit 22.

The testing unit 20 further comprises a UV switch control 26 operatively linked to the activation selection circuit 211 to selectively control the UV light source 23, wherein when the UV switch control 26 is actuated, the UV light source 23 is activated through the activation selection circuit 211 for UV light generation to measure the fluorescence of the testing object. The UV switch control 26 is preferably provided at the top wall of the hand-held casing 11 such that when the user actuate the UV switch control 26, preferably by depression of the UV switch control 26, the UV light source 23 is activated for UV light generation. It is worth mentioning that the conduction unit 22 and the UV light source 23 are operated independently. In addition, the conduction unit 22 and the UV light source 23 can be operated at the same time.

According to the preferred embodiment, the indication unit 30 comprises a LED light unit 31 received in the hand-held casing 11 and operatively linked to the evaluation circuit 21 for generating a light indicating effect to identify the testing object in responsive to the conductivity of the testing object and for illuminating the testing end portion of the conductive probe 222 during testing.

According to the preferred embodiment, the LED light unit 31 is positioned away from the tip end of the probe casing 12 for preventing heat generated from the LED light unit 31 being transmitted toward the conductive probe 222 to affect an accurate measurement for the conductivity of the testing object.

The LED light unit 31 comprises a plurality of LEDs 311 coaxially supported within the hand-held casing 11 at a position close to the front end thereof, wherein the LEDs 311 are activated for generating light effect when the evaluation circuit 21 is activated. In addition, the evaluation circuit 21 is activated when the conductive probe 222 is in good-contact with the testing object. Therefore, the LEDs 311 will be activated as an indicator for ensuring the testing end portion 223 of the conductive probe 222 being in good-contact with the testing object and as an illuminator for illuminating at the testing end portion 223 of the conductive probe 222 to be contacted with the testing object. However, since the LEDs 311 are positioned away from the testing end portion 223 of the conductive probe 222, the heat from the LEDs 311 will not be transmitted to the conductive probe 222 in order to determine the conductivity of the testing object. It is worth mentioning that the LED light unit 31 is also positioned away from the light head 231 of the UV light source 23 for preventing any interference of the UV light with respect to the illumination light.

Preferably, the LEDs 311 will be activated only when the conduction unit 22 is activated. In other words, the LEDs 311 will be automatically switched off during the operation of the UV light source 23.

The indication unit 30 further comprises a light transmissible frame 32 coupled between the hand-held casing 11 and the probe casing 12, wherein the LEDs 311 of the LED light unit 31 are aligned with the light transmissible frame 32 such that when the evaluation circuit 21 is activated, the LEDs 311 of the LED light unit 31 generate an illumination light to light up the light transmissible frame 32 to diffuse the light from the LEDs 311 for illumination of the testing end portion 223 of the conductive probe 222. In other words, when the conductive probe 222 is in good-contact with the testing object to activate the evaluation circuit 21, the light transmissible frame 32 is lightened up by the LEDs 311 in responsive to the contact between the conductive probe 222 and the testing object.

Figure 3:
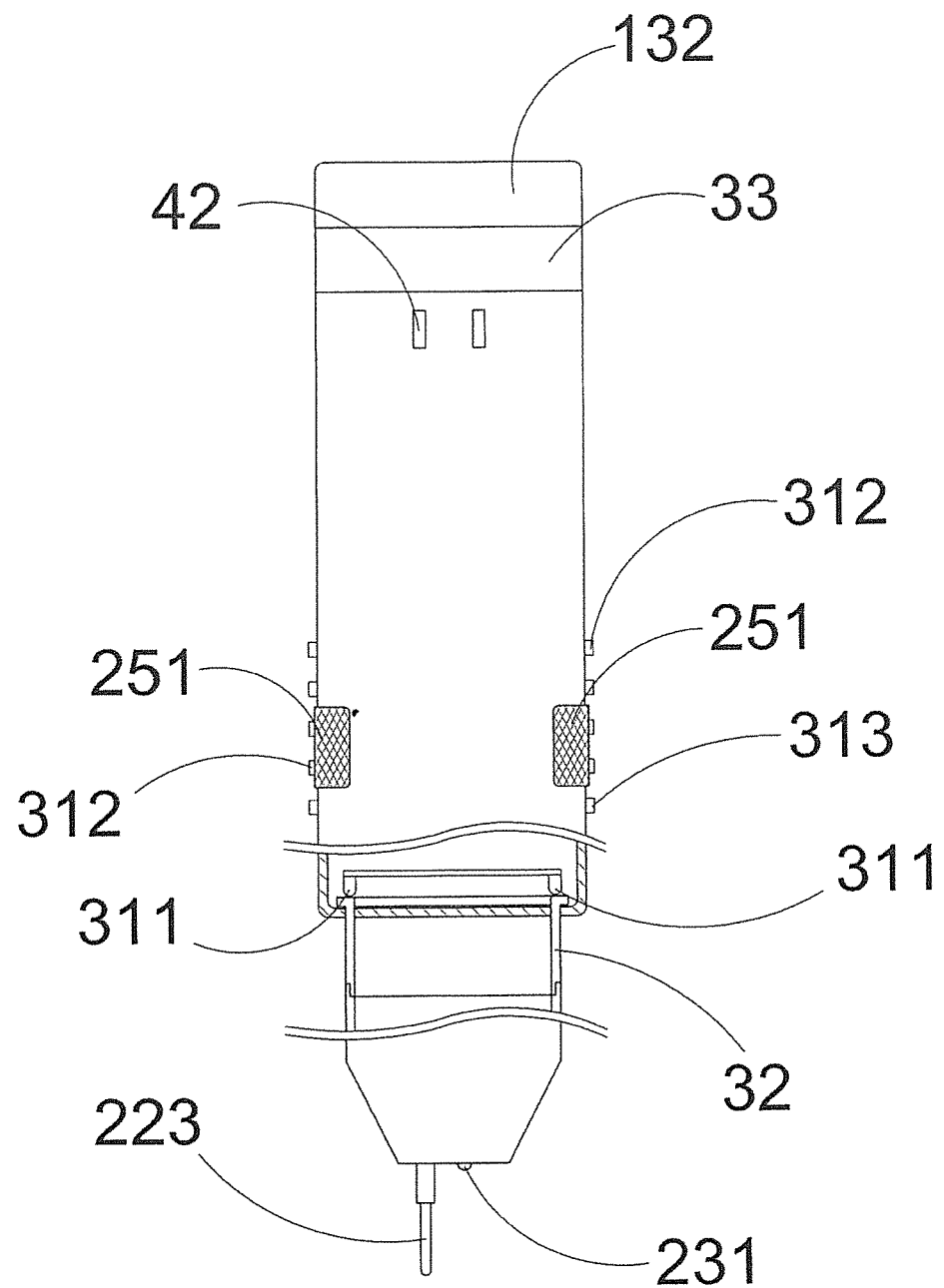
FIG. 3 is a partially sectional view of the multi-functional precious stone testing apparatus according to the above preferred embodiment of the present invention, illustrating the LEDs and the light transmissible frame at the hand-held casing for illumination.

As shown in FIGS. 1 and 3, the light transmissible frame 32 is formed in ring shape encircling around the probe casing 12, wherein the light transmissible frame 32 is detachably coupled between the hand-held casing 11 and the probe casing 12. When the LEDs 311 are activated for light generation, the light transmissible frame 32 forms a 360.degree. illuminated ring to illuminate the testing end portion 223 of the conductive probe 222.

Preferably, the light transmissible frame 32 is made of transparent material such as clear plastic or glass, or translucent material such as frosted plastic or acrylic.

The light transmissible frame 32 has a rear rim extended from the front end of the hand-held casing 11 and a front rim extended to the probe casing 12. In other words, the light transmissible frame 32 forms a neck portion of the portable housing 10 between the hand-held casing 11 and the probe casing 12. Accordingly, the LEDs 311 are coaxially supported at the hand-held casing 11 to align with the rear rim of the light transmissible frame 32, such that when the LEDs 311 are activated for light generation, the light will be transmitted from the rear rim of the light transmissible frame 32 to the front rim thereof so as to light up the light transmissible frame 32.

In addition, the light transmissible frame 32 also forms as a heat isolation frame between the hand-held casing 11 and the probe casing 12 for preventing the heat from the LEDs 311 being transmitted to the conductive probe 222.

The LED light unit 31 further comprises a plurality of LED indentifying indicators 312 spacedly provided on the top wall of the hand-held casing 11 for indicating the testing object to be classified as one of diamond, Moissanite, metal, and other stone. Accordingly, the LED indentifying indicators 312 are operatively linked to the evaluation circuit 21 to show the result of the testing evaluation. The LED indentifying indicators 312 comprises a "diamond" indentifying indicator, "Moissanite" indentifying indicator, "metal" indentifying indicator, and "other stone" indentifying indicator, wherein the respective LED indentifying indicator 312 is activated in responsive to the conductivity of the testing object through the evaluation circuit 21.

Preferably, the LED indentifying indicators 312 are arranged for generating different colors for easy identification. For example, the "diamond" indentifying indicator will generate first color for identifying the testing object as diamond. The "Moissanite" indentifying indicator will generate second color for identifying the testing object as Moissanite. The "metal" indentifying indicator will generate third color for identifying the testing object as metal. The "other stone" indentifying indicator will generate fourth color for identifying the testing object as other stone. In addition, the LEDs 311 will simultaneously change the color to match with the color of the corresponding indentifying indicator 312 when the test is completed. According to the preferred embodiment, different colors are used to represent different test result, such as Blue color representing Diamond, Green color representing Moissanite, Amber (Orange) color representing Metal, and Red color representing Stone.

The LED light unit 31 further comprises a LED status indicator 313 provided at the top wall of the hand-held casing 11 for indicating the status of the evaluation circuit 21. Accordingly, the LED status indicator 313 is arranged for generating different colors in order to indicate the status of the evaluation circuit 21. For example, the LED status indicator 313 will generate red color when the power switch 24 is actuated to start activating the evaluation circuit 21. The LED status indicator 313 will generate amber color to indicate the evaluation circuit 21 being ready for operation. The LED status indicator 313 will generate green color when both fingers are positioned well making a good conductive circuit ready for testing. In operation, firstly, the user turns on the tester, the red wait light illuminates whilst the tester warms up all four testing circuits. Then, the amber light illuminates informing the user to position his or her fingers (such as thumb and index fingers) on to the testing plate positions. Finally, if the user has positioned his or her fingers well and correctly, the green light will illuminates informing the user that he or she is now ready to perform the test. If at any point the amber light comes back on and the green light goes off, it informs the user that he or she does not have a good contact between his or her fingers and the testing plates.

According to the preferred embodiment, the power source unit 13 comprises a battery compartment 131 in the hand-held casing 11 for receiving a battery therein to electrically link with the evaluation circuit 21, and a compartment cover 132 detachably coupled at a rear end of the hand-held casing 11 to enclose the battery compartment 131. The battery can be a replaceable battery replace ably received in the battery compartment 131. Preferably the battery is a rechargeable battery received in the battery compartment 131.

As shown in FIG. 1, the indication unit 30 may further comprise a light indication frame 33 coupled between the rear end of the hand-held casing 11 and the compartment cover 132, wherein the LEDs 311 of the LED light unit 31 generate an illumination light to light up the light indication frame 33 corresponding to the light transmissible frame 32. Therefore, the light transmissible frame 32 and the light indication frame 33 are formed at the front and rear ends of the hand-held casing 11. It is worth mentioning that due to the preference of the buyers, it is an option to have just the light transmissible frame 32 or to have both the light transmissible frame 32 as well as the light indication frame 33 as illustrated in the FIG. 1 according to the preferred embodiment.

Accordingly, the multi-functional precious stone testing apparatus further comprises a charging arrangement 40 for electrically charging the power source unit 13, wherein the charging arrangement 40 comprises a charging dock 41 for electrically linking to a power supply, a first contact terminal 42 provided at the portable housing 10 to electrically link with the power source unit 13, and a second contact terminal 43 provided at the charging dock 41 and arranged in such a manner that when the portable housing 10 docks at the charging dock 41, the first contact terminal 42 contacts with the second contact terminal 43 to electrically charge the power source unit 13.

In order operate the multi-functional precious stone testing apparatus, the user is able to switch on the power switch 24 in order to warm up the evaluation circuit 21, wherein the LED status indicator 313 will generate red color during the warm up time. Once the LED status indicator 313 generates amber color, the evaluation circuit 21 is ready for operation. The user is able to hold the hand-held casing 11 and to contact the touch controls 251 by the thumb and the index finger respectively to activate the conduction unit 22. Once the testing end portion 223 of the conductive probe 222 contacts with the testing object, the LED status indicator 313 will generate green color to indicate the proper contacts of the touch controls 251 and the good contact between the testing end portion 223 of the conductive probe 222 and the testing object. Then, the evaluation circuit 21 will classify the testing object in responsive to the conductivity thereof. Correspondingly, one of the LED indentifying indicators 312 will be activated for light indication by the evaluation circuit 21.

The user is also able to measure the fluorescence of the testing object via the UV light source 23. The user is able to actuate the UV switch control 26 in order to activate the UV light source 23 for UV light generation. It is worth mentioning that the light head 231 of the UV light source 23 is spaced apart from the testing object since the testing end portion 223 of the conductive probe 222 contacts with the testing object.

Figure 4:
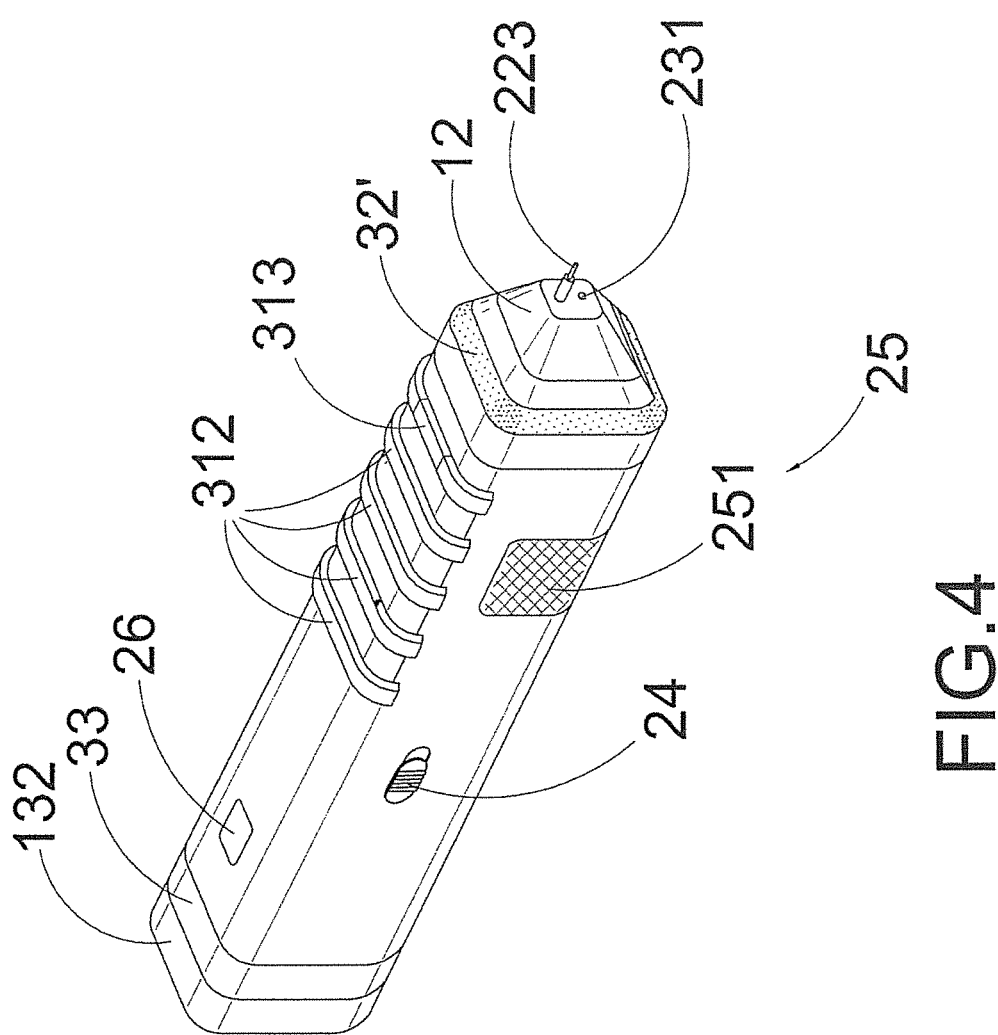
FIG. 4 illustrates an alternative mode of the light transmissible frame of the multi-functional precious stone testing apparatus according to the above preferred embodiment of the present invention.

FIG. 4 illustrates an alternative mode of the light transmissible frame 32' wherein the light transmissible frame 32' is formed in ring shape integrally formed at the front end of the hand-held casing 11 to encircle around the probe casing 12. The LEDs 311 of the LED light unit 31 are aligned with the light transmissible frame 32' such that when the evaluation circuit 21 is activated, the LEDs 311 of the LED light unit 31 generate an illumination light to light up the light transmissible frame 32' to diffuse the light from the LEDs 311 for illumination of the testing end portion 223 of the conductive probe 222.

Figure 5:
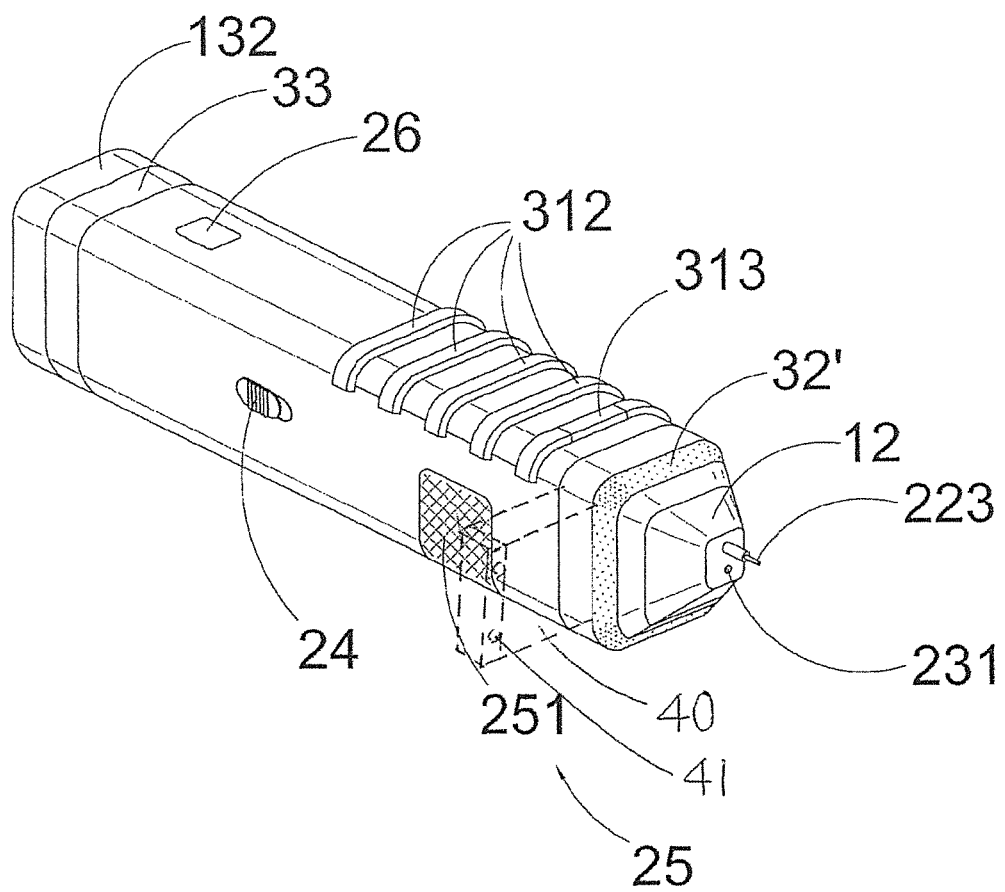
FIG. 5 illustrates a first alternative mode of the multi-functional precious stone testing apparatus according to the above preferred embodiment of the present invention.

FIG. 5 illustrates another alternative mode of the preferred embodiment of the present invention, wherein a magnifying lens 40 can be mounted to the testing apparatus of the present invention, in foldable or slidable manner, at a predetermined position adapted for the user to view the conductive probe 222 to magnify the conductive probe 222 and the object being tested. The magnifying lens 40 may further comprise at least a LED 41 for illuminating the area around the magnifying lens 40 during magnifying the testing operation.

Figure 6:
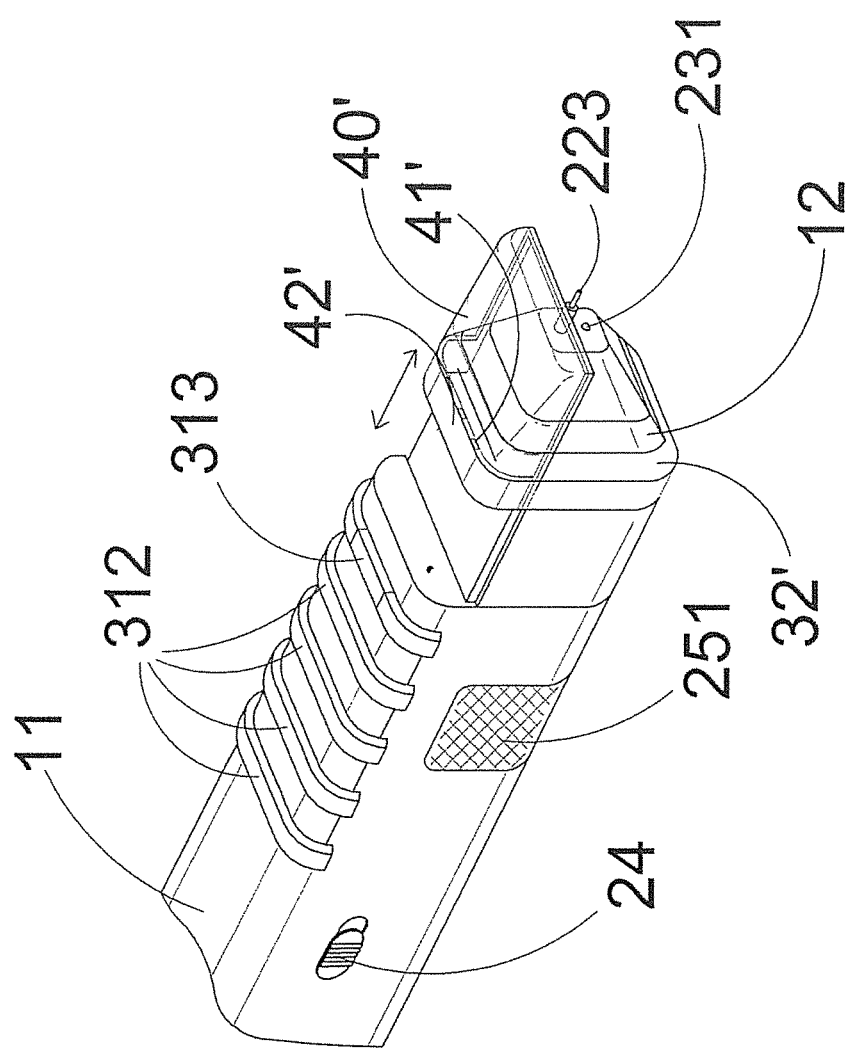
FIG. 6 illustrates a second alternative mode of the multi-functional precious stone testing apparatus according to the above preferred embodiment of the present invention.

FIG. 6 illustrates another alternative mode of the preferred embodiment of the present invention, wherein the magnifying lens 40' is movably coupled at the hand-held casing 11 at a position close to the front end thereof. The magnifying lens 40' is adapted to slidably move between a folded position and an unfolded position, wherein at the folded position, the magnifying lens 40' is rearwardly slid on the outer surrounding surface of the hand-held casing 11, preferably at the top wall thereof, and at the unfolded position, the magnifying lens 40' is frontwardly slid toward the conductive probe 22 to magnify the conductive probe 222 and the object being tested. A lens frame 42' with one or more LED light illuminators 41' can be slidably mounted at the top wall of the hand-held casing 11 to hold the magnifying lens 40' in position. The LED light illuminator 41' of the lens frame 42' is electrically linked to the power source unit 13 via a positioning contact switch that when the magnifying lens 40' is moved at the folded position, the LED light illuminator 41' of the lens frame 42' is electrically disconnected to the power source unit 13 and when the magnifying lens 40' is moved at the unfolded position, the LED light illuminator 41' of the lens frame 42' is electrically connected to the power source unit 13.

Figure 7:
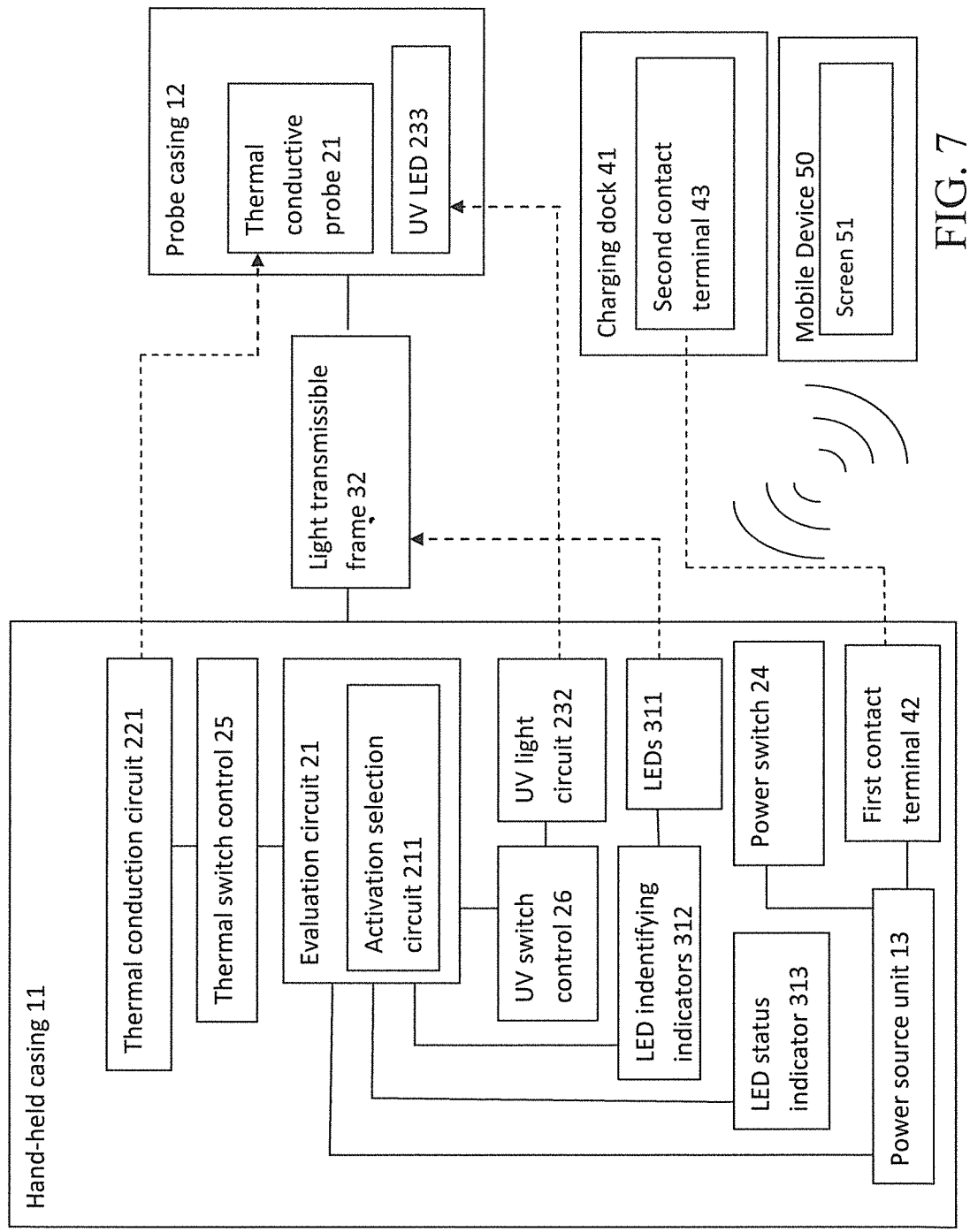
FIG. 7 is a block diagram of the multi-functional precious stone testing apparatus equipped and configured with a mobile device through a wireless network according to the above preferred embodiment of the present invention.
Figure 8:
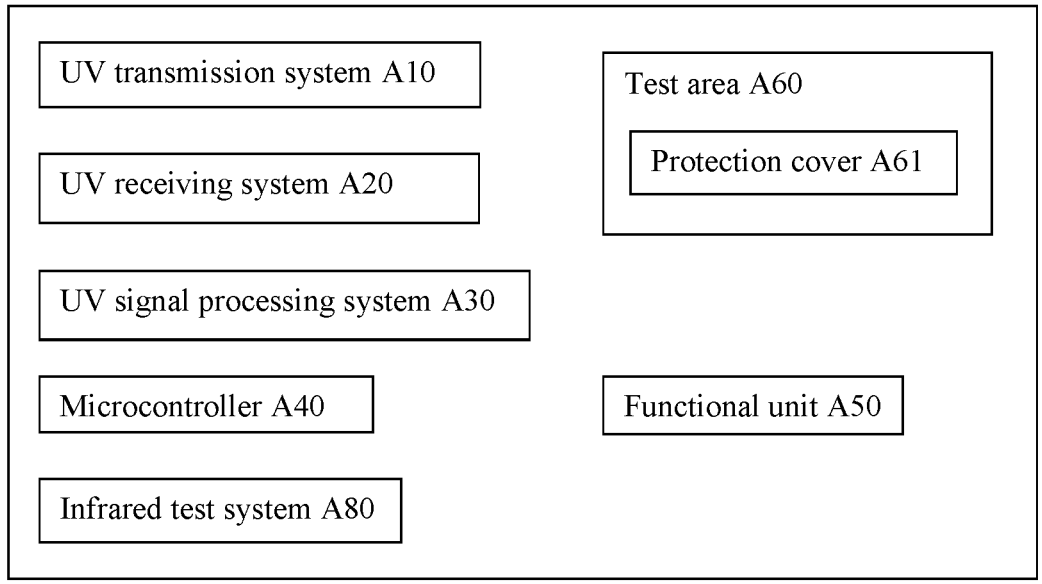
FIG. 8 is a block diagram illustrating the testing apparatus according to a second preferred embodiment of the present invention.
Figure 9:
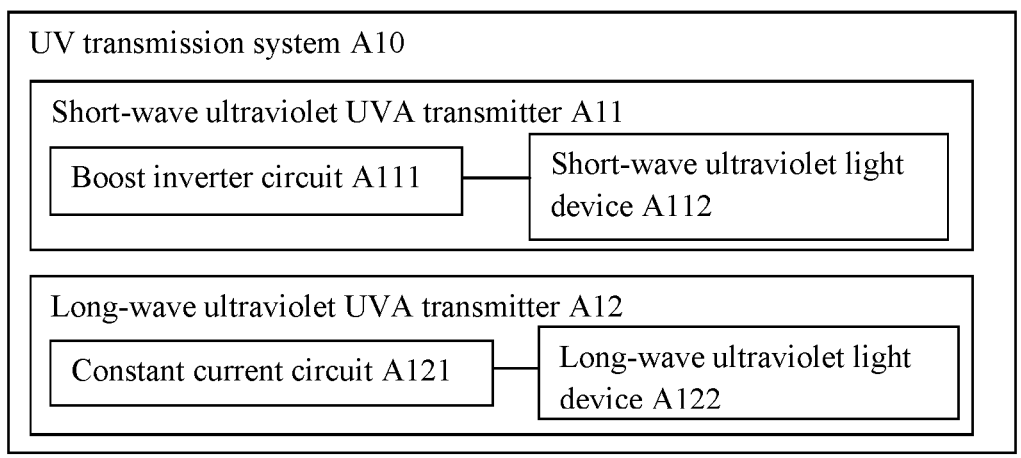
FIG. 9 is a block diagram illustrating the UV transmission system of the testing apparatus according to the above second preferred embodiment of the present invention.
Figure 10:
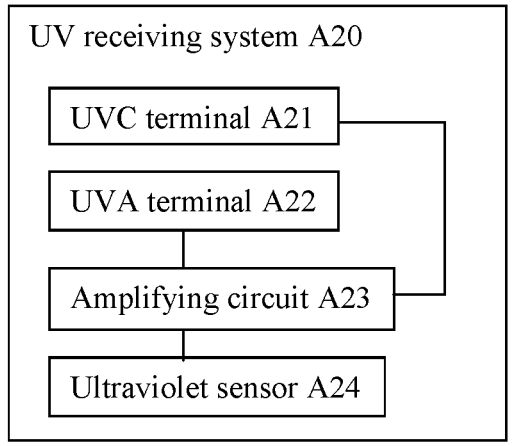
FIG. 10 is a block diagram illustrating the UV receiving system of the testing apparatus according to the above second preferred embodiment of the present invention.
Figure 11:
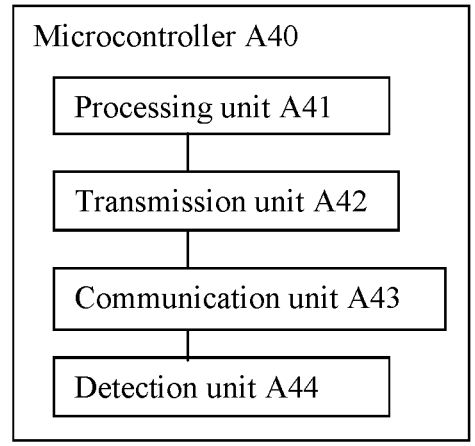
FIG. 11 is a block diagram illustrating the microcontroller of the testing apparatus according to the above second preferred embodiment of the present invention.
Figure 12:
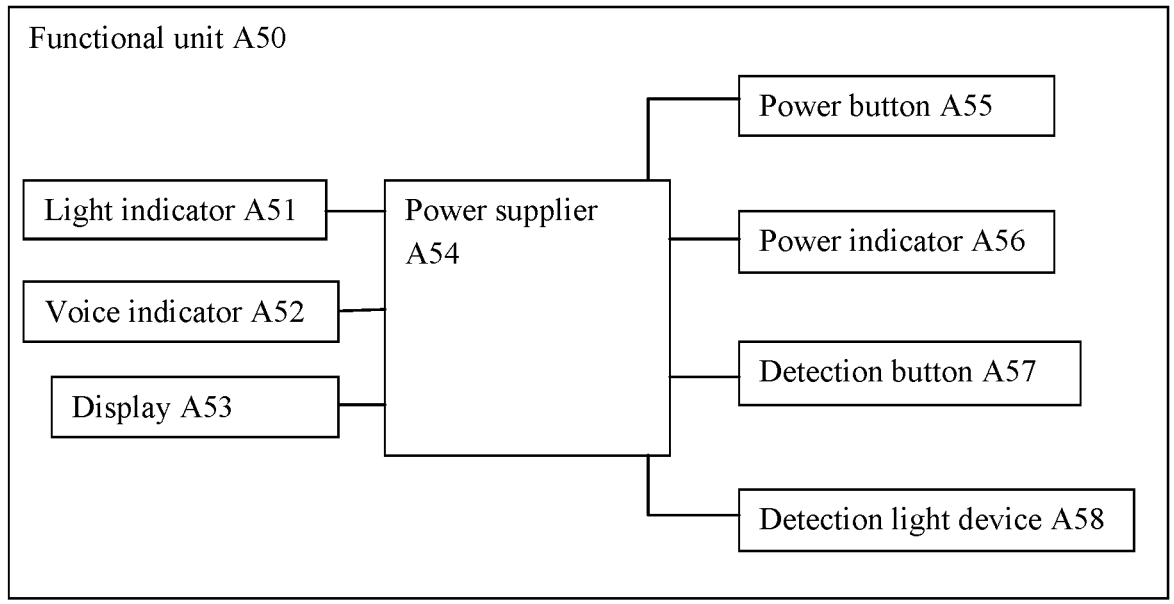
FIG. 12 is a block diagram illustrating the functional unit of the testing apparatus according to the above second preferred embodiment of the present invention.

It is worth mentioning that, referring to FIG. 7, the multi-functional precious stone testing apparatus according the preferred embodiment as shown in FIGS. 1-6 of the present invention may further include a communication module linked with, but not limited to, the evaluation circuit 21, UV light circuit 232, UV switch control 26, LED indentifying indicator 312, LED status indicator 313, power source unit 13, thermal conductive probe 21, thermal switch control 25, and/or thermal conduction circuit 221, to be equipped and configured with a mobile device 50, such as mobile phone, tablet, notebook, and etc., of the user which has been downloaded with a corresponding APP through a wireless network, such as Internet, Wi-Fi, Bluetooth, and etc., so as to illustrate the test results, indicating the testing object to be classified as one of diamond, Moissanite, metal and other stone, as well as acting as the indication unit 30, if required, so that the user may simply access the test result from his or her paired mobile device placed at where it is convenient for the user to view. Accordingly, it would be an alternative mode of the multi-functional precious stone testing apparatus of the present invention that by equipping and configuring with the APP of the mobile device of the user, the mobile device can substitute the indication unit 30 of the present invention. In other words, the mobile device 50 paired with the multi-functional precious stone testing apparatus can be functioned as the indication device 30 which is wirelessly linked and configured with the evaluation circuit 21 through the wireless network for generating an indicating effect to identify the testing object in responsive to the conductivity of the testing object and for illuminating the testing end portion of the conductive probe 222 during testing, wherein the indication unit 30 is configured that when the conductive probe 222 is in contact with the testing object to activate the evaluation circuit 21, the indication unit 30 generates a testing signal in responsive to the contact between the conductive probe and the testing object to identify the testing object as diamond by the thermal conductivity and as moissanite by the electrical conductivity.

According, each testing object has its own characteristics, including their physical properties and chemical properties. The use of characteristics to identify the precious stone is natural or lab-grown diamond or other stones is important not only for protecting the consumers but also for the gem dealers.

Since the major component of Mosissanite is silicon carbide which is similar to diamond, many people are unable to distinguish between the natural diamond and Moissanite. Therefore, it is always a doubt for the consumers to buy Moissanite as the replication of diamond in higher price.

Accordingly, UV fluorescence is an effective way to distinguish natural diamonds and synthetic diamonds is very effective since the colors of natural diamonds and synthetic diamonds under UV fluorescence are different and the light distributions of natural diamonds and synthetic diamonds are significant different. Accordingly, natural diamonds can absorb short-wave ultraviolet light (wavelength 254 nm, UVC), and are in blue fluorescence under the long-wave ultraviolet light. On the other hand, HPHT/CVD Diamonds (synthetic diamond) has no fluorescence under short-wave ultraviolet light and has yellow green, orange and yellow fluorescence under long-wave ultraviolet light. Therefore, under ultraviolet light, natural diamonds and synthetic diamonds will show different colors. The present invention provides a testing apparatus using this principle to identify or distinguish colorless natural diamonds and synthetic diamonds.

Accordingly, the long-wave UV light (wavelength 365 nm, UVA) can penetrate through natural diamonds and can be absorbed by Moissanite. Under the UV light, diamonds and moissanite will show different colors. The testing apparatus uses this principle to identify or distinguish colorless natural diamonds and Moissanite.

Each gem stone has its own specific infrared spectrum. The testing apparatus uses the infrared spectrum to accurately determine the testing object.

In particular, the testing apparatus of the present invention can identify the testing object as natural diamond, synthetic diamond, or Moissanite based on their own characteristics.

Referring to FIGS. 8 to 12 and 16, the testing apparatus of the present invention comprises a UV transmission system A10, a UV receiving system A20, a UV signal processing system A30, a microcontroller A40, a functional unit A50, and an infrared test system A80. The UV transmission system A10 is operatively linked to the UV receiving system A20 that the UV receiving system A20 is arranged to receive ultraviolet light from the UV transmission system A10 through the testing object. The UV receiving system A20 is operatively linked to the UV signal processing system A30 for collecting UV data after the UV receiving system A20 receives the ultraviolet light. The microcontroller A40 is operatively linked to the UV signal processing system A30 and the functional unit A50, wherein the microcontroller A40 processes the UV data to determine the strength or intensity of the ultraviolet light received by the UV receiving system A20 so as to generate a test result, and sends the test result to the functional unit A50.

Figure 21:
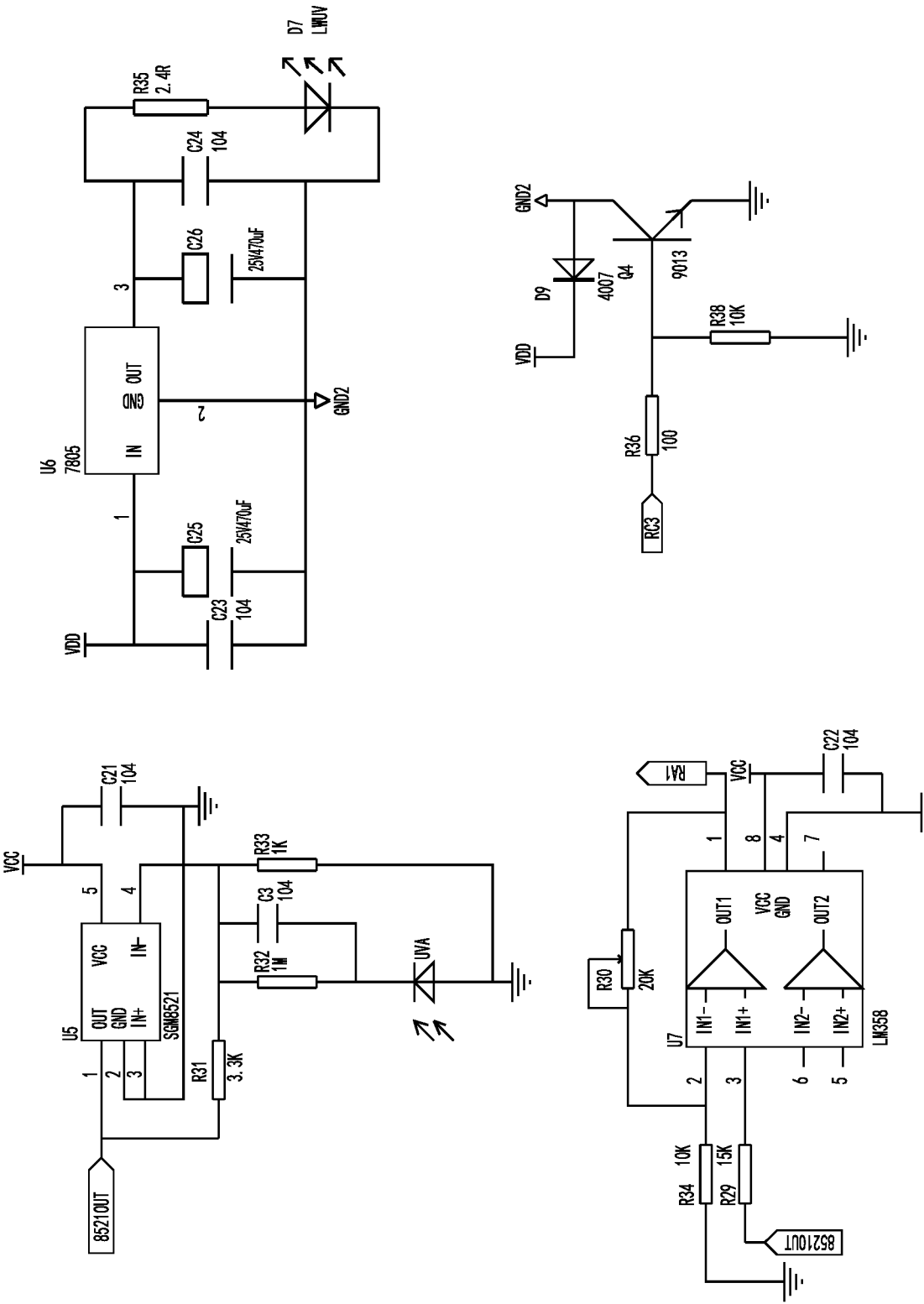
FIG. 21 is a circuit diagram of the long-wave ultraviolet detection system of the testing apparatus according to the above second preferred embodiment of the present invention.
Figure 22:
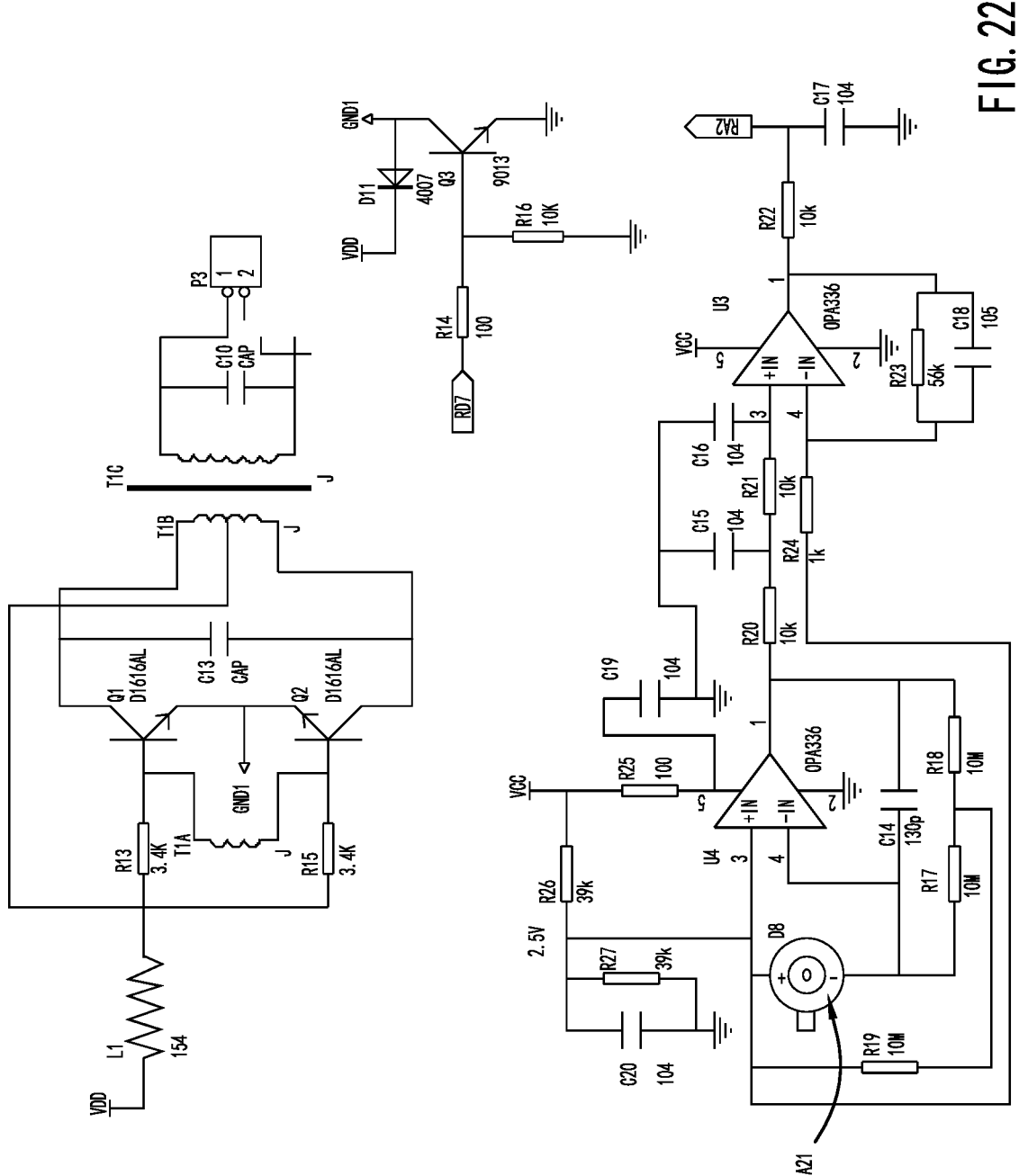
FIG. 22 is a circuit diagram of the short-wave ultraviolet detection system of the testing apparatus according to the above second preferred embodiment of the present invention.

In particular, the UV transmission system A10 comprises a short-wave ultraviolet UVA transmitter A11 and a long-wave ultraviolet UVA transmitter A12 for emitting short-wave ultraviolet (UVC) and long-wave ultraviolet (UVA) to penetrate the testing object, wherein the UV receiving system A20 receives the short-wave ultraviolet and long-wave ultraviolet after the penetration through the testing object. The short-wave ultraviolet UVC transmitter A11 comprises a boost inverter circuit A111 and at least one short-wave ultraviolet light device A112 connected to the boost inverter circuit A111. The boost inverter circuit A111 is arranged to boost the lithium battery voltage above 200V AC to activate the short-wave ultraviolet light device A112 for generating the short-wave ultraviolet UVC. The long-wave ultraviolet UVA transmitter A12 comprises a constant current circuit A121 and at least one long-wave ultraviolet light device 122 connected to the constant current circuit A121. The constant current of the constant current circuit A121 is preferably set at 5V which generates 300 mA current to activate the long-wave ultraviolet light device A122. In other words, the short-wave ultraviolet light device 112 and the long-wave ultraviolet light device A122 are activated to emit UVC and UVA respectively. FIGS. 21 and 22 illustrates the long-wave ultraviolet detection circuit and the short-wave ultraviolet detection circuit respectively.

The UV receiving system A20 comprises a UVC terminal A21, a UVA terminal A22, at least an amplifying circuit A23, and at least an ultraviolet sensor A24. The UVC terminal A21 is operatively connected to the short-wave ultraviolet light device A112, and is operatively connected to the amplifying circuit A23 and the boost inverter circuit A111. The UVA terminal A22 is operatively connected to the long-wave ultraviolet light device A122, and is operatively connected to the amplifying circuit A23 and the constant current circuit A121. The ultraviolet sensor A24, such as a Hall sensor, is operatively linked to the UVC terminal A21 and the UVA terminal A22. The amplifying circuit A23 is operatively connected to the UV receiving system A20 and the UV signal processing system A30, such that the UV receiving system A20 can receive the ultraviolet light from the UV transmission system A10 and can transmit the UV signal to the UV signal processing system A30. The UV signal processing system A30 will collect the strength/intensity of ultraviolet light and will preliminary process the UV data before it is sent to the microcontroller A40. After the data processing of the microcontroller 40, the test result will be generated.

It is worth mentioning that the ultraviolet sensor A24 receives the UV signal which is amplified by the amplifying circuit A23 before the UV signal is sent to UV signal processing system A30 and/or the microcontroller A40 for generating the test result in response to the UV intensity. Preferably, the ultraviolet sensor A24 comprises a short-wave ultraviolet sensor and a long-wave ultraviolet sensor.

Figure 23:
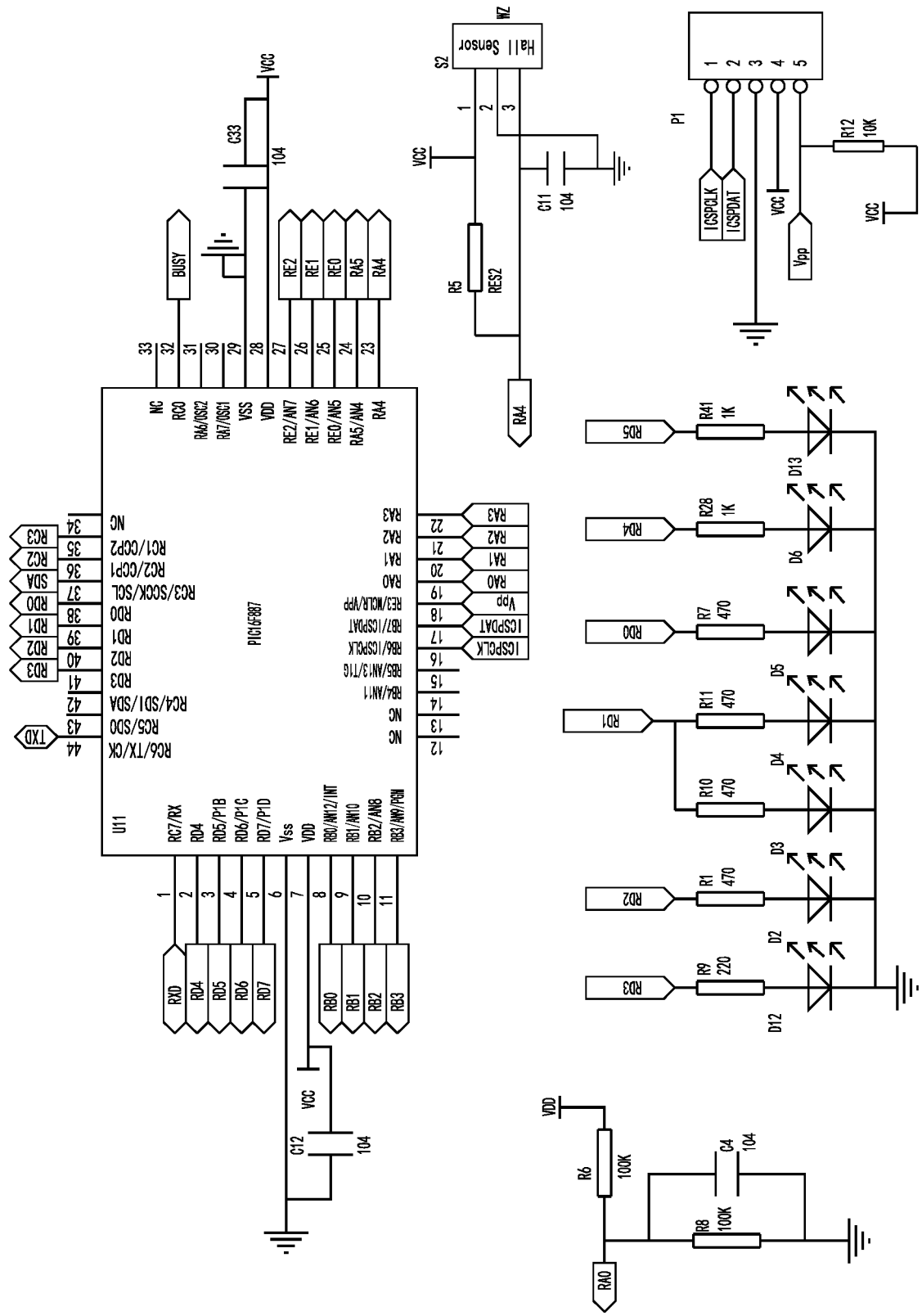
FIG. 23 is a circuit diagram of the microcontroller of the testing apparatus according to the above second preferred embodiment of the present invention.

The microcontroller A40 comprises a processing unit A41 and a transmission unit A42 operatively linked to the processing unit A41. According to the preferred embodiment, the processing unit A41 is operatively linked to the UV receiving system A20. In particular, the processing unit A41 is operatively linked to the ultraviolet sensor A24 for processing and analyzing the UV intensity from the ultraviolet sensor A24 and for generating the test result being sent to the transmission unit A42. Preferably, the UV signal processing system A30 can be integrated with the processing unit A41 to form an integrated signal processing unit. It is appreciated that the UV signal processing system A30 and the processing unit A41 are two individual components. It is worth mentioning that the UV signal processing system A30 will collect the UV intensity from the ultraviolet sensor A24 and will sent the UV data to the processing unit A41 for further analyzing and processing in order to accurately identify the testing object. FIG. 23 is a circuit diagram of the microcontroller.

It is worth mentioning that the UV signal processing system A30 can be an independent component connected to the microcontroller A40, wherein the UV signal processing system A30 and the microcontroller A40 are corporative to process the UV data. Likewise, the UV signal processing system A30 can be integrated with the microcontroller 40 as the an integrated signal processing unit to process the UV data.

Figure 24:
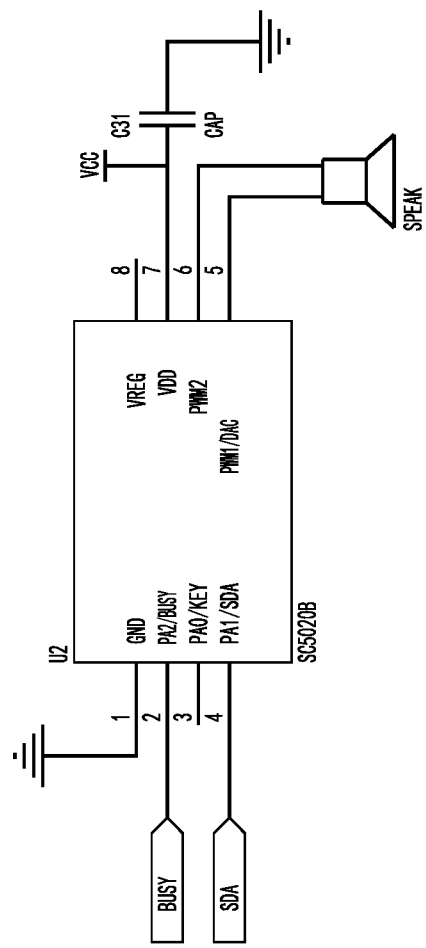
FIG. 24 is a circuit diagram of the voice indicator of the testing apparatus according to the above second preferred embodiment of the present invention.
Figure 28:
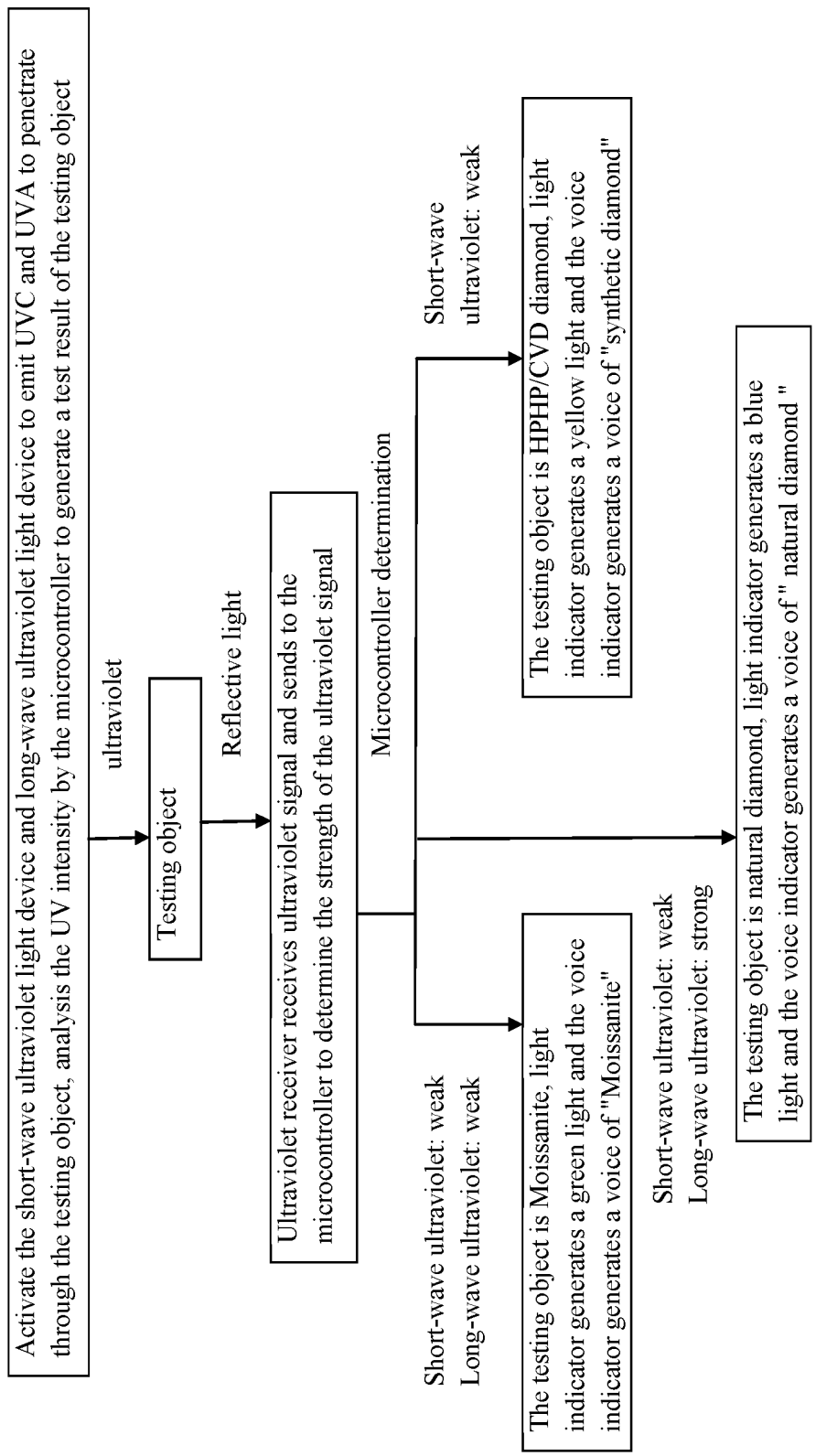
FIG. 28 is a flow diagram illustrating the ultraviolet testing operation of the multi-functional precious stone testing apparatus according to the above second preferred embodiment of the present invention.

The functional unit A50 comprises a light indicator A51, a voice indicator A52, a display A53, and a power supplier A54, wherein the light indicator A51, the voice indicator A52, and the display A53 are operatively linked to the microcontroller A40. Accordingly, once the test result is generated, a test result signal is generated by the microcontroller A40 and is sent to the light indicator A51, the voice indicator A52, and the display A53. Therefore, the test result is sent to identify the testing object via a light indication signal from the light indicator A51, as shown in FIG. 28. For example, the light indicator will generate a blue light when the testing object is identified as natural diamond. Then, the light indicator will generate a yellow light when the testing object is identified as synthetic diamond. The, the light indicator will generate a green light when the testing object is identified as Moissanite. Accordingly, the voice indicator will generate a voice of "natural diamond", "synthetic diamond" or "Moissanite" in response to the test result signal sent from the microcontroller A40. The display A53 will display the image or character of "natural diamond", "synthetic diamond" or "Moissanite" in response to the test result signal sent from the microcontroller A40. Preferably, the light indicator A51 comprises at least a LED for generating different colors for indicating the identification of the testing object in response to the test result signal sent from the microcontroller A40. FIG. 24 illustrates a circuit diagram of the voice indicator.

Accordingly, the light indicator A51, the voice indicator A52, and the display A53 are operatively linked to the transmission unit A42 which sends the test result signal to the light indicator A51, the voice indicator A52, and the display A53.

Figure 27:
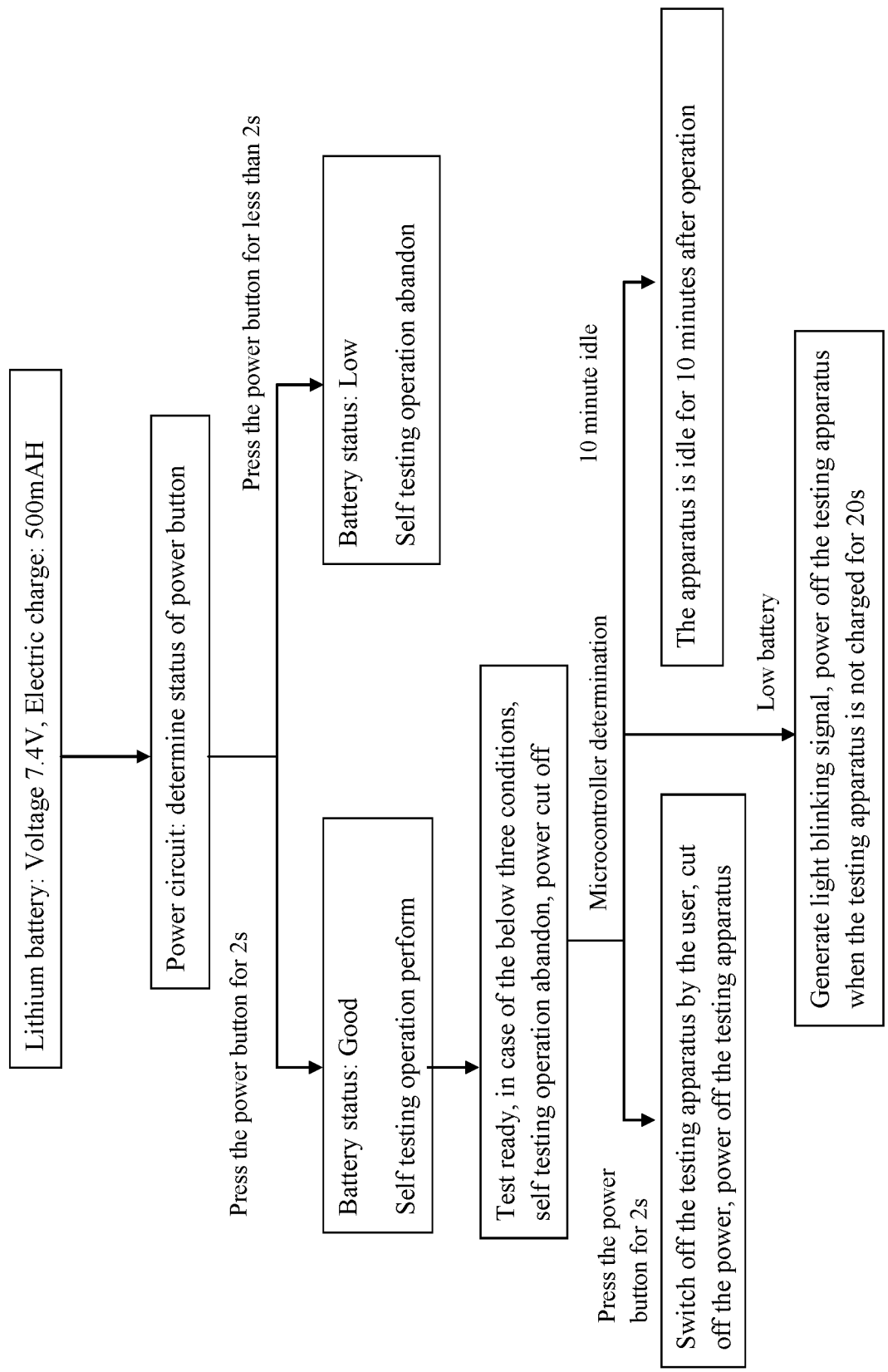
FIG. 27 is a flow diagram illustrating the power supplying of the multi-functional precious stone testing apparatus according to the above second preferred embodiment of the present invention.

The functional unit A50 further comprises a power button A55 and a power indicator A56, wherein the power button A55 is operatively connected to the power supplier A54 and the microcontroller A40. The power supplier A54 is operatively connected to the power indicator A56 and other components for supplying power thereto. In other words, once the power button A55 is actuated, all the components are powered up in a working mode and are ready for testing operation. Once the operation is completed, the power button A55 is then actuated to shut down all the components. Accordingly, the power supplier A54 is preferably a battery assembly which comprises a rechargeable battery or replaceable battery. Alternatively, the power supplier A54 can be a power terminal for connecting to an external electric socket. Preferably, the power supplier A54 comprises the rechargeable battery, wherein when the testing apparatus of the present invention is switched on via the power button A55, all the components thereof will be powered up. In case of low battery, the power indicator A56 will generate a low battery signal, such as a light blinking signal in red color, such that the rechargeable battery of the power supplier A54 should be recharged before it is used, as shown in FIG. 27.

Figure 25:
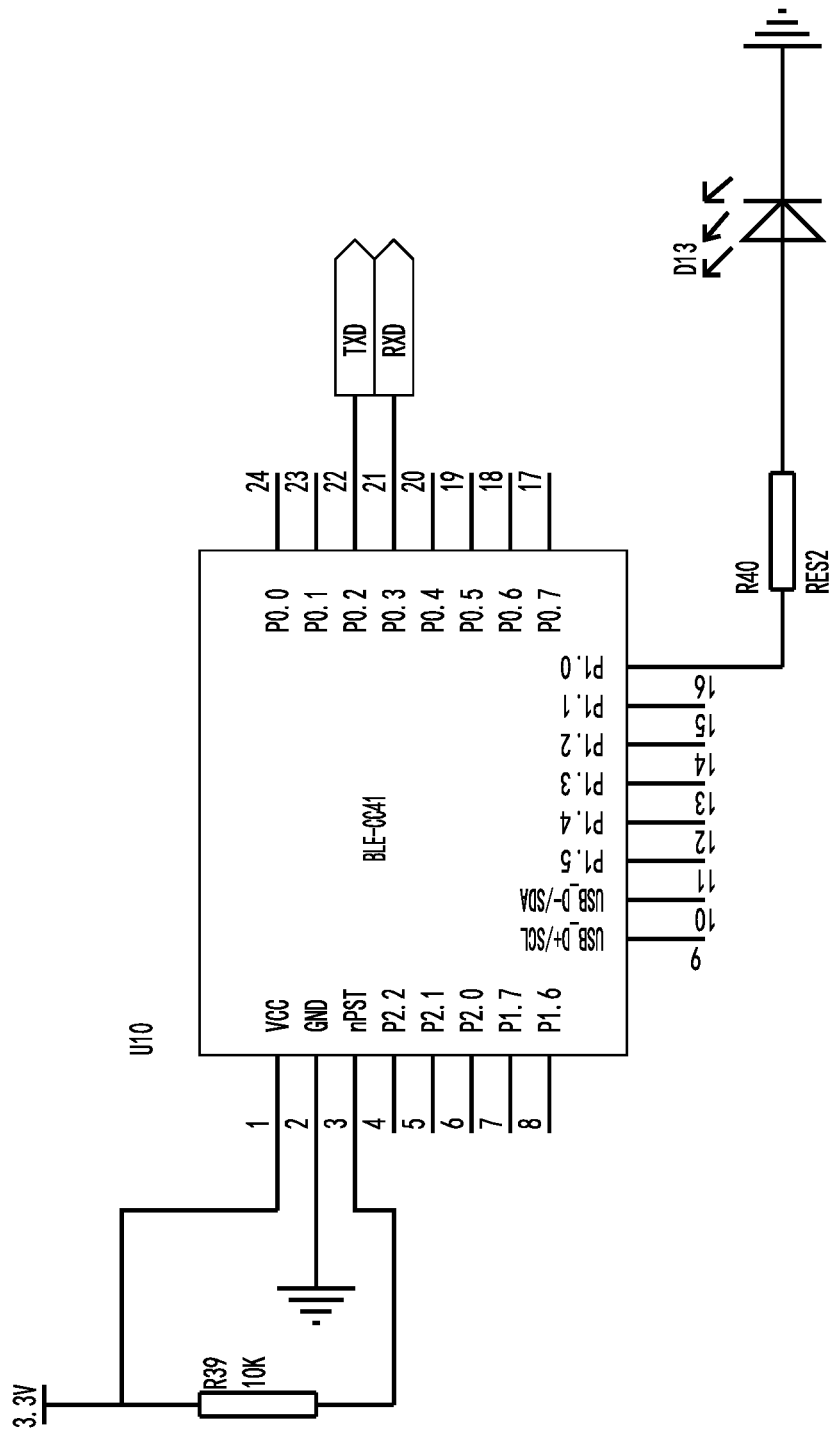
FIG. 25 is a circuit diagram of the communication unit of the testing apparatus according to the above second preferred embodiment of the present invention, illustrating the Bluetooth communication connection.
Figure 26:
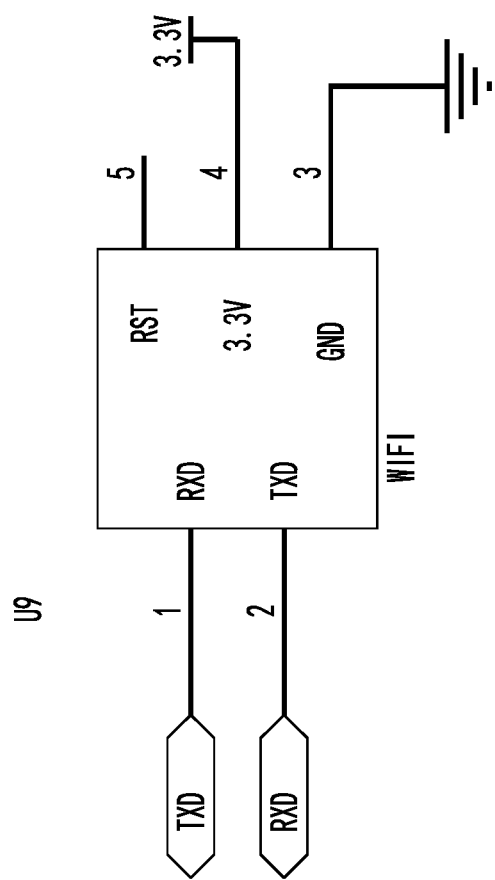
FIG. 26 is a circuit diagram of the communication unit of the testing apparatus according to the above second preferred embodiment of the present invention, illustrating the WiFi communication connection.
Figure 30:
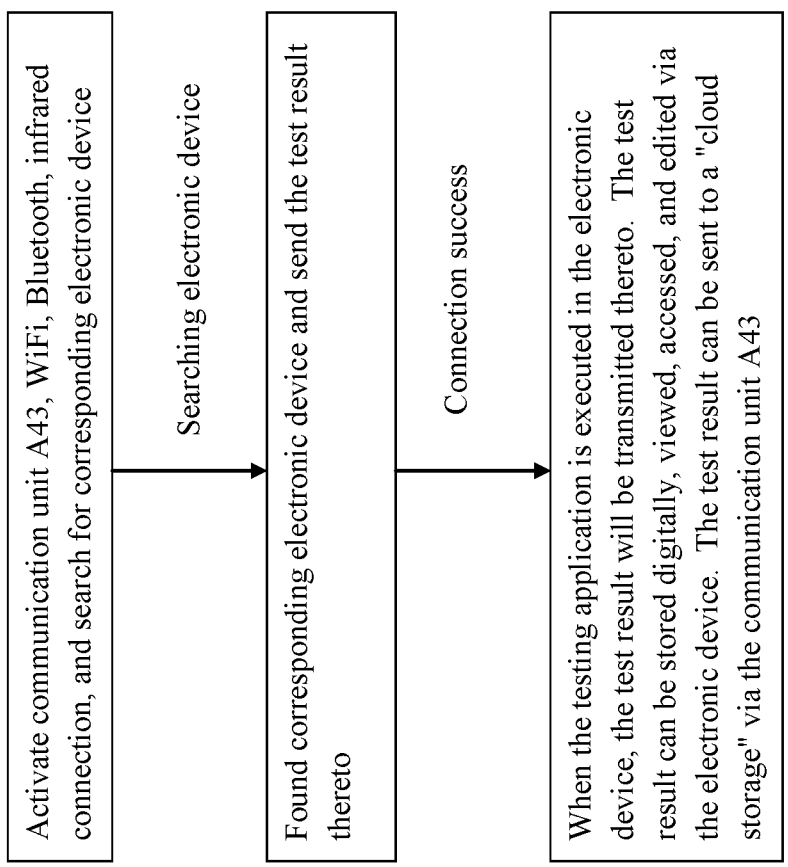
FIG. 30 is a flow diagram illustrating the wireless connection of the electronic device via the communication unit of the multi-functional precious stone testing apparatus according to the above second preferred embodiment of the present invention.
Figure 31:
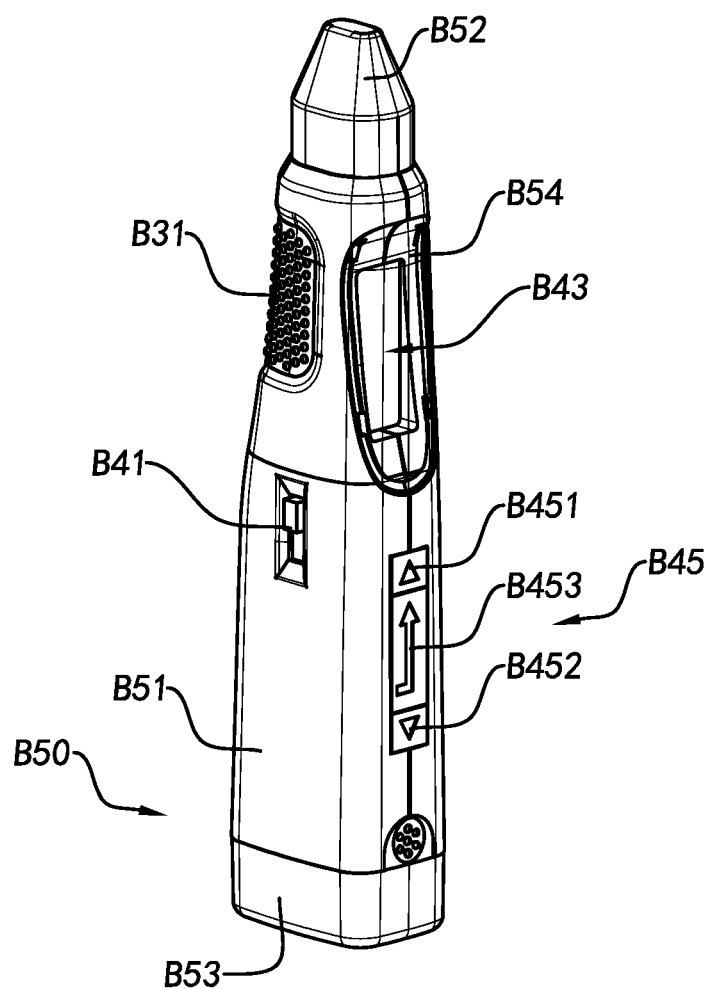
FIG. 31 is a perspective view of a multi-functional precious stone testing apparatus according to a third preferred embodiment of the present invention.
Figure 32:
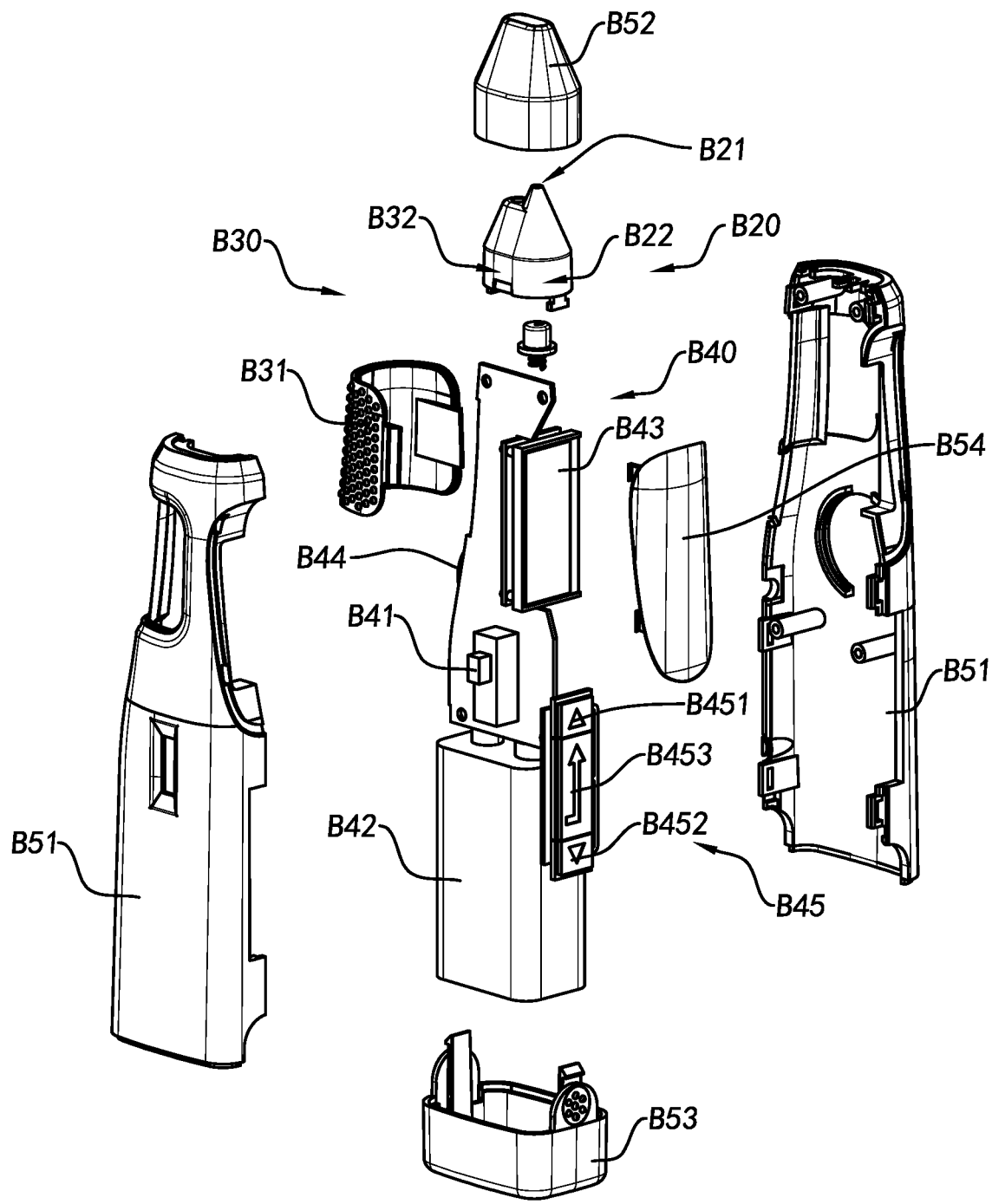
FIG. 32 is an exploded front perspective view of the multi-functional precious stone testing apparatus according to the above third preferred embodiment of the present invention.
Figure 33:
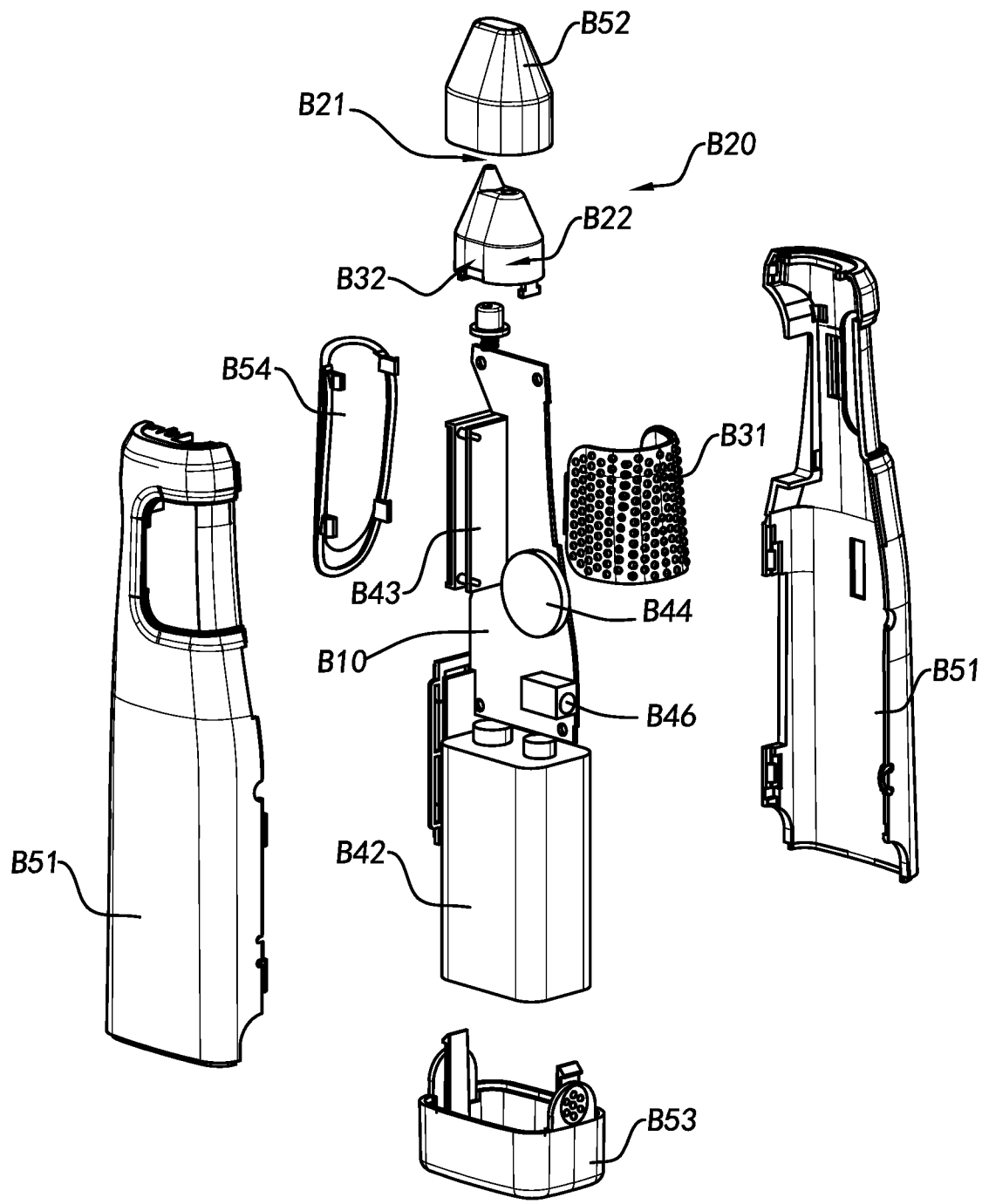
FIG. 33 is an exploded rear perspective view of the multi-functional precious stone testing apparatus according to the above third preferred embodiment of the present invention.
Figure 34:
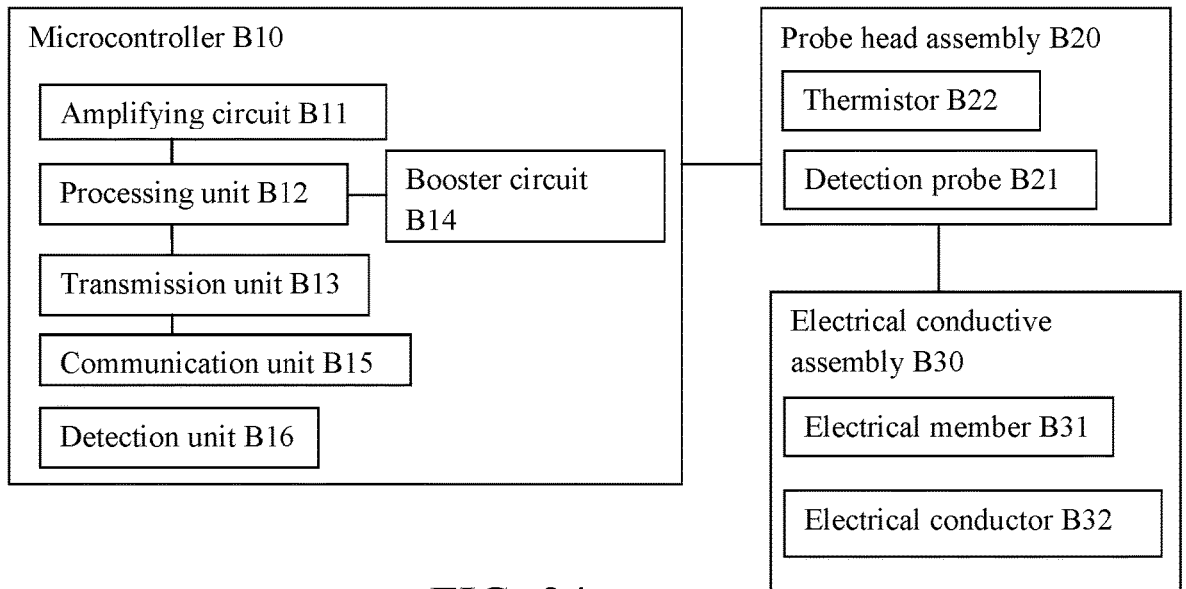
FIG. 34 is a block diagram of the multi-functional precious stone testing apparatus according to the above third preferred embodiment of the present invention.

The microcontroller A40 further comprises a communication unit A43 operatively linked to the transmission unit A42 to transmit the test result to the functional unit A50 and at the same time to transmit the test result to an external electronic device, such as smart phone, computer, or tablet. As shown in FIG. 30, the communication unit A43 transmits the test result to the electronic device through a wireless communication network, such as Bluetooth, Infrared connection, or WiFi, or through a wire communication network, such as data cable. FIGS. 25 and 26 illustrate the communication circuits for Bluetooth and WiFi communication connections respectively. It is worth mentioning that a testing application is preferably downloaded and installed into the electronic device, such that when the testing application is executed in the electronic device, the test result will be transmitted thereto. Accordingly, the test result can be stored digitally, viewed, accessed, and edited via the electronic device.

Figure 17:
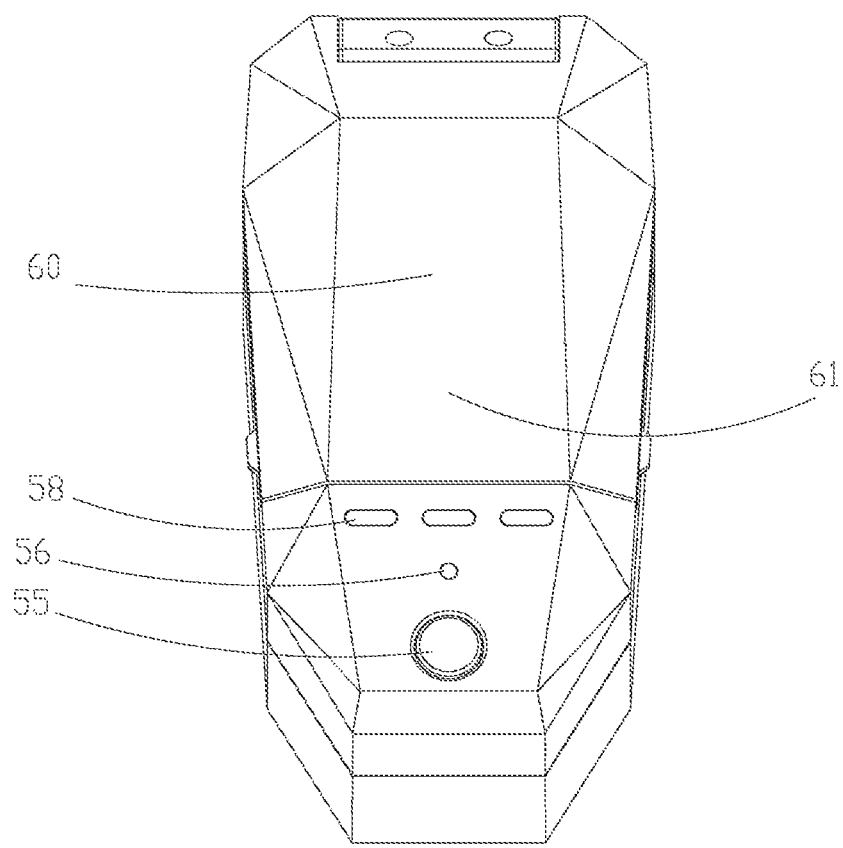
FIG. 17 is a perspective view of the testing apparatus according to the above second preferred embodiment of the present invention, illustrating the protection cover being actuated to close the test area.
Figure 18:
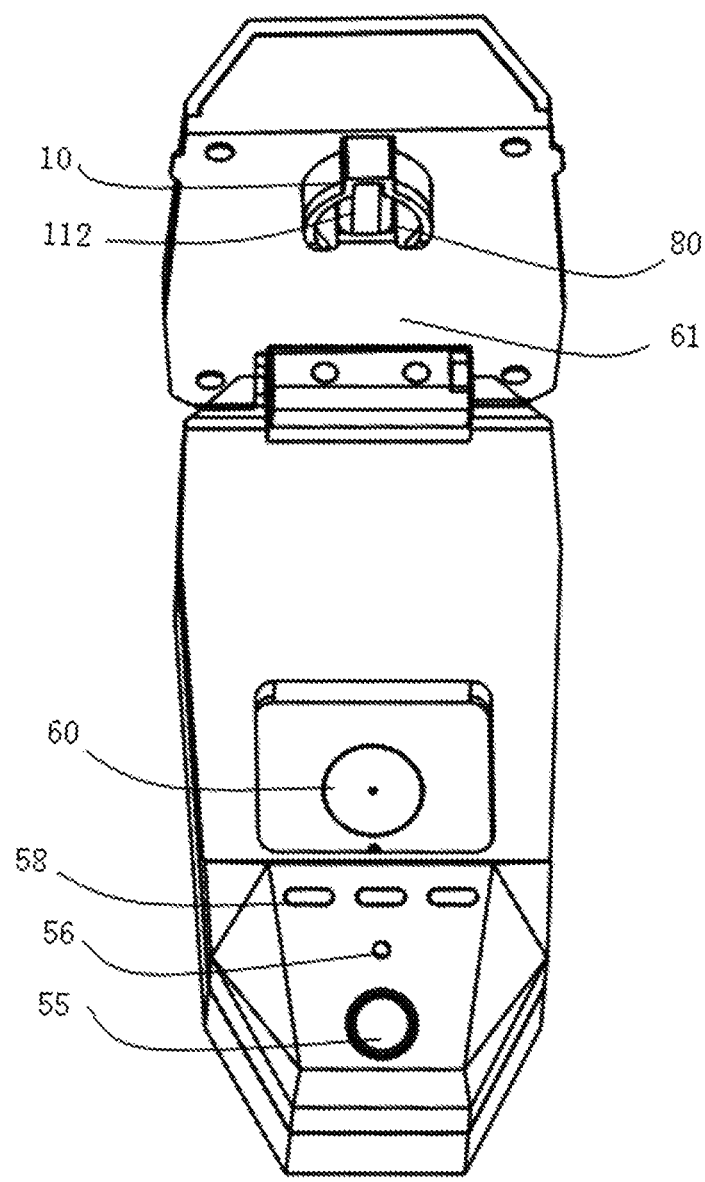
FIG. 18 is a perspective view of the testing apparatus according to the above second preferred embodiment of the present invention, illustrating the protection cover being actuated to open up the test area.

It is worth mentioning that the testing apparatus has a test area A60 that the testing object is placed in the test area A60 which is a closed environment. Accordingly, the testing apparatus comprises a protection cover A61 selectively open and close the test area A60, wherein when the protection cover A61 is actuated to open up the test area A60, as shown in FIG. 18, the testing object can be placed in the test area A60. When the protection cover A61 is actuated to close the test area A60, as shown in FIG. 17, the testing object will be enclosed within the test area A60 to form the closed environment for testing the testing object. It is worth mentioning that the test area A60 must be enclosed by the protection cover A61 in order to operate the testing apparatus to test the testing object. If the test area A60 is open, the testing apparatus will not able to operate. Since ultraviolet radiation is harmful to the human body, the UV transmission system A10 will generate ultraviolet radiation to the testing object. Therefore, the testing object is tested in a closed environment of the test area A60 via the protection cover A61 to prevent UV leakage which is harmful for human being.

The ultraviolet sensor A24 is placed within the test area A60. During the operation, the testing object is placed within the test area A60 at a position that the testing object is located on top of the ultraviolet sensor A24. When the short-wave ultraviolet light device A112 and the long-wave ultraviolet light device A122 are activated to generate the UVC and UVA to penetrate through the testing object, the ultraviolet sensor A24 will receive the UVC and UVA after the penetration. Then, the UV signal received by the ultraviolet sensor A24 will send to the signal processing system A30 and the microcontroller A40. The microcontroller A40 will analyze the intensity of the UV after penetrating through the testing object and will identify the testing object. The test result is determined by the following criteria. The testing object is determined as Moissanite when the short-wave ultraviolet and the long-wave ultraviolet received by the short-wave ultraviolet sensor and the long-wave ultraviolet sensor are weak. The light indicator A51 will generate a green light and the voice indicator A52 will generate a voice of "Moissanite". The testing object is determined as natural diamond when the short-wave ultraviolet received by the short-wave ultraviolet sensor is weak and the long-wave ultraviolet received by the long-wave ultraviolet sensor is strong. The light indicator A51 will generate a blue light and the voice indicator A52 will generate a voice of "natural diamond". The testing object is determined as synthetic diamond (HPHT/CVD diamond) when the short-wave ultraviolet received by the short-wave ultraviolet sensor is strong. The light indicator 51 will generate a yellow light and the voice indicator A52 will generate a voice of "synthetic diamond". It is worth mentioning that the test of synthetic diamond should be further identified for accuracy.

The microcontroller A40 further comprises a detection unit A44 for automatically detecting whether the testing apparatus operates properly or not. Accordingly, when the detection unit 44 detects the testing apparatus being not in used for a predetermined time period, such as 10 minutes, the testing apparatus will be automatically switched off for saving power. The testing apparatus can be re-switched on by actuating the power button A55. In other words, in case the user forgets to switch off the testing apparatus via the power button A55, the detection unit A44 will switch off the testing apparatus automatically when the testing apparatus is in an idle condition, i.e. no operation of the testing apparatus. Accordingly, the power indicator A56 will be switched off as well to indicate the power off of the testing apparatus. The testing apparatus can also be directly switched off via the actuation of the power button A55. The functional unit A50 further comprises a detection button A57 and a detection light device A58. The detection button A57 is operatively linked to the UV transmission system 10 to activate the short-wave ultraviolet light device A112 and the long-wave ultraviolet light device A122 and their corresponding circuits for testing operation. When the testing object is placed in the test area A60, the detection button A57 is then actuated and the detection light device A58 is activated to generate a light signal. Then, the testing apparatus is ready in the working mode for testing the testing object. If the test area A60 is not enclosed by the protection cover A61, i.e. the improper location of the protection cover A61, the testing apparatus cannot be operated. In other words, even though the detection button A57 is pressed, the detection light device A58 will not be activated to generate the light signal. Therefore, the testing apparatus will not be entered in the working mode that the testing object cannot be tested.

Figure 15:
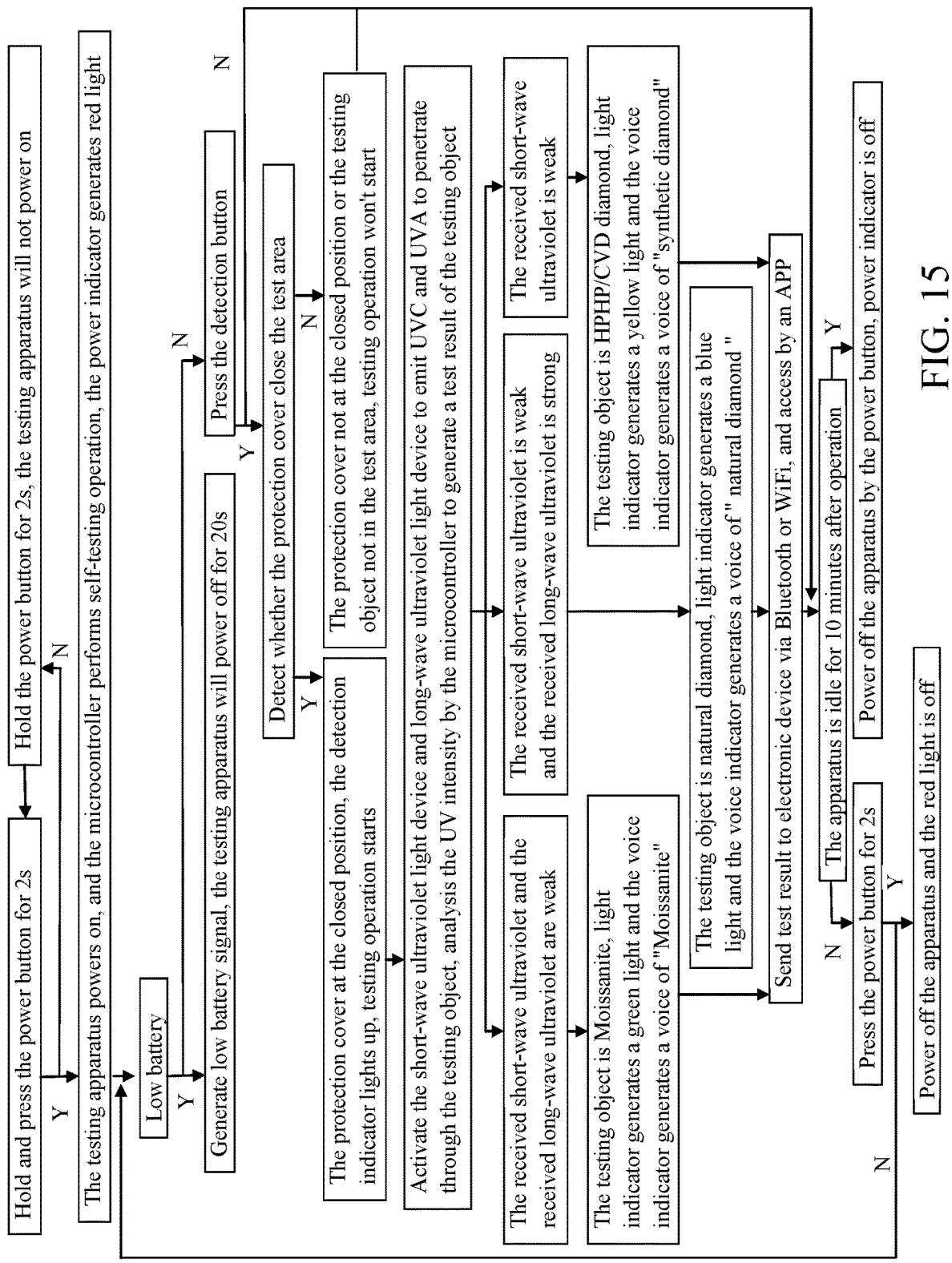
FIG. 15 is a block diagram illustrating the infrared test system of the testing apparatus according to the above second preferred embodiment of the present invention.
Figure 16:
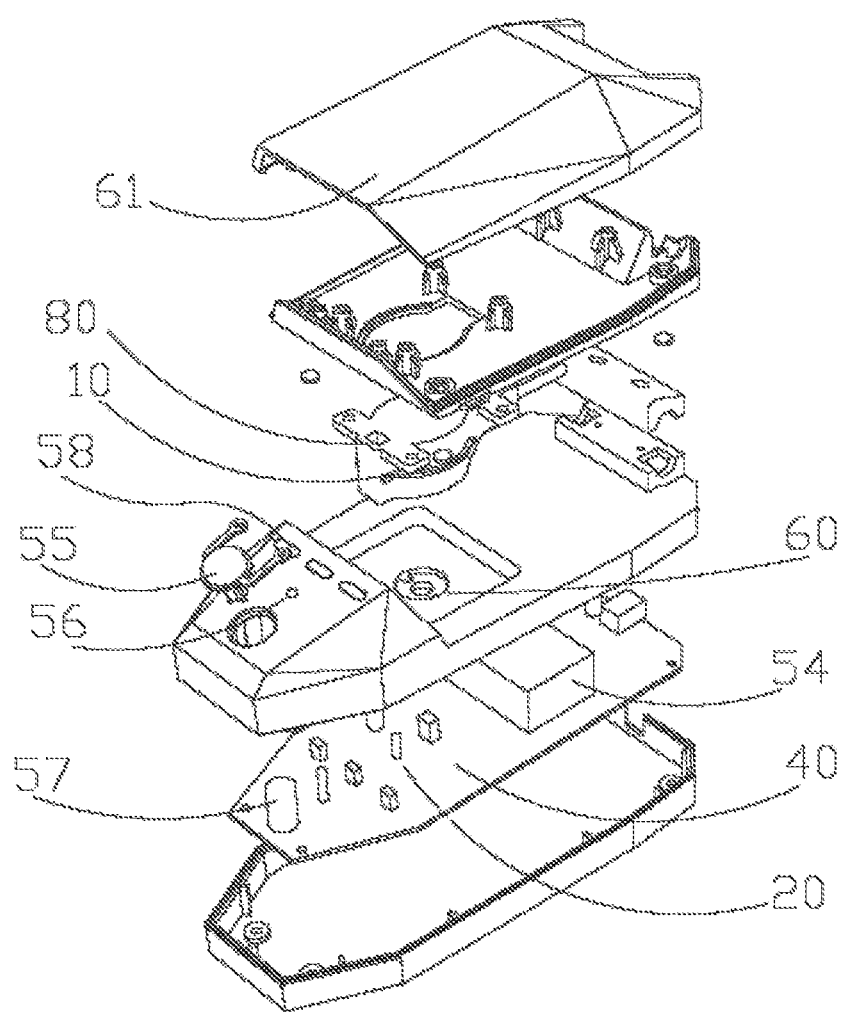
FIG. 16 is an exploded perspective view of the testing apparatus according to the above second preferred embodiment of the present invention.
Figure 20:
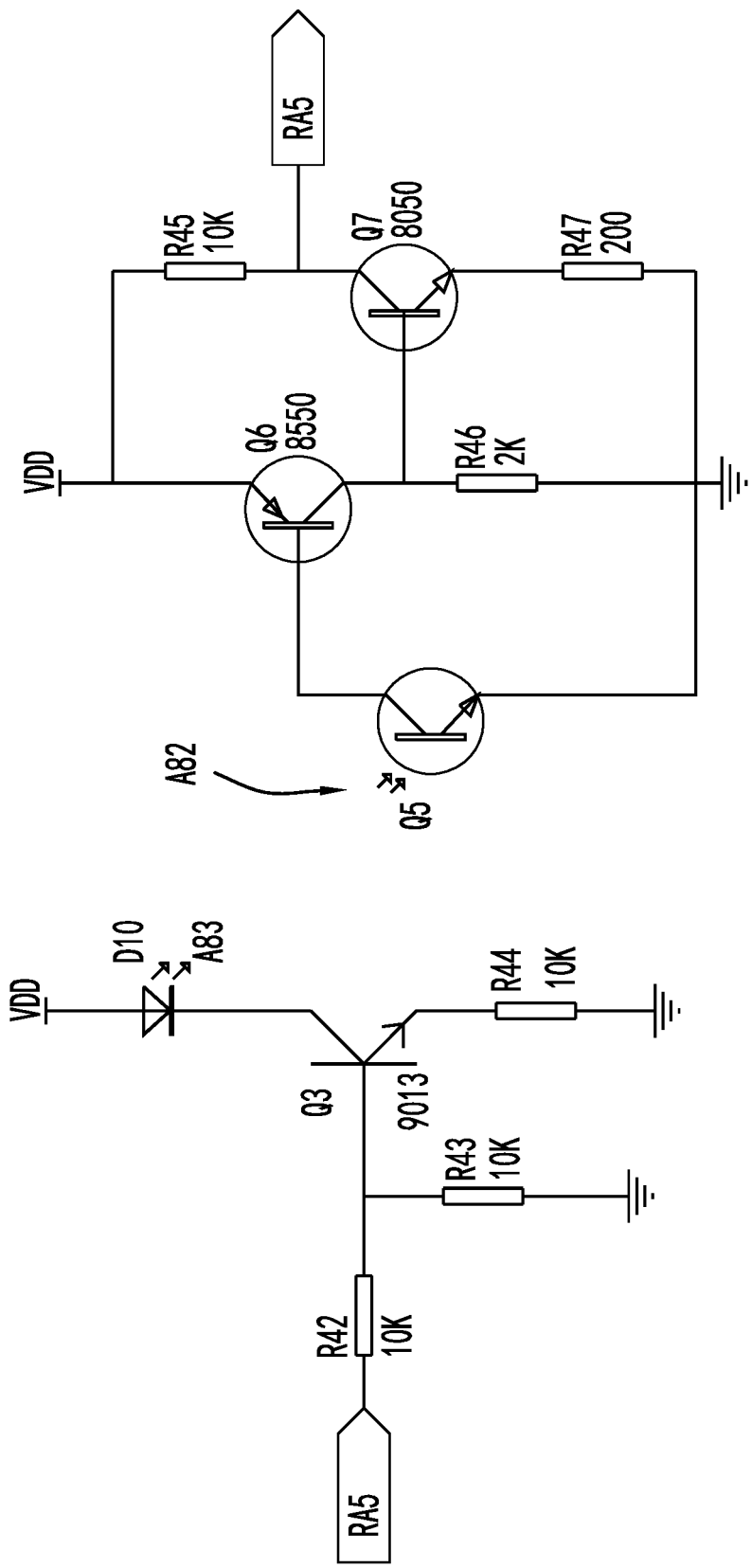
FIG. 20 is a circuit diagram of the infrared test system of the testing apparatus according to the above second preferred embodiment of the present invention.
Figure 29:
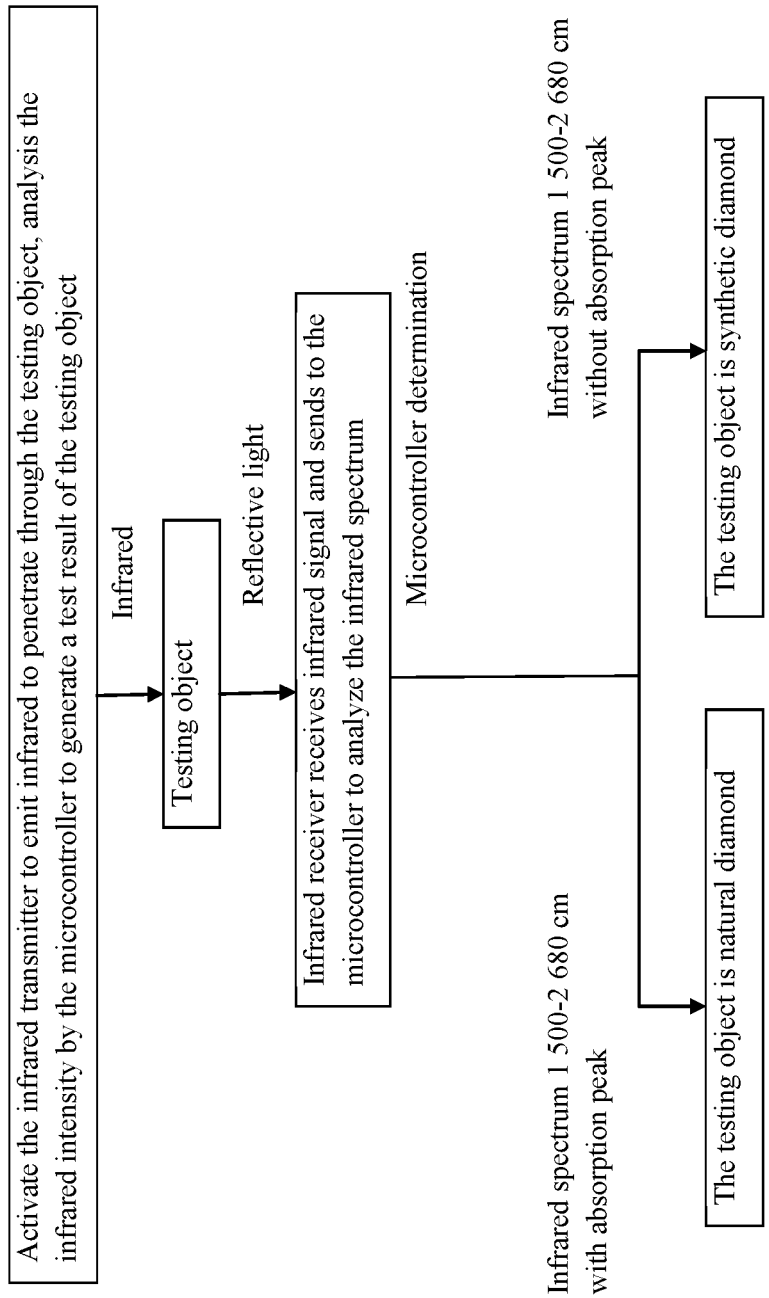
FIG. 29 is a flow diagram illustrating the infrared testing operation of the multi-functional precious stone testing apparatus according to the above second preferred embodiment of the present invention.

As shown in FIGS. 15 and 29, the infrared test system A80 comprises an infrared transmitter A83, an infrared receiver A82, and an infrared spectrum processing system A81. The infrared transmitter A83, such as an infrared light device, is arranged for emitting infrared to the surface of the testing object. The infrared receiver A82 is arranged for receiving a reflection of the infrared from the surface of the testing object. The infrared spectrum processing system A81 will process the UV signal from the infrared receiver A82 and will then send the processed UV signal to the processing unit A40 of the microcontroller A40. The transmission unit A42 will transmit the test result to the functional unit A50 and the external electronic device. FIG. 20 is a circuit diagram of the infrared test system.

It is worth mentioning that the testing object should be clean and dried in order to enhance the accuracy of the test result.

Figure 13:
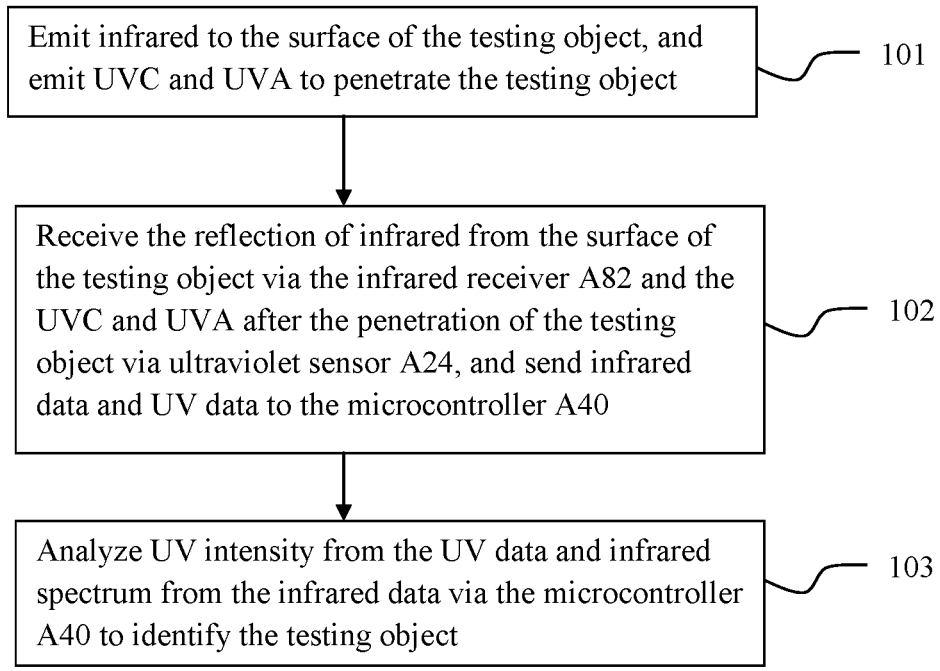
FIG. 13 is a flow diagram illustrating the testing method according to the above second preferred embodiment of the present invention.
Figure 14:
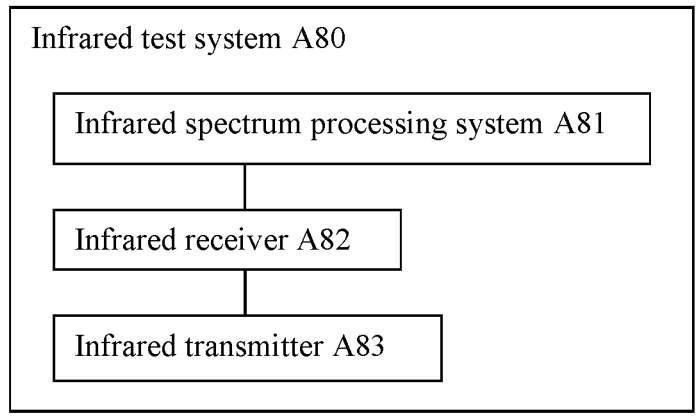
FIG. 14 is flow chart of the testing operation according to the above second preferred embodiment of the present invention.

As shown in FIGS. 13 and 14, the present invention further comprises a method of classifying a testing object, especially for distinguishing between natural diamonds and synthetic diamonds, by a multi-functional precious stone testing apparatus, wherein the method comprises the following steps. infrared test system which an infrared transmitter for emitting infrared to the surface of the testing object, and an infrared receiver (A) Emit infrared to the surface of the testing object via the infrared transmitter A83 of the infrared test system A80, and emit UVC and UVA to penetrate the testing object via the UV transmission system A10 {STEP 101}.

(B) Receive the reflection of infrared from the surface of the testing object via the infrared receiver A82 and the UVC and UVA after the penetration of the testing object via the short-wave ultraviolet sensor and the long-wave ultraviolet sensor of ultraviolet sensor A24, and send infrared data and UV data to the microcontroller 40 {STEP 102}.

(C) Analyze UV intensity from the UV data and infrared spectrum from the infrared data via the microcontroller A40 to identify the testing object {STEP 103}.

Figure 19:
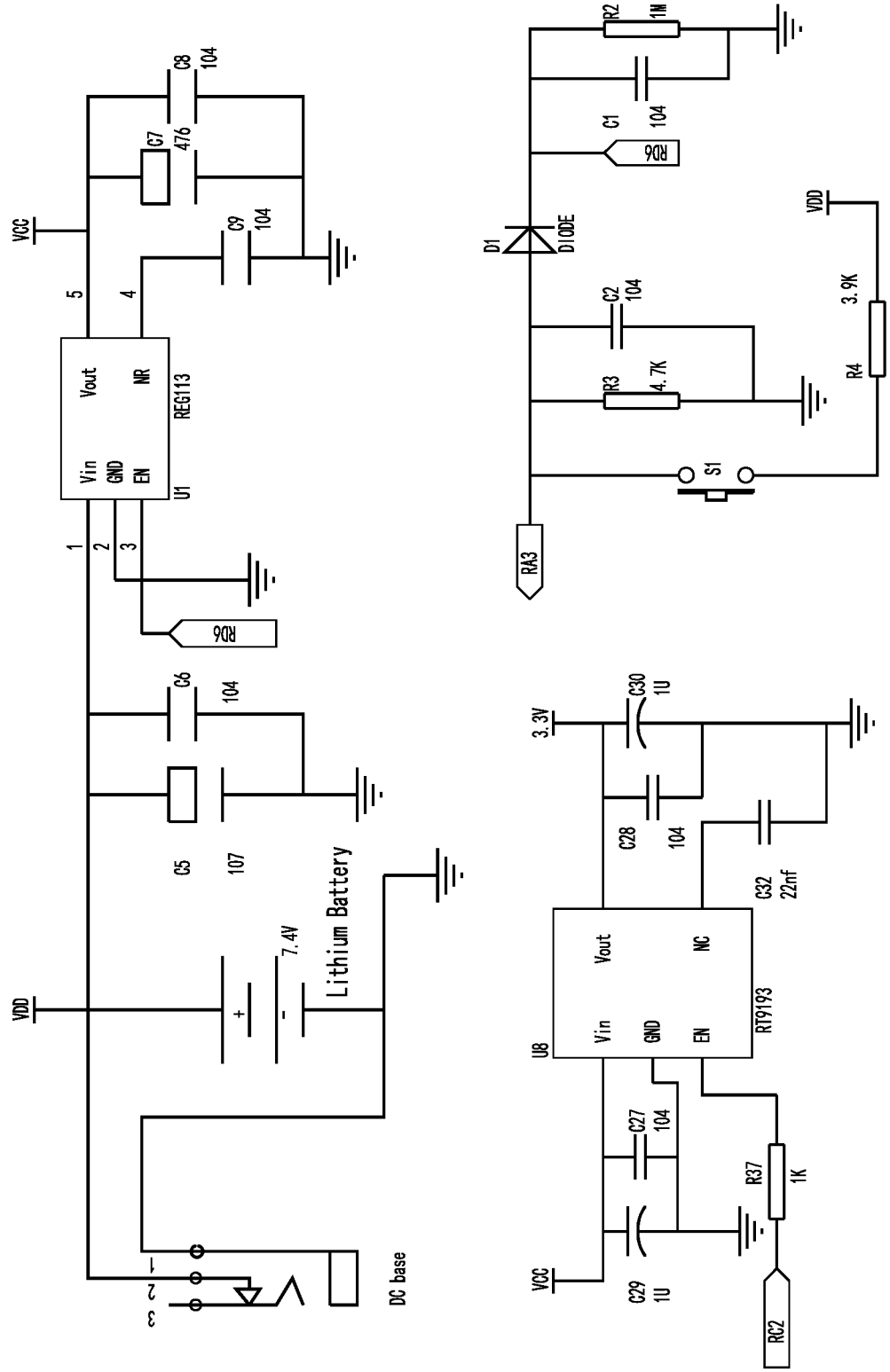
FIG. 19 illustrates a circuit diagram of the power supplying arrangement of the testing apparatus according to the above second preferred embodiment of the present invention.

It is worth mentioning that, in the step (A), UVC and UVA are emitted by the short-wave ultraviolet UVA transmitter A11 and the long-wave ultraviolet UVA transmitter A12 respectively. Accordingly, when the detection button A57 is actuated, such as the depression of the detection button A57, the short-wave ultraviolet light device A112 and the long-wave ultraviolet light device A122 are activated for generating the UVC and UVA to penetrate the testing object. It is worth mentioning that the short-wave ultraviolet light device A112 is powered by the power supplier A54 and is activated through the boost inverter circuit A111 for generating UVC. The long-wave ultraviolet light device A122 is powered by the power supplier A54 and is activated through the constant current circuit A121 for generating UVA. FIG. 19 illustrates a power supplying circuit of present invention.

In the step (B) and the step (C), the ultraviolet sensor A24 will receive the ultraviolet as the UV signal after ultraviolet penetrates through and/or is absorbed by the testing object. Then, the UV signal received by the ultraviolet sensor A24 will send to the signal processing system A30 and the microcontroller A40. The microcontroller A40 will analyze the intensity of the UV after penetrating through the testing object and will identify the testing object. In particular, the microcontroller A40 will analyze the intensity of UVC and UVA after penetrating through the testing object.

Furthermore, the processing unit A41 can also perform a detailed analysis of spectrum or a light radiation detection for determining the light absorption and light penetration so as to identify the properties of the testing object. As a result, the testing object can be distinguished as natural diamonds or synthetic diamonds.

It is worth mentioning that the UV transmission system A10 can be incorporated with different emission systems under the control of the microcontroller A40 to emit the light beam to the testing object. Therefore, due to the different refractions of the light beam, the present invention is able to identify the testing object.

After the processing unit A41 processes and analyses the UV intensity, the test result will be obtained. The transmission unit A42 will send the test result signal to the light indicator A51, the voice indicator A52, and/or the display A53. The transmission unit A42 will send the test result to the electronic device through the communication unit A43.

The testing object is determined as Moissanite when the short-wave ultraviolet and the long-wave ultraviolet received by the short-wave ultraviolet sensor and the long-wave ultraviolet sensor are weak. The light indicator A51 will generate a green light and the voice indicator A52 will generate a voice of "Moissanite". The testing object is determined as natural diamond when the short-wave ultraviolet received by the short-wave ultraviolet sensor is weak and the long-wave ultraviolet received by the long-wave ultraviolet sensor is strong. The light indicator A51 will generate a blue light and the voice indicator A52 will generate a voice of "natural diamond". The testing object is determined as synthetic diamond (HPHT/CVD diamond) when the short-wave ultraviolet received by the short-wave ultraviolet sensor is strong. The light indicator A51 will generate a yellow light and the voice indicator A52 will generate a voice of "synthetic diamond". It is worth mentioning that the test of synthetic diamond should be further identified for accuracy. According to the above three test results, the present invention is adapted to simultaneously display the relevant results on the display A53.

In addition, before the operation of the testing apparatus, the testing object must be placed in the test area A60. In particular, the testing object must be placed in the test area 60 in a closed environment via the protection cover A61. For operation, the power button A55 must be pressed and held, as an example, for two seconds. The testing apparatus will not be powered on if the power button A55 is not held for two seconds. The pressing time for the power button A55 can be selectively adjusted by the manufacturer. When the testing apparatus will be powered on, the microcontroller A40 will perform a self-testing operation. In the self-testing operation, the power indicator A56 is activated to check the power status of the power supplier A54. In case of low battery, the power indicator A56 will generate a low battery signal, such as a light blinking signal, such that the rechargeable battery of the power supplier A54 should be recharged before it is used. The testing apparatus will be automatically powered off for a period of time, such as 20 seconds, after the power indicator A56 generates the low battery signal.

When the power in the power supplier A54 is adequate for operation, the detection button A57 can be pressed to detect whether the test area A60 to be enclosed by the protection cover A61. If the protection cover A61 does not close the test area A60 or there is no testing object in the test area A60, the testing apparatus will not be able to operate and the detection light device A58 will not be activated. When the protection cover A61 is actuated to close the test area A60 and the testing object is placed in the test area A60, the detection light device A58 will be activated for light indication and the testing apparatus is ready for operation. The testing operation of the testing apparatus is mentioned in the step (A) to step (C).

It is worth mentioning that the test result will be transmitted to the electronic device, wherein when the testing application is executed in the electronic device, the test result can be stored digitally, viewed, accessed, and edited via the electronic device.

As it is mentioned above, each testing object has its own characteristics, including their thermal and electrical conductivities. The present invention uses their own characteristics to identify the precious stone is natural or lab-grown diamond or other stones. In particular, the present invention is able to accurately identify 30 different kinds of precious stones, especially for the colored gemstones. Accordingly, the thermal conductivity of natural diamond is the strongest among all the precious stones. Only blue diamonds are semiconductors while the rest of natural diamonds are non-conductive. The electrical conductivity and thermal conductivity of Moissanite are strong. Therefore, by measuring the electrical conductivity and thermal conductivity of the testing object and comparing the color of the testing object, the present invention is able to accurately identify different kinds of precious stones.

Referring to FIGS. 31 to 35, the multi-functional precious stone testing apparatus comprises a microcontroller B10, a probe head assembly B20, an electrical conductive assembly B30, and a functional unit B40. The probe head assembly B20 is operatively linked to the microcontroller B10 and the electrical conductive assembly B30 for measuring the thermal conductivity and the electrical conductivity of the testing object by means of contact. A thermal conductive signal and the electrical conductive signal are collected and transmitted to the microcontroller B10 for analyzing and processing the strengths of the thermal conductivity and the electrical conductivity of the testing object in order to identify the testing object. The test result will be transmitted to the functional unit B40 for further rendering.

The probe head assembly B20 comprises at least a detection probe B21 operatively connected to the microcontroller B10 and at least a thermistor B22, preferably at least two thermistors, operatively connected to the detection probe B21, wherein the detection probe B21 is arranged for measuring the thermal conductivity of the testing object when the detection probe B21 contacts with the testing object. It is worth mentioning that two, three, four, or more thermistors are selectively incorporated with the detection probe B21. According to the preferred embodiment, two thermistors B22 are incorporated with the detection probe B21. Therefore, when the detection probe B21 contacts with the testing object to measure the thermal conductivity and the electrical conductivity of the testing object. Then, the thermal conductive signal and the electrical conductive signal are collected and transmitted to the microcontroller B10 for analyzing and processing the strengths of the thermal conductivity and the electrical conductivity of the testing object in order to identify the testing object.

The detection probe B21 is made of rigid material to withstand a predetermined pressure when contacting with the testing object. In particular, when testing the testing object, the detection probe B21 should press on the testing object to ensure the contact therebetween for accurately and stably measuring the thermal conductivity and the electrical conductivity of the testing object. FIG. 44 illustrates the detection probe B21 and its circuit diagram.

Figure 45:
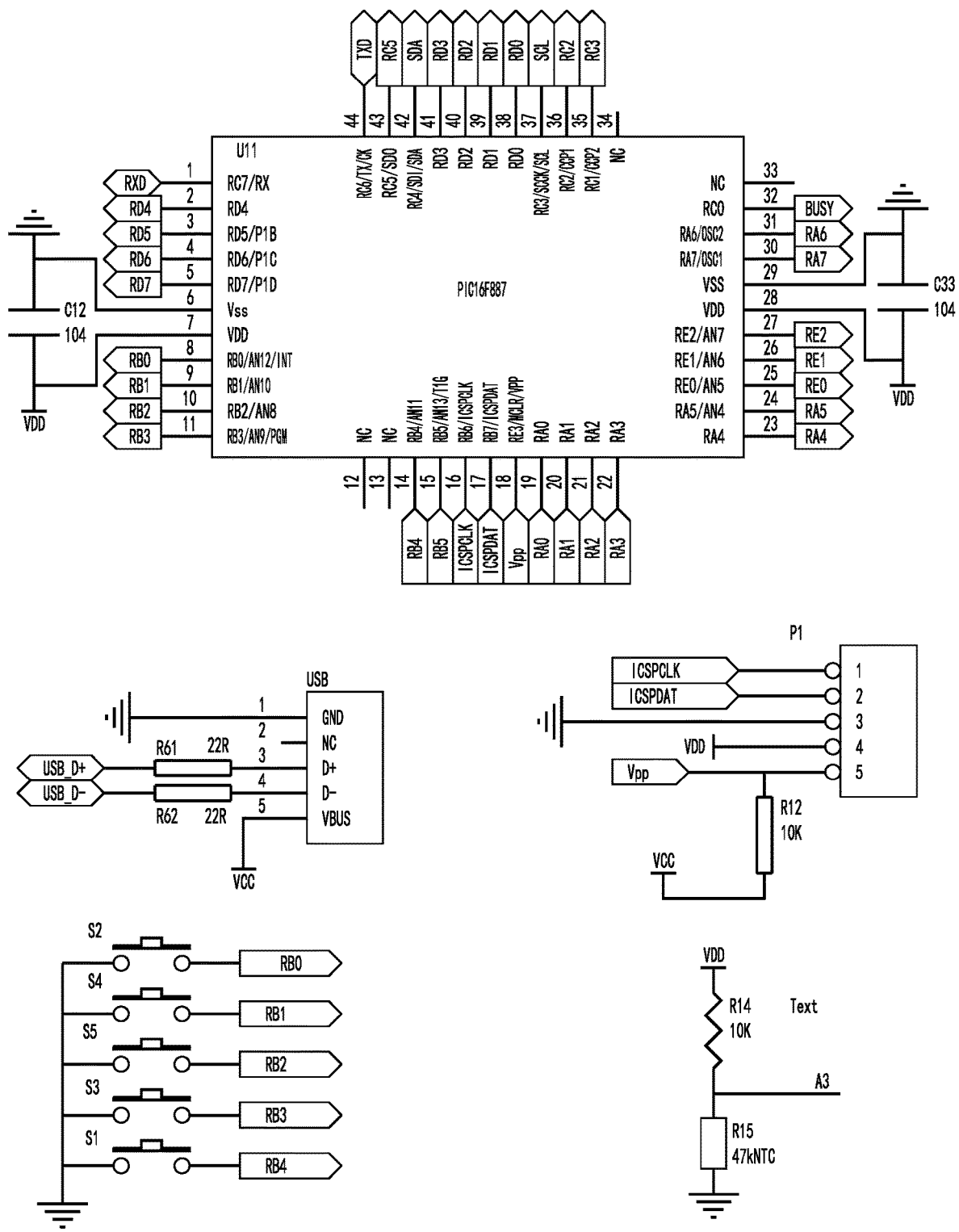
FIG. 45 is a circuit diagram of the microcontroller of the multi-functional precious stone testing apparatus according to the above third preferred embodiment of the present invention.

The microcontroller B10 comprises an amplifying circuit B11, a processing unit B12, a transmission unit B13, wherein the processing unit B12 is operatively linked to the amplifying circuit B11 and the transmission unit B13. The amplifying circuit B11 is operatively linked to the detection probe B21 and the thermistor B22, wherein the thermal conductive signal is collected and amplified by the amplifying circuit B11, and is then transmitted to the processing unit B12. The processing unit B12 is arranged for analyzing and processing of the strength of the thermal conductivity of the testing object to generate the test result. The test result is then transmitted by the transmission unit B13 from the processing unit B12. FIG. 45 illustrates the circuit diagram of the microcontroller B10.

It is worth mentioning that the detection probe B21 is heated up by the activation of the thermistor B22, such that when the detection probe B21 contacts the testing object, the thermal energy from the detection probe B21 will be transferred to the testing object. In other words, the temperature at the detection probe B21 will be reduced after the contact of the testing object. The thermistor B22 will measure the temperature change at the detection probe B21 and send the temperature change data to the processing unit B12. The processing unit B12 is arranged for analyzing and processing the temperature change data to determine the thermal conductivity of the testing object and is arranged for converting the temperature change data to the thermal conductive signal. The test result will be transmitted and shown as a digital image or voice signal.

Figure 46:
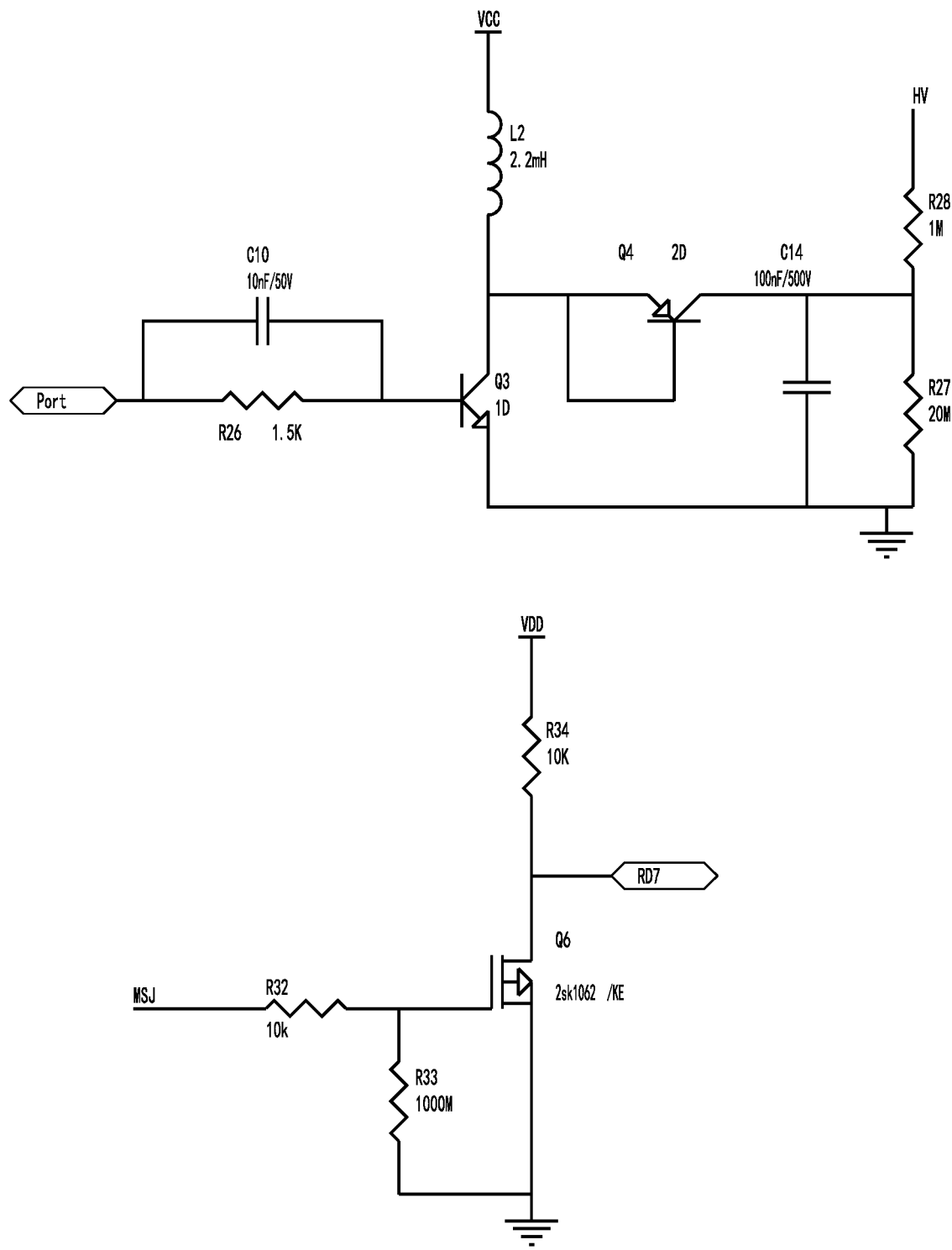
FIG. 46 is a circuit diagram of the booster circuit of the multi-functional precious stone testing apparatus according to the above third preferred embodiment of the present invention.

The electrical conductive assembly B30 comprises at least an electrical member B31 and an electrical conductor B32 provided at the detection probe B21. The microcontroller B10 further comprises a booster circuit B14, wherein the electrical member B31 is operatively connected to the processing unit B12 through the booster circuit B14. FIG. 46 illustrates the circuit diagram of the booster circuit B14. During the testing operation, the detection probe B21 contacts the testing object to measure the thermal conductivity of the testing object. At the same time, the booster circuit B14 is activated to controllably regulate a voltage of the electrical member B31, i.e. regulate the electrical member B31 in high voltage, so as to electrically conduct with the testing object, such that the electrical conductor B32 contacts with the testing object via the detection probe B21 to measure the electrical conductivity of the testing object. The electrical conductive signal is collected and is transmitted to the processing unit B12 for analyzing and processing of the strength of the electrical conductivity of the testing object. As a result, the processing unit B12 will comprehensively analyze and process the strengths of the thermal conductivity and the electrical conductivity of the testing object in order to identify the testing object. The test result will be generated and transmitted via the transmission unit B13 to a display B43, which is preferably an OLED. Accordingly, the electrical member B31 can be a metal plate or other material having an electrical conductive ability.

Figure 43:
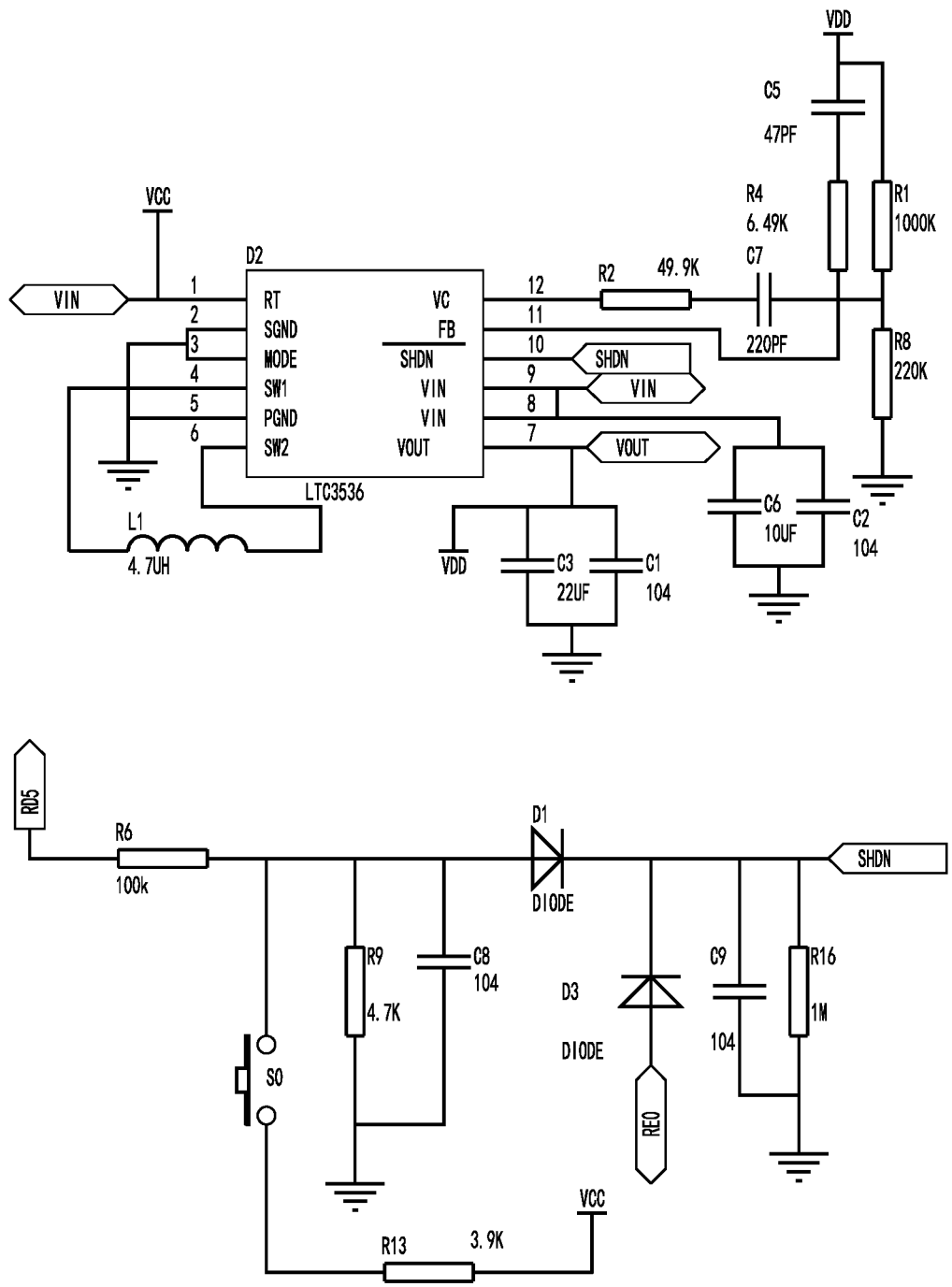
FIG. 43 is a circuit diagram of the power supply of the multi-functional precious stone testing apparatus according to the above third preferred embodiment of the present invention.

The functional unit B40 comprises a power control B41, such as a power switch, a power supplier B42, the display B43, a voice indicator B44, a function key B45, and a power charging base B46. The power control B41 is operatively connected to the power supplier B42, the display B43, the voice indicator B44, the function key B45, the power charging base B46, the microcontroller B10, the probe head assembly B20, and the electrical conductive assembly B30. FIG. 43 illustrating the power supplying circuit of the present invention. In other words, the power control B41 is activated, such as an actuation of the power switch, to power up the testing apparatus of the present invention to start testing the testing object. The power control B41 is deactivated, such as the actuation of the power switch, to switch off the testing apparatus of the present invention after the testing operation the testing object is completed. Therefore, when the power control B41 is activated, the power supplier B42 will supply adequate power to the microcontroller B10, the probe head assembly B20, the electrical conductive assembly B30, the display B43, the voice indicator B44, and the function key B45.

It is worth mentioning that the power supplier B42 can be a replaceable battery, a rechargeable battery, or a power terminal for connecting to an external electric socket. Preferably, the power supplier B42 comprises the rechargeable battery to enhance the portability of the testing apparatus as a handheld apparatus. The handheld apparatus is also easy to operate. The power supplier B42 can be recharged via the power charging base B46. It is worth mentioning that the power supplier B42 has a charging terminal connected to the rechargeable battery, such that the power supplier B42 will be recharged when the charging terminal contacts with the power charging base B46, such that rechargeable battery will not be removed from the testing apparatus during the charging operation.

The display B43 and the voice indicator B44 are operatively linked to the processing unit B12 to receive the test result therefrom. Therefore, the test result will be displayed on the display B43 and will be broadcasted via the voice indicator B44. In other words, the user is able to view the test result via the display B43 and/or listen to the test result via the voice indicator B44. Therefore, the test result can be presented in different ways. It is worth mentioning that the display B43 and the voice indicator B44 can be two individual output devices for showing the test result in different ways. It is appreciated that the display B43 and the voice indicator B44 can be integrated to form a single output device.

Figure 40:
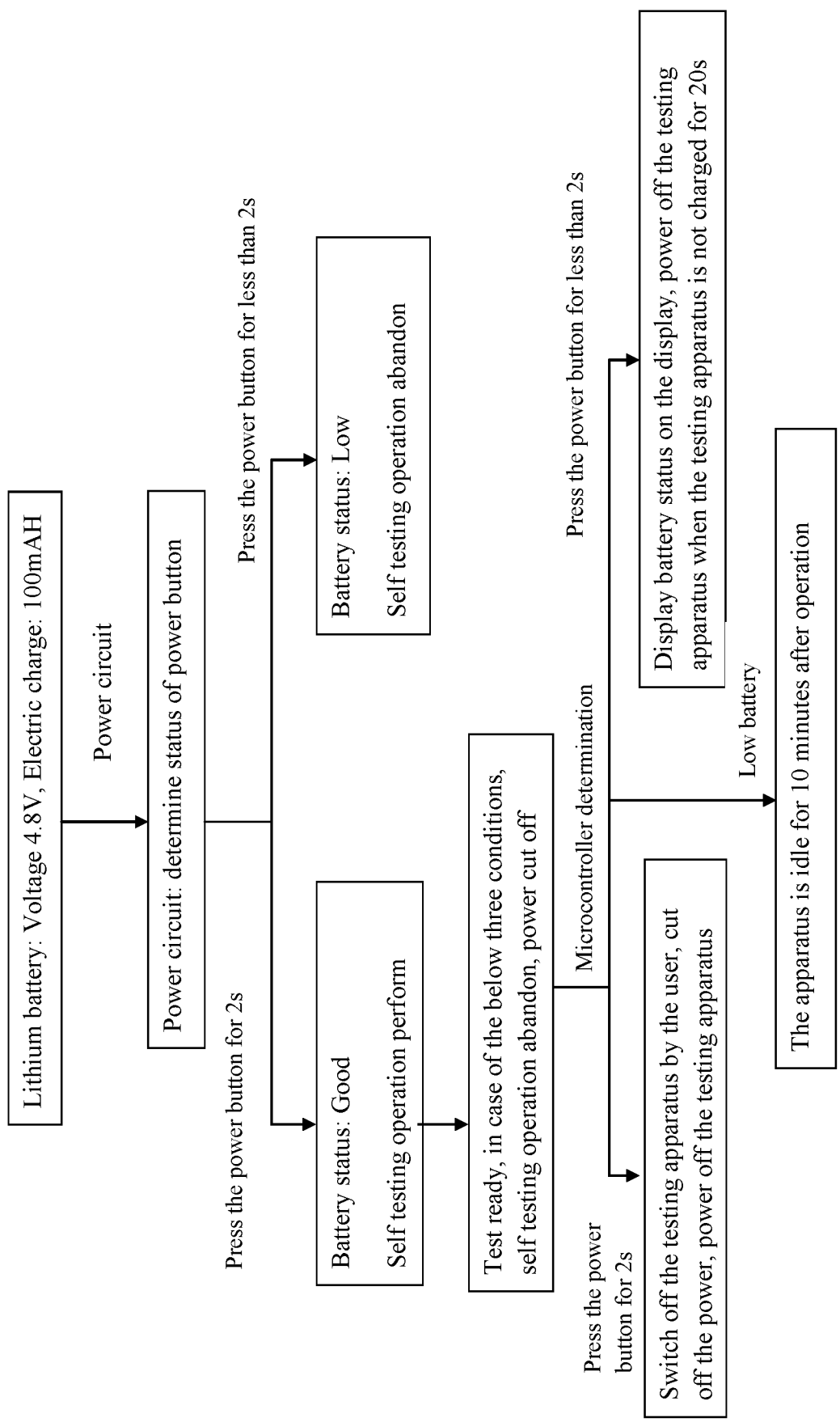
FIG. 40 is a flow diagram illustrating the power supplying of the multi-functional precious stone testing apparatus according to the above third preferred embodiment of the present invention.

During the operation of the testing apparatus, for example, the power control B41 should be pressed and held for a period of activation time, such as two seconds. The microcontroller B10 will perform a self-testing operation, as shown in FIG. 40. The display B43 will be automatically activated. The probe head assembly B20 will be pre-heated for a predetermined of heat time, such as 10 seconds, wherein the display B43 will show the heating status of the probe head assembly B20. In case of low battery, the display B43 will show the battery status, and/or the voice indicator B44 will generate a low battery voice signal to remind the user to recharge the power supplier B42. Once the pre-heating operation of the probe head assembly B20 is completed, the display B43 will show the pre-heated status of the probe head assembly B20 and will ready for testing. When the testing apparatus is switched off, the display B43 will be off as well.

Preferably, the display B43 is a OLED (digital Organic LED), wherein the size of the display B43 can be optimized to built-in with the testing apparatus.

It is worth mentioning that the display B43 not only displays the test result but also displays the on-off status and the testing status of the testing apparatus. The display B43 further displays different corresponding information, such as self-checking information, battery status, and color selection information.

The function key B45 is operatively provided at the display B43, wherein the function key B45 comprises an up-moving key B451, a down-moving key B452, and a selection key B453 to selectively control location on the display B43 and select the corresponding options of the display B43. For example, a plurality of color selections are displayed on the display B43, such that the user is able to select one of the color selections via the up-moving key B451 and the down-moving key B452, and confirm the color selection via the selection key B453. Preferably, the display B43A can be a touch screen display to serve as an input device. Therefore, the function key B45 can be displayed on the display B43A and can be selected via a touch of the display B43A.

Figure 42:
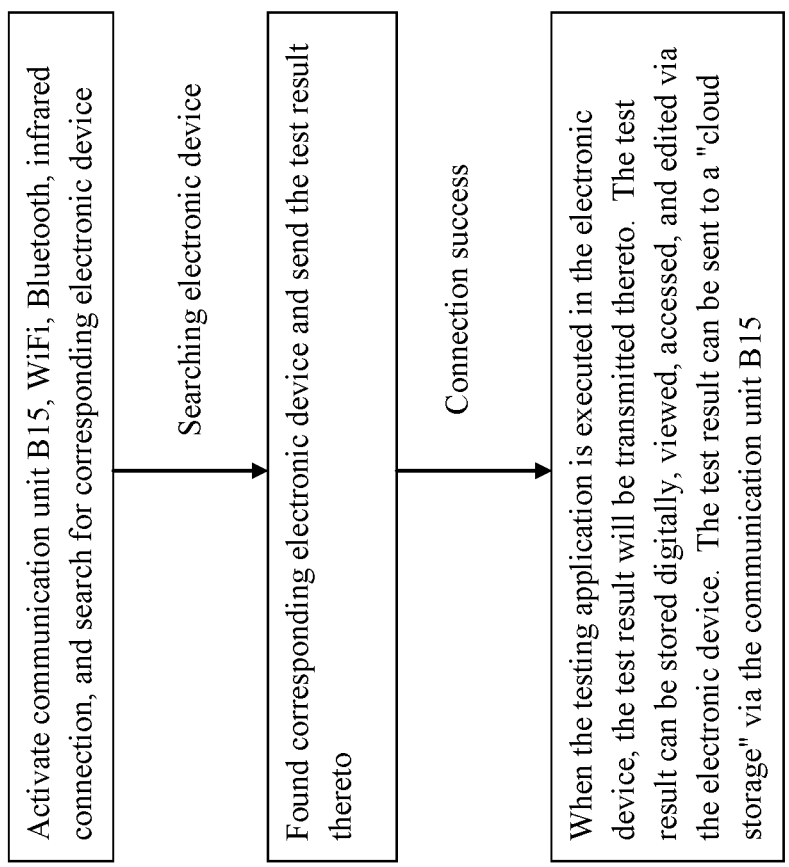
FIG. 42 illustrates a flow diagram illustrating the wireless connection of the electronic device for data transmission via the communication unit of the multi-functional precious stone testing apparatus according to the above third preferred embodiment of the present invention.

The microcontroller B10 further comprises a communication unit B15 operatively linked to the transmission unit B13 for transmitting the test result therefrom. The communication unit B15 is arranged to transmit the test result to the functional unit 50 and at the same time to transmit the test result to an external electronic device, such as smart phone, computer, or tablet. As shown in FIG. 42, the communication unit B15 transmits the test result to the electronic device through a wireless communication network, such as Bluetooth, Infrared connection, or WiFi, or through a wire communication network, such as data cable. Accordingly, the communication unit B15 will automatically detect any electronic device in order to send the test result thereto. It is worth mentioning that a testing application is preferably downloaded and installed into the electronic device, such that when the testing application is executed in the electronic device, the test result will be transmitted thereto. Accordingly, the test result can be stored digitally, viewed, accessed, and edited via the electronic device. It is worth mentioning that the test result can be sent to a "cloud storage" via the communication unit B15.

The microcontroller B10 further comprises a detection unit B16 for automatically detecting whether the testing apparatus operates properly or not. Accordingly, the detection unit B16 is operatively linked to the power control B41, the power supplier B42, the probe head assembly B20, and the processing unit B12. Once the power control B41 is activated, the detection unit B16 will detect the battery status of the power supplier B42, the pre-heat status of the probe head assembly B20, and the contact status of the probe head assembly B20, so as to send all the status information to the processing unit B12. When the detection unit B16 detects the low battery of the power supplier B42, the temperature of the probe head assembly B20 not reach the pre-heat temperature, and/or the improper contact of the probe head assembly B20 to the testing object, the testing operation of the testing apparatus cannot be started. The detection result from the detection unit B16 will be shown in the display B43 and will be broadcasted via the voice indicator B44. The detection unit B16 further detects the testing status of the testing apparatus. When the detection unit B16 detects the testing apparatus being not in used for a predetermined time period, such as 10 minutes, the testing apparatus will be automatically switched off for saving power. It is worth mentioning that when the detection unit B16 detects the low battery of the power supplier B42, the testing apparatus will be automatically powered off for a period of time, such as 20 seconds, after the low battery signal is generated.

The testing apparatus further comprises a portable housing B50 which comprises a hand-held casing B51, a probe casing B52, a battery cover B53, and a display cover B54. Accordingly, the microcontroller B10, the probe head assembly B20, the electrical conductive assembly B30, and the functional unit B40 are operatively assembled in the hand-held casing B51. The detection probe B21 is protected within the probe casing B52 when the detection probe B21 is not in use. In other words, the detection probe B21 will be exposed out of the probe casing B52 for testing the testing object. The battery cover B53 is coupled at the hand-held casing B51 to enclose the rechargeable battery of the power supplier B42. The battery cover B53 can be detached from the hand-held casing B51 to charge the rechargeable battery of the power supplier B42. The display B43 is protected by and enclosed within the display cover B54, wherein the display cover B54 is transparent, such that the display B43 can be seen through the display cover B54.

Figure 36:
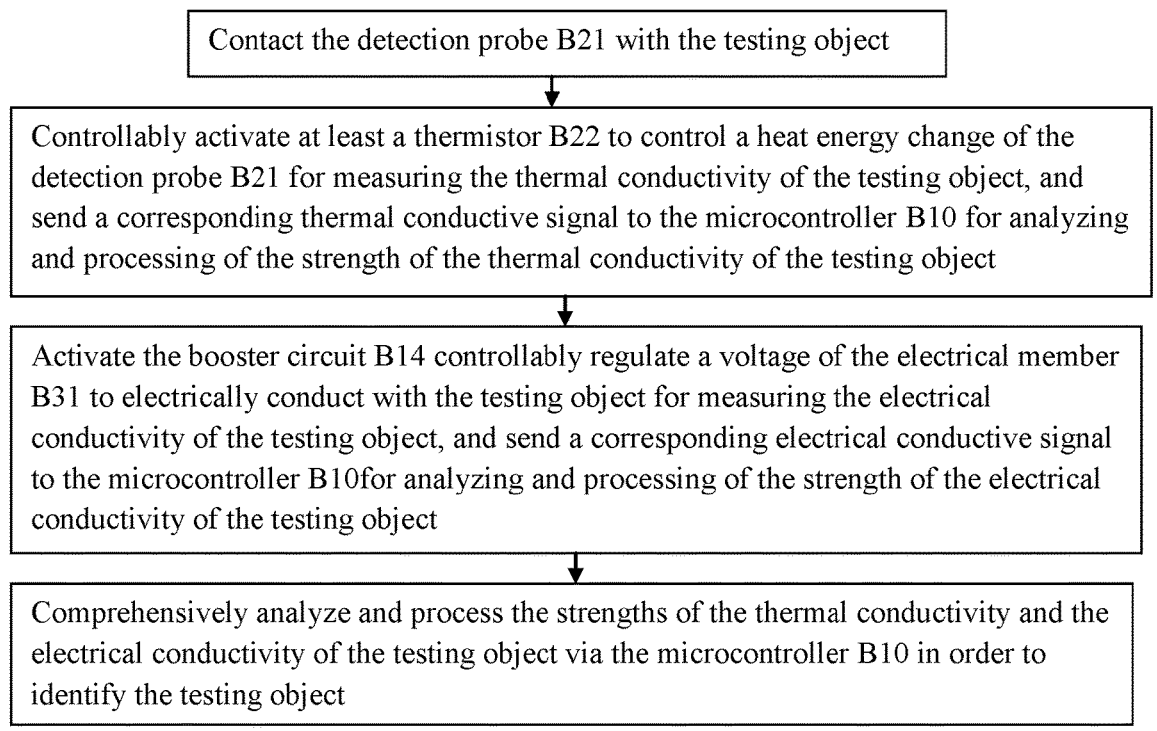
FIG. 36 is a flow diagram illustrating the testing method according to the above third preferred embodiment of the present invention.
Figure 35:
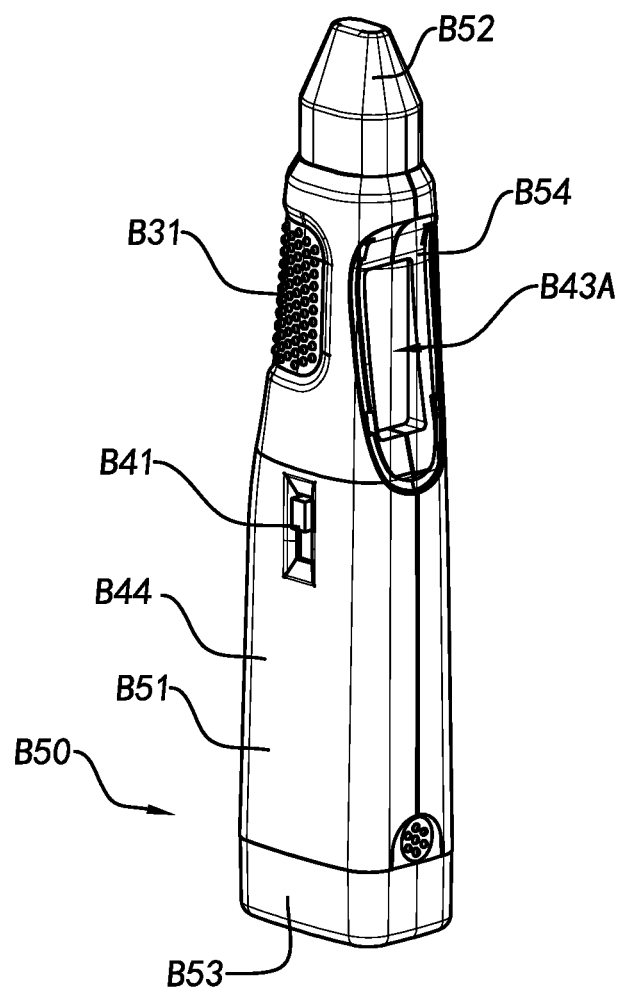
FIG. 35 illustrates an alternative mode of the multi-functional precious stone testing apparatus according to the above third preferred embodiment of the present invention.
Figure 37:
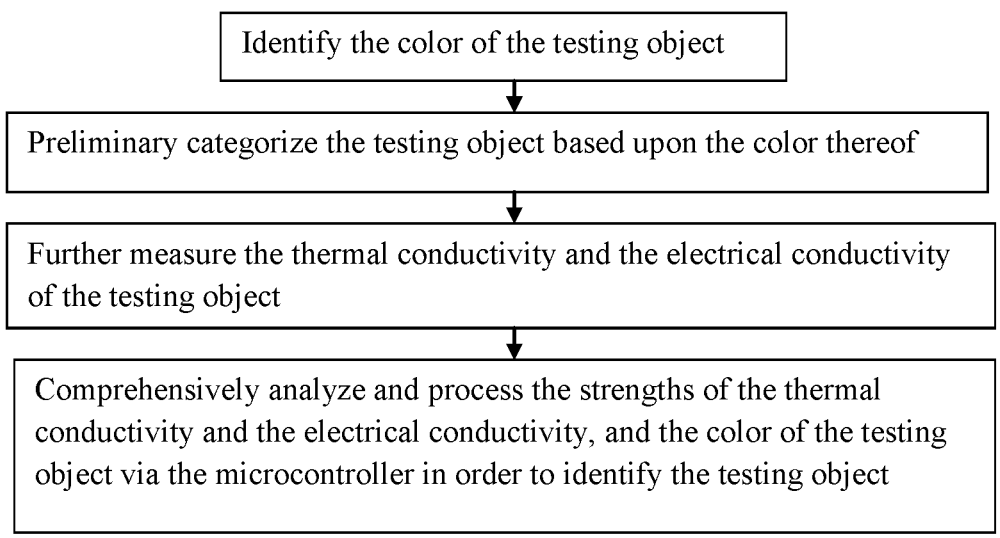
FIG. 37 is a flow diagram illustrating the testing method according to the above third preferred embodiment of the present invention, illustrating the sub-steps for the identification of other gemstones.
Figure 38:
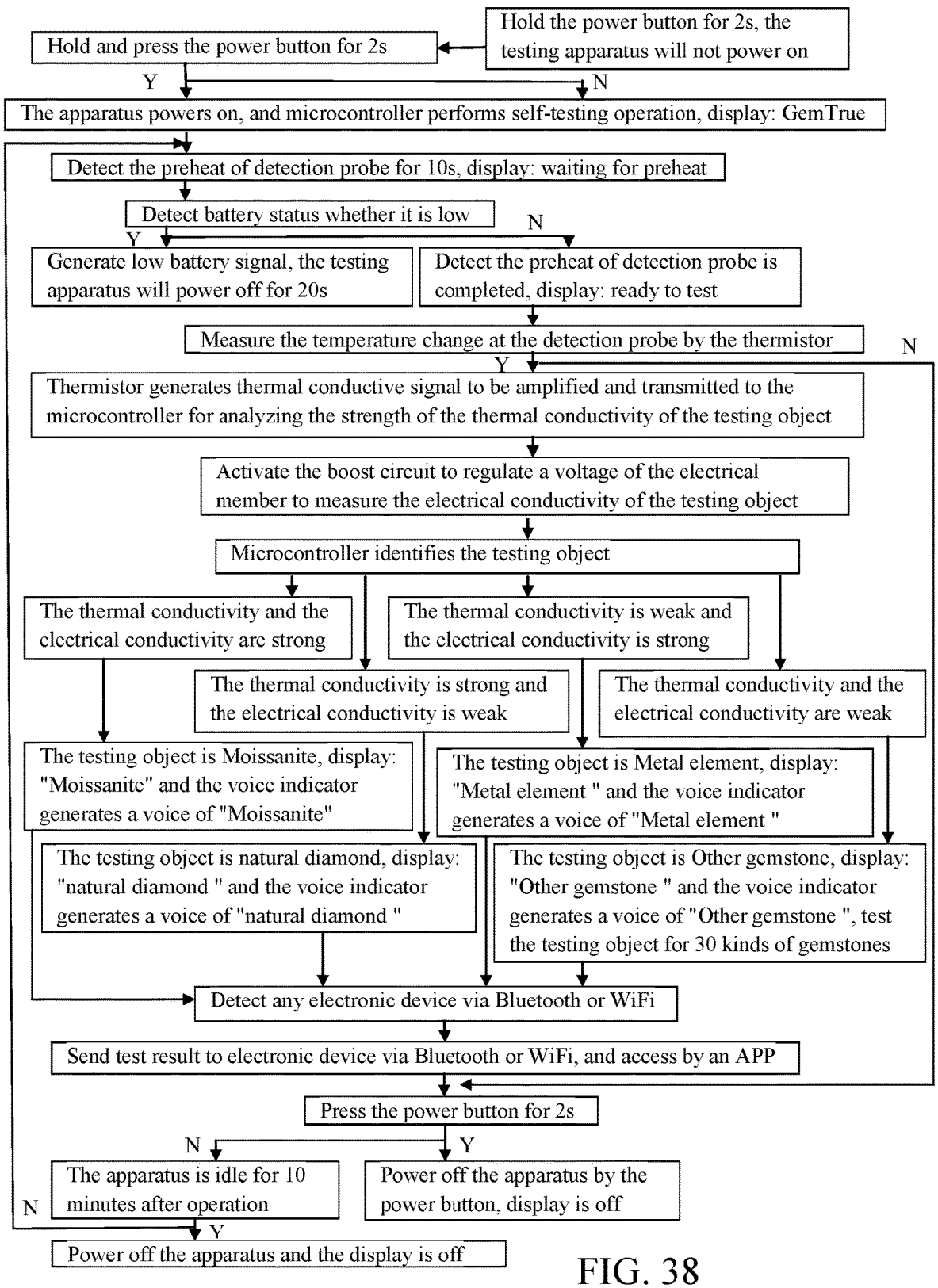
FIG. 38 is flow chart of the testing operation according to the above third preferred embodiment of the present invention.

As shown in FIGS. 36 to 38, a method of classifying a testing object by the multi-functional precious stone testing apparatus is illustrated. When the testing apparatus is powered up, the detection unit B16 will perform a self-testing operation to detect the proper operation of the testing apparatus. To start testing the testing object, the detection probe B21 can be vertically placed on the testing object to ensure the proper contact and pressure thereon. Then, the thermal conductivity and the electrical conductivity of the testing object will be measured. Accordingly, when two thermistors B22 are used, one of the thermistors B22 will heat up the detection probe B21 at a predetermined pre-heat temperature. Therefore, the heat at the detection probe B21 will transfer to the testing object when the detection probe B21 contacts with the testing object. As a result, the temperature of the detection probe B21 will be reduced. Accordingly the second thermistor B22 will measure the temperature change at the detection probe B21 and will send the temperature change signal to the amplifying circuit B11. Once the temperature change signal is amplified by the amplifying circuit B11, the signal will then be transmitted to the processing unit B12. The processing unit B12 will analyze and process of the strength of the thermal conductivity of the testing object.

During the measurement of the thermal conductivity of the testing object, the electrical conductivity of the testing object can be measured at the same time. Accordingly, when the detection probe B21 properly contacts with the testing object, the booster circuit B14 is activated to controllably regulate the high voltage at the electrical member B31 to electrically conduct with the testing object so as to measure the electrical conductivity of the testing object. Therefore, the electrical conductive signal is collected and is transmitted to the processing unit B12 for analyzing and processing of the strength of the electrical conductivity of the testing object.

Accordingly, physical properties and chemical properties of different precious stones are pre-stored in the microcontroller B10 for comparison so as to ensure the testing apparatus to rapidly and accurately identify the testing object. In particular, the thermal conductivity data, electrical conductivity data, and color data of different precious stones in a theoretical manner are pre-stored in the microcontroller B10 for comparing with the measured thermal conductivity and electrical conductivity of the testing object in order to classify the testing object.

It is worth mentioning that the processing unit B12 will comprehensively analyze and process the strengths of the thermal conductivity and the electrical conductivity of the testing object for comparing with the pre-stored thermal conductivity data and electrical conductivity data in order to identify the testing object. Accordingly, the measured thermal conductivity, the measured electrical conductivity, and detected color will correspondingly compare with the thermal conductivity data, electrical conductivity data, and color data.

It is worth mentioning that the thermal conductivity and the electrical conductivity of the testing object can be measured at the same time. Or, the thermal conductivity of the testing object will be measured first before the measurement of the electrical conductivity of the testing object. Of course, the thermal conductivity of the testing object will be measured after the measurement of the electrical conductivity of the testing object. The processing unit B12 will comprehensively analyze and process the strengths of the thermal conductivity and the electrical conductivity of the testing object in order to identify the testing object.

After the processing unit B12 generates the test result, the test result will be transmitted to the display B43 and/or the voice indicator B44 through the transmission unit B13. At the same time, the test result will also be transmitted to the electronic device, such as smart phone, tablet, or "cloud storage" through the transmission unit B13.

Figure 47:
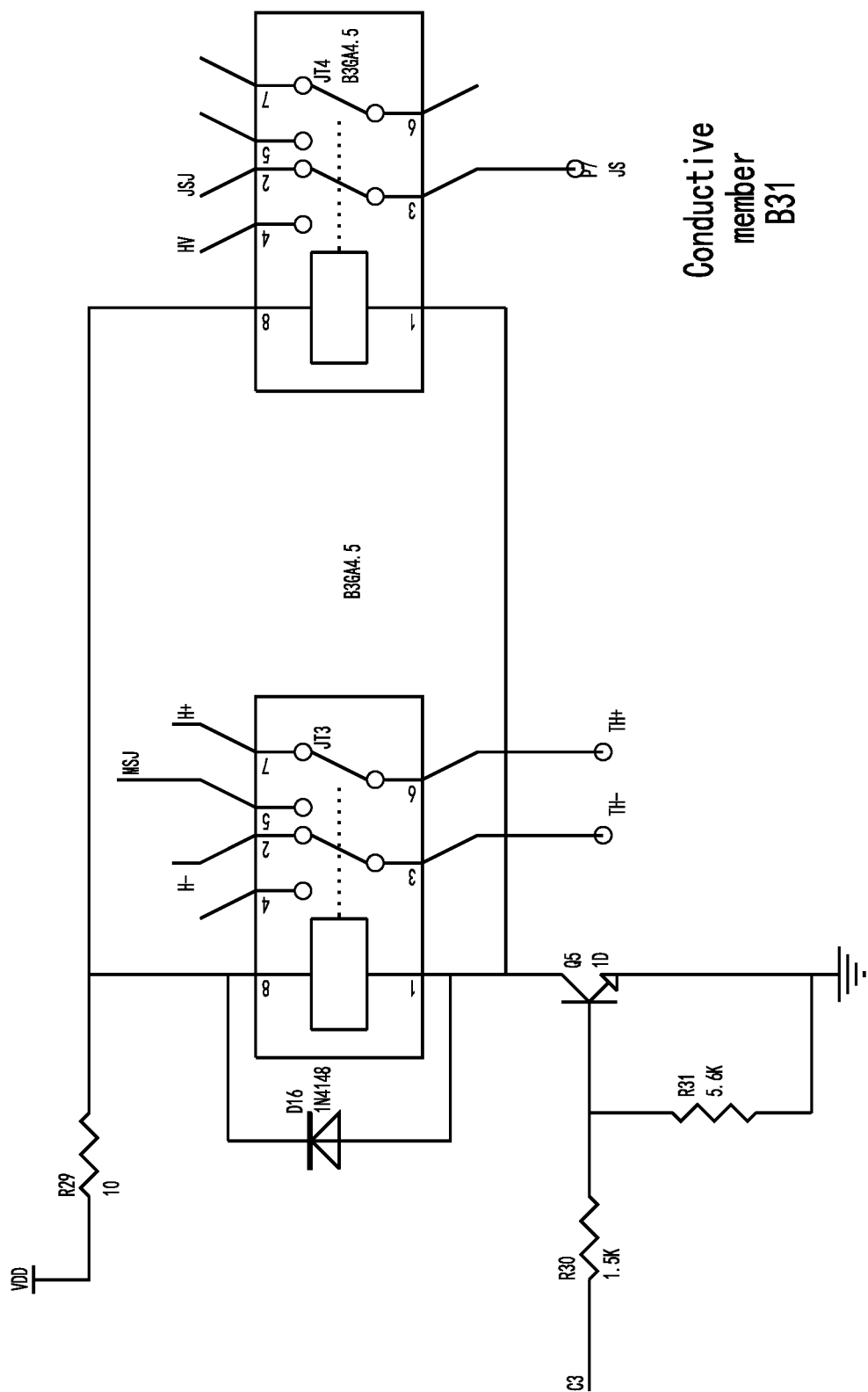
FIG. 47 illustrates a Moissanite detection circuit of the multi-functional precious stone testing apparatus according to the above third preferred embodiment of the present invention.
Figure 48:
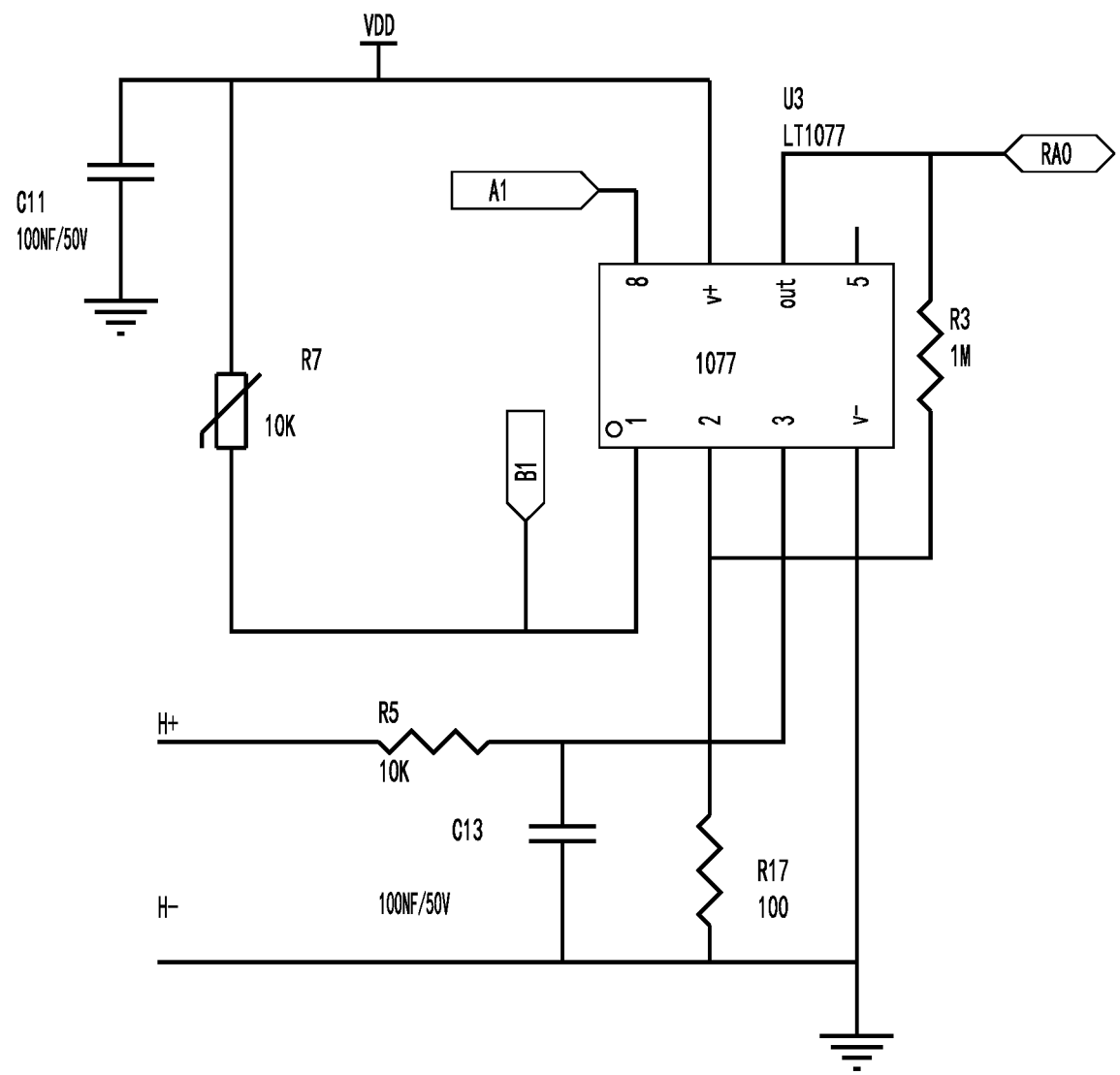
FIG. 48 illustrates a natural diamond detection circuit of the multi-functional precious stone testing apparatus according to the above third preferred embodiment of the present invention.
Figure 49:
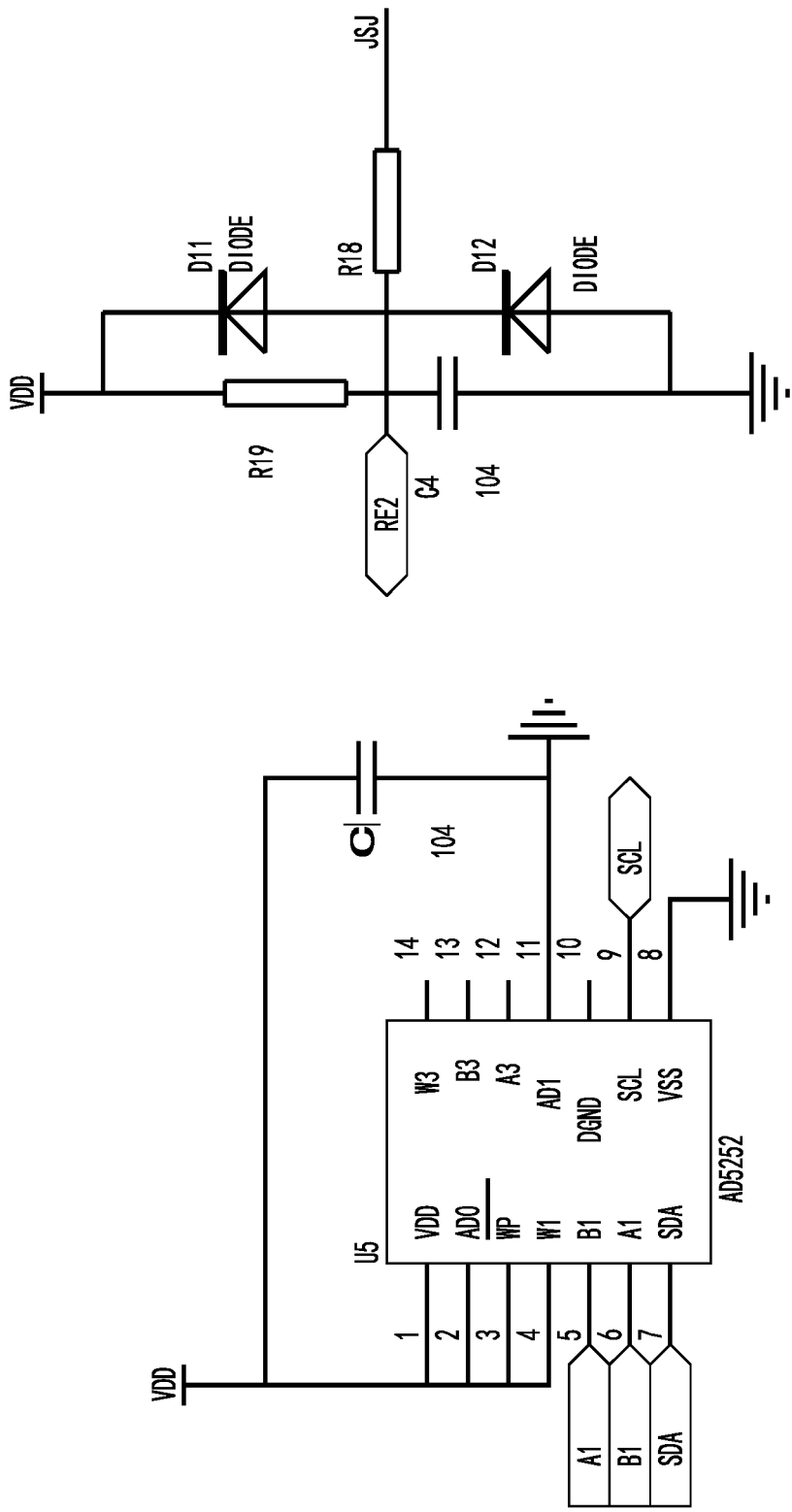
FIG. 49 illustrates a "metal element" and "other gemstones" detection circuit of the multi-functional precious stone testing apparatus according to the above third preferred embodiment of the present invention.

The testing object is determined as Moissanite when the strengths of the thermal conductivity and the electrical conductivity are strong. The display B43 will display the word "Moissanite" and the voice indicator B44 will generate a voice of "Moissanite". The testing object is determined as natural diamond when the strength of the thermal conductivity is strong and the strength of the electrical conductivity is weak. The display B43 will display the word "natural diamond" and the voice indicator B44 will generate a voice of "natural diamond". The testing object is determined as metal element when the strength of the thermal conductivity is weak and the strength of the electrical conductivity is strong. The display B43 will display the word "metal element" and the voice indicator B44 will generate a voice of "metal element". The testing object is determined as "other gemstones" when the strengths of the thermal conductivity and the electrical conductivity are weak. The display B43 will display the word "other gemstones" and the voice indicator B44 will generate a voice of "other gemstones". It is worth mentioning that the test of "other gemstones" should be further identified for accuracy. FIGS. 47 to 49 illustrate different detection circuits for Moissanite, natural diamond, metal element, other gemstones.

When the testing object is determined as "other gemstones", the method further executes a color classification operation. Accordingly, a color selection menu is shown in the display B43. The color selection menu can be activated automatically in response to the test result of "other gemstones", or can be activated manually by the user. The color selections are displayed on the display B43 that the user is able to select one of the color selections for identifying the color of the testing object, wherein the selected color selection will be sent to the processing unit B12. Then, the processing unit B12 will compare the selected color selection with the color data to preliminary categorize the testing object based upon the color thereof. The preliminary categorizing result will be transmitted to and displayed by the display B43 via the transmission unit B13. Then, the thermal conductivity and the electrical conductivity of the testing object will be further measured. Having the preliminary categorization of the testing object, the processing unit B12 will comprehensively analyze and process the strengths of the thermal conductivity and the electrical conductivity, and the color of the testing object via the microcontroller in order to identify the testing object. It is worth mentioning that the testing object will be tested and compared with 32 different kinds of precious stones pre-stored in the microcontroller B10.

It is worth mentioning that the color of the testing object can be identified by human observation, gemstone material identifying instruments, or other gemstone detecting instruments, such as spectroscopy or light reflection to determine the color of the testing object, such that the color of the testing object can be detected by any color detection instrument. Accordingly, the user is able to input the color of the testing object via the display B43, wherein the color selections are displayed on the display B43, such that the user is able to select one of the color selections for identifying the color of the testing object. FIG. 39 illustrates the color selections for different precious stone. The selected color selection will be compared with the color data to preliminary categorize the testing object based upon the color thereof. Accordingly, FIG. 39 illustrates 30 different kinds of precious stone with their own color properties.

According to the principle of the present invention, the testing apparatus is able to test natural diamonds, Mossianite, and 30 different kinds of colored precious stones.

When the testing object is determined as "other gemstones", the method further executes a color classification operation that the color selection menu is shown in the display B43. For example, when the testing object is white color, according to FIG. 39, the processing unit B12 will preliminary classify the testing object as one of glass, Nephrite, tourmaline, Jadeite, and Chrysoberyl. Then, by further measuring the thermal conductivity and the electrical conductivity of the testing object, the processing unit B12 will comprehensively analyze and process the strengths of the thermal conductivity and the electrical conductivity, and the color of the testing object via the microcontroller in order to identify the testing object as one of the above five precious stones through the preliminary categorization. Likewise, when the testing object is red color, according to FIG. 39, the processing unit B12 will preliminary classify the testing object as one of glass, Almandine, Pyrope, Spessartite, Rubellite, Jadeite, Spinel, Topaz, and Ruby. Then, by further measuring the thermal conductivity and the electrical conductivity of the testing object, the processing unit B12 will comprehensively analyze and process the strengths of the thermal conductivity and the electrical conductivity, and the color of the testing object via the microcontroller in order to identify the testing object as one of the above nine precious stones through the preliminary categorization.

Figure 41:
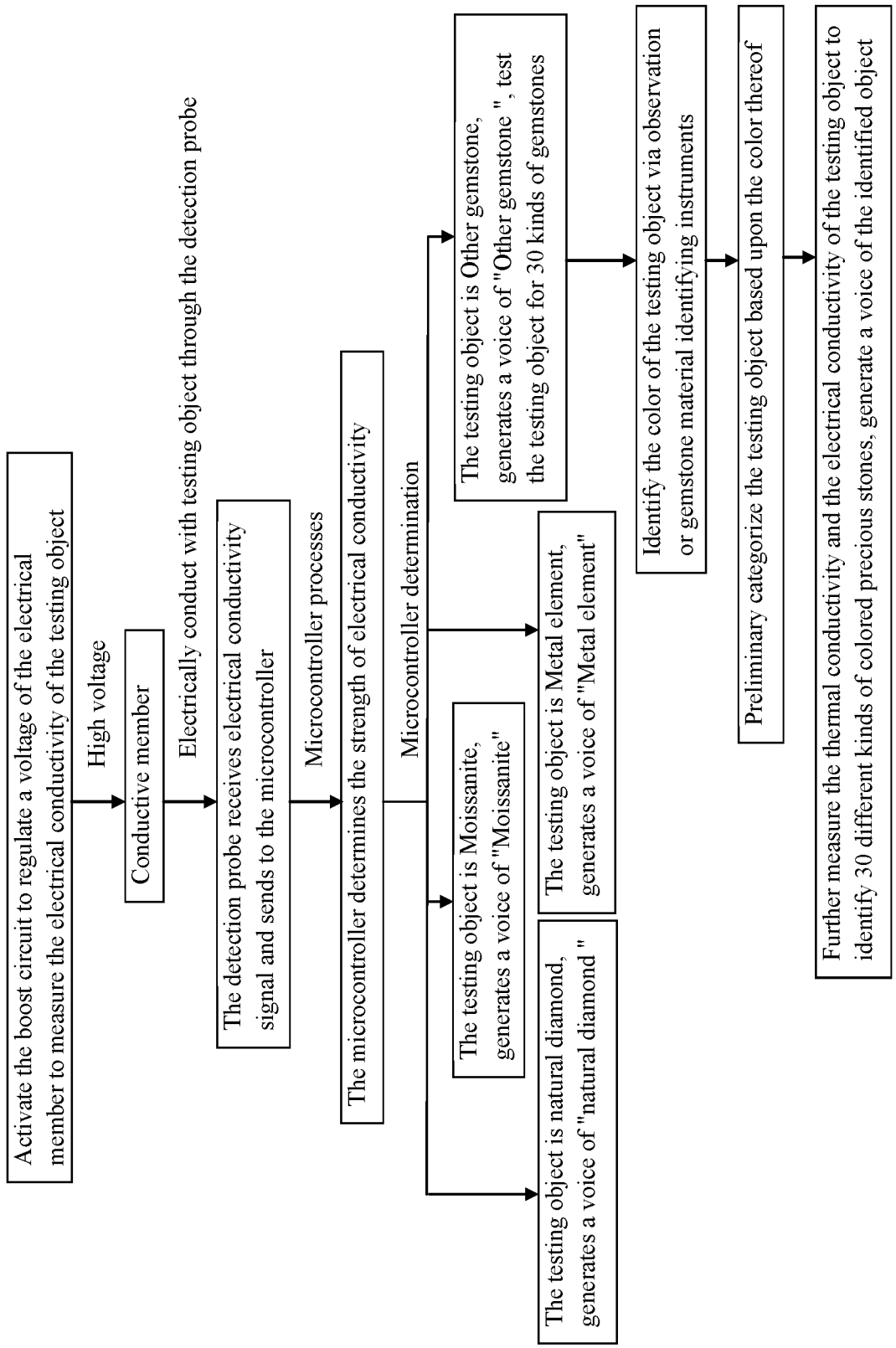
FIG. 41 illustrates a flow diagram of electrical conductivity testing of the testing object via the multi-functional precious stone testing apparatus according to the above third preferred embodiment of the present invention.

Accordingly the method of classifying a testing object by the multi-functional precious stone testing apparatus, as shown in FIGS. 38 and 41, wherein the method comprises the following steps.

(A) Contact the detection probe B21 with the testing object.

(B) Controllably activate at least one thermistor B22, preferably two, to control the heat energy change of the detection probe B21 for measuring the thermal conductivity of the testing object, and send a corresponding thermal conductive signal to the microcontroller B10 for analyzing and processing of the strength of the thermal conductivity of the testing object.

(C) Activate the booster circuit B14 controllably regulate the voltage of the electrical member B31, preferably high voltage, to electrically conduct with the testing object for measuring the electrical conductivity of the testing object, and send a corresponding electrical conductive signal to the microcontroller B10 for analyzing and processing of the strength of the electrical conductivity of the testing object.

(D) Comprehensively analyze and process the strengths of the thermal conductivity and the electrical conductivity of the testing object via the microcontroller B10 in order to identify the testing object.

It is worth mentioning that the step (B) and step (C) can be performed at the same time to simultaneously measure the thermal conductivity and the electrical conductivity of the testing object. Alternatively, the step (B) can be performed before the step (C) to measure the thermal conductivity and the electrical conductivity of the testing object in a sequence.

In the step (D), the test result is determined by the following criteria. The testing object is determined as Moissanite when the strengths of the thermal conductivity and the electrical conductivity are strong. The testing object is determined as natural diamond when the strength of the thermal conductivity is strong and the strength of the electrical conductivity is weak. The testing object is determined as metal element when the strength of the thermal conductivity is weak and the strength of the electrical conductivity is strong. The testing object is determined as "other gemstones" when the strengths of the thermal conductivity and the electrical conductivity are weak. It is worth mentioning that the test of "other gemstones" should be further identified for accuracy.

When the testing object is determined as "other gemstones", the method further comprises the following steps.

(a) Identify the color of the testing object.

(b) Preliminary categorize the testing object based upon the color thereof.

(c) Further measure the thermal conductivity and the electrical conductivity of the testing object.

(d) Comprehensively analyze and process the strengths of the thermal conductivity and the electrical conductivity, and the color of the testing object via the microcontroller B10 in order to identify the testing object.

Accordingly, the testing apparatus is able to rapidly and accurately identify the testing object as one of the natural diamonds, Mossianite, and 30 different kinds of colored precious stones. The testing apparatus of the present invention is compact, portable, and easy to use, and the operation process is simple through the simple steps to generate the accurate test result.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A multi-functional precious stone testing apparatus for identifying a testing object, comprising:
    a measuring module that selectively measures one of a combination of ultraviolet and infrared distributions of the testing object and a combination of thermal and electrical conductivities of the testing object;
    a microcontroller operatively linked to said measuring module, wherein said microcontroller analyzes a result from said measuring module to generate a test result of the testing object, wherein said microcontroller comprises a communication unit adapted for connecting with an external electronic device to transmit said test result thereto; and
    a functional unit operatively linked to said microcontroller, wherein said functional unit comprises a voice indicator that generates a voice indication signal of said test result for vocally saying out a diamond identity of the testing object.

2. The testing apparatus, as recited in claim 1, wherein said communication unit is a wireless communication unit for wirelessly connecting with the external electronic device to wirelessly transmit said test result thereto.

3. The testing apparatus, as recited in claim 1, further comprising a portable housing that said measuring module, said microcontroller and said function unit are received in said portable housing to form a handheld apparatus, wherein said measuring module comprises:
    an infrared test system which comprises an infrared transmitter for emitting infrared to a surface of the testing object, and an infrared receiver receiving a reflection of the infrared from the surface of the testing object;
    a UV transmission system which comprises a short-wave ultraviolet UVA transmitter and a long-wave ultraviolet UVA transmitter for emitting short-wave ultraviolet (UVC) and long-wave ultraviolet (UVA) to penetrate the testing object; and
    a UV receiving system which comprises a short-wave ultraviolet sensor and a long-wave ultraviolet sensor for receiving the short-wave ultraviolet and long-wave ultraviolet after the penetration through the testing object, wherein said microcontroller operatively linked to said infrared receiver of said infrared test system and said UV receiving system for receiving infrared data and UV data and for analysis processing said infrared data and UV data so as to generate said test result of the testing object.

4. The testing apparatus, as recited in claim 3, wherein said short-wave ultraviolet UVC transmitter comprises a boost inverter circuit and at least one short-wave ultraviolet light device, wherein said long-wave ultraviolet UVA transmitter comprises a constant current circuit and at least one long-wave ultraviolet light device, wherein said boost inverter circuit and said constant current circuit are connected said short-wave ultraviolet light device and said long-wave ultraviolet light device which are activated to emit UVC and UVA respectively.

5. The testing apparatus, as recited in claim 3, wherein said microcontroller further comprises a processing unit operatively linked to said UV receiving system for processing and analyzing the UV data so as to generate said test result, and a transmission unit operatively linked to said processing unit to transmit the test result to said functional unit and to transmit the test result to the external electronic device through said communication unit, so as to allow said test result to be stored digitally, viewed, accessed, and edited via the electronic device.

6. The testing apparatus, as recited in claim 3, wherein said functional unit further comprises a light indicator which are connected to said microcontroller, wherein said test result is sent by said microcontroller to said light indicator for generating a light indication signal of the testing object.

7. The testing apparatus, as recited in claim 3, wherein said microcontroller identities the testing object as Moissanite when said short-wave ultraviolet and said long-wave ultraviolet received by said short-wave ultraviolet sensor and said long-wave ultraviolet sensor are weak, wherein said microcontroller identities the testing object as natural diamond when said short-wave ultraviolet received by said short-wave ultraviolet sensor is weak and said long-wave ultraviolet received by said long-wave ultraviolet sensor is strong, wherein said microcontroller identities the testing object as synthetic diamond when said short-wave ultraviolet received by said short-wave ultraviolet sensor is strong.

8. The testing apparatus, as recited in claim 3, further comprising a protection cover and having a test area for the testing object placing thereon, wherein said protection cover is actuated to selectively close said test area for enclosing the testing object so as to test the testing object in a closed environment.

9. The testing apparatus, as recited in claim 1, wherein said measuring module comprises:
    a probe head assembly which comprises at least a detection probe operatively connected to said microcontroller and at least a thermistor operatively connected to said detection probe, wherein said detection probe is arranged for measuring said thermal conductivity of the testing object when said detection probe contacts therewith; and
    an electrical conductive assembly which comprises at least an electrical member operatively linked to said microcontroller, and an electrical conductor, wherein said microcontroller is activated to controllably regulate a voltage of said electrical member, said electrical conductor conducts with the testing object to measure said electrical conductivity of the testing object, wherein said microcontroller comprehensively analyzes and processes strengths of said thermal conductivity and said electrical conductivity of the testing object in order to identify the testing object.

10. The testing apparatus, as recited in claim 9, wherein said microcontroller which comprises an amplifying circuit that amplifies a thermal conductive signal from said probe head assembly, a booster circuit being activated to controllably regulate the voltage of said electrical member, and a processing unit analyzing and processing said thermal conductive signal from said probe head assembly and an electrical conductive signal from said electrical conductive assembly.

11. The testing apparatus, as recited in claim 9, wherein said functional unit further comprises a light indicator which are connected to said microcontroller, wherein said test result is sent by said microcontroller to said light indicator for generating a light indication signal of the testing object.

12. The testing apparatus, as recited in claim 9, wherein said microcontroller identities the testing object as Moissanite when the strengths of said thermal conductivity and said electrical conductivity are strong, wherein said microcontroller identities the testing object as natural diamond when the strength of said thermal conductivity is strong and the strength of said electrical conductivity is weak, wherein said microcontroller identities the testing object as metal element when the strength of said thermal conductivity is weak and the strength of said electrical conductivity is strong, wherein said microcontroller identities the testing object as "other gemstones" when the strengths of said thermal conductivity and said electrical conductivity are weak.

13. The testing apparatus, as recited in claim 9, wherein said microcontroller further comprises a properties database containing thermal conductivity data, electrical conductivity data, and color data of different precious stones in a theoretical manner for comparing with measured thermal conductivity and electrical conductivity of the testing object.

14. The testing apparatus, as recited in claim 9, wherein two of said thermistors are used in such a manner that one of said thermistors heats up said detection probe at a predetermined pre-heat temperature for transferring heat to the testing object when said detection probe contacts with the testing object, while another said thermistor measures a temperature change at said detection probe for measuring said thermal conductivity of the testing object.

15. A method of classifying a testing object by a multi-functional precious stone testing apparatus which comprises a measuring module, a microcontroller, and a functional unit, wherein the method comprises the steps of:
(a) measuring properties of the testing object by said measuring module that measures one of a combination of ultraviolet and infrared distributions of the testing object and a combination of thermal and electrical conductivities of the testing object;
(b) analyzing the properties of the testing object via said microcontroller through a result from said measuring module to generate a test result of the testing object; and
(c) wirelessly connecting said microcontroller with an external electronic device to wirelessly transmit said test result thereto;
wherein the step (a) further comprises the steps of:
(a.1) emitting infrared to a surface of the testing object, and emitting UVC and UVA to penetrate the testing object;
(a.2) receiving reflection of said infrared from the surface of the testing object and said UVC and UVA after penetration of the testing object, and sending infrared data and UV data to the microcontroller, such that said microcontroller analyzes UV intensity from said UV data and infrared spectrum from said infrared data to identify the testing object;
wherein the step (b) further comprises the steps of:
(b.1) identifying the testing object as Moissanite when said short-wave ultraviolet and said long-wave ultraviolet received by a short-wave ultraviolet sensor and a long-wave ultraviolet sensor are weak;
(b.2) identifying the testing object as natural diamond when said short-wave ultraviolet received by said short-wave ultraviolet sensor is weak and said long-wave ultraviolet received by said long-wave ultraviolet sensor is strong; and
(b.3) identifying the testing object as synthetic diamond when said short-wave ultraviolet received by said short-wave ultraviolet sensor is strong.

16. The method, as recited in claim 15, wherein the step (a) further comprises the steps of:
(a.1) contacting a detection probe with the testing object;
(a.2) controllably activating at least a thermistor to control a heat energy change of said detection probe for measuring said thermal conductivity of the testing object, and sending a corresponding thermal conductive signal to said microcontroller for analyzing and processing of a strength of said thermal conductivity of the testing object; and
(a.3) controllably regulating a voltage of an electrical member at said detection probe to electrically conduct with the testing object for measuring said electrical conductivity of the testing object, and sending a corresponding electrical conductive signal to said microcontroller for analyzing and processing of a strength of said electrical conductivity of the testing object;
wherein the step (b) further comprises the steps of:
(b.1) identifying the testing object as Moissanite when the strengths of said thermal conductivity and said electrical conductivity are strong;
(b.2) identifying the testing object as natural diamond when the strength of said thermal conductivity is strong and the strength of said electrical conductivity is weak;
(b.3) identifying the testing object as metal element when the strength of said thermal conductivity is weak and the strength of said electrical conductivity is strong; and
(b.4) identifying the testing object as "other gemstones" when the strengths of said thermal conductivity and said electrical conductivity are weak.

17. A method of classifying a testing object by a multi-functional precious stone testing apparatus which comprises a measuring module, a microcontroller, and a functional unit, wherein the method comprises the steps of:
(a) measuring properties of the testing object by said measuring module that measures one of a combination of ultraviolet and infrared distributions of the testing object and a combination of thermal and electrical conductivities of the testing object;
(b) analyzing the properties of the testing object via said microcontroller through a result from said measuring module to generate a test result of the testing object; and
(c) generating a voice indication signal of said test result via a voice indicator of said functional unit for vocally saying out a diamond identity the testing object.

18. The method, as recited in claim 17, wherein the step (a) further comprises the steps of:

(a.1) emitting infrared to a surface of the testing object, and emitting UVC and UVA to penetrate the testing object;

(a.2) receiving reflection of said infrared from the surface of the testing object and said UVC and UVA after penetration of the testing object, and sending infrared data and UV data to the microcontroller, such that said microcontroller analyzes UV intensity from said UV data and infrared spectrum from said infrared data to identify the testing object;

wherein the step (b) further comprises the steps of:

(b.1) identifying the testing object as Moissanite when said short-wave ultraviolet and said long-wave ultraviolet received by a short-wave ultraviolet sensor and a long-wave ultraviolet sensor are weak;

(b.2) identifying the testing object as natural diamond when said short-wave ultraviolet received by said short-wave ultraviolet sensor is weak and said long-wave ultraviolet received by said long-wave ultraviolet sensor is strong; and (b.3) identifying the testing object as synthetic diamond when said short-wave ultraviolet received by said short-wave ultraviolet sensor is strong.

19. The method, as recited in claim 17, wherein the step (a) further comprises the steps of:

(a.1) contacting a detection probe with the testing object;

(a.2) controllably activating at least a thermistor to control a heat energy change of said detection probe for measuring said thermal conductivity of the testing object, and sending a corresponding thermal conductive signal to said microcontroller for analyzing and processing of a strength of said thermal conductivity of the testing object; and (a.3) controllably regulating a voltage of an electrical member at said detection probe to electrically conduct with the testing object for measuring said electrical conductivity of the testing object, and sending a corresponding electrical conductive signal to said microcontroller for analyzing and processing of a strength of said electrical conductivity of the testing object;

wherein the step (b) further comprises the steps of:

(b.1) identifying the testing object as Moissanite when the strengths of said thermal conductivity and said electrical conductivity are strong;

(b.2) identifying the testing object as natural diamond when the strength of said thermal conductivity is strong and the strength of said electrical conductivity is weak;

(b.3) identifying the testing object as metal element when the strength of said thermal conductivity is weak and the strength of said electrical conductivity is strong; and (b.4) identifying the testing object as "other gemstones" when the strengths of said thermal conductivity and said electrical conductivity are weak.

* * * * *